United States Patent [19]

Reitz

[11] Patent Number: 5,451,591
[45] Date of Patent: Sep. 19, 1995

[54] METHOD OF USING 5-ARYLHETEROARYLALKYL-1,3 5-TRISUBSTITUTED-1,2,4-TRIAZOLE COMPOUNDS FOR TREATMENT OF CIRCULATORY DISORDERS

[75] Inventor: David B. Reitz, Chesterfield, Mo.

[73] Assignee: G. D. Searle & Co., Chicago, Ill.

[21] Appl. No.: 173,589

[22] Filed: Dec. 21, 1993

Related U.S. Application Data

[62] Division of Ser. No. 903,594, Jun. 24, 1992, abandoned, which is a division of Ser. No. 674,276, Mar. 21, 1991, Pat. No. 5,196,537.

[51] Int. Cl.$^6$ .............................................. A61K 31/44
[52] U.S. Cl. ..................... 514/337; 514/338; 514/339; 514/340; 514/341; 514/824
[58] Field of Search ............... 514/340, 341, 337, 338, 514/339, 824

[56] References Cited

U.S. PATENT DOCUMENTS 4,816,463  3/1989  Blankley et al. ............... 514/293
4,880,804  11/1989  Carini et al. ............... 514/234.5

FOREIGN PATENT DOCUMENTS 621842  2/1963  Belgium .
7180  10/1981  European Pat. Off. .
253310  1/1988  European Pat. Off. .... C07D 403/14
283310  9/1988  European Pat. Off. .... C07D 295/04
323841  7/1989  European Pat. Off. .... C07D 249/02
160447  8/1983  Germany .................. A01N 43/64

OTHER PUBLICATIONS

P. C. Wong et al, *J. Pharmacol. Exp. Ther.*, 247(1), 1–7 (1988).
A. T. Chiu et al, *European J. Pharmacol.*, 157, 13–21 (1988).
A. T. Chiu et al. *J. Pharmacol. Exp. Ther.*, 250(3), 867–874 (1989).

*Primary Examiner*—C. Warren Ivy
*Assistant Examiner*—Raymond Covington
*Attorney, Agent, or Firm*—J. Timothy Keane

[57] ABSTRACT

A class of 5-arylheteroarylalkyl-1,3,5-trisubstituted-1,2,4-triazole compounds is described for use in treatment of circulatory disorders such as hypertension. Compounds of particular interest are angiotensin II antagonists of the formula

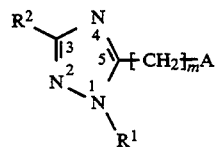

wherein A is selected from

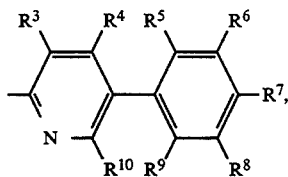

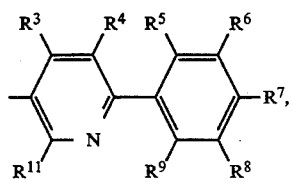

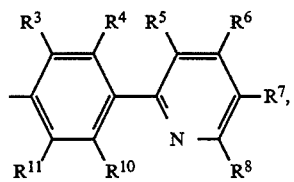

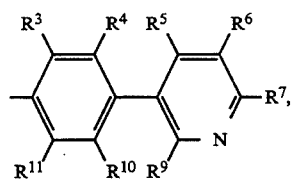

(Abstract continued on next page.)

-continued

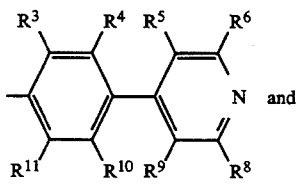

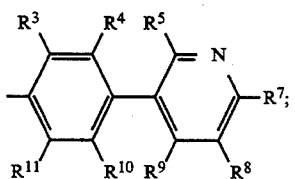

wherein m is one; wherein $R^1$ is selected from ethyl, n-propyl, isopropyl, n-butyl, sec-butyl, isobutyl, tert-butyl, 4-methylbutyl, n-pentyl, neopentyl, benzyl, cyclohexyl, cyclohexylmethyl, 2-butenyl, 3-butenyl, 2-butynyl, 3-butynyl and 2-hydroxybutyl; wherein $R^2$ is selected from ethyl, n-propyl, isopropyl, n-butyl, sec-butyl, isobutyl, 4-methylbutyl, tert-butyl, n-pentyl, neopentyl, 1-oxoethyl, 1-oxopropyl, 1-oxobutyl, 1-oxopentyl, 1,1-dimethoxypropyl, 1,1-dimethoxypentyl, halo, difluoromethyl, 1-oxo-2-phenylethyl, 1-oxo-2-cyclohexylethyl, 1,1-difluoro-2-phenylethyl, 1,1-difluoro-2-cyclohexylethyl, 2-cyclohexylethyl, 1,1-difluoro-3-cyclohexylpropyl, 1,1-dimethoxybutyl, 1,1-difluoroethyl, 1,1-difluoropropyl, 1,1-difluorobutyl, 1,1-difluoropentyl, benzyl, 2-phenylethyl, 1,1-difluoro-3-phenylpropyl, cyclohexylmethyl, cyclohexanoyl, 1-butenyl, 2-butenyl, 3-butenyl, 1-butynyl, 2-butynyl, 3-butynyl, propylthio and butylthio; wherein each of $R^3$, $R^4$, $R^6$ through $R^{11}$ is hydrido and $R^5$ is selected from COOH, SH, $PO_3H_2$, $SO_3H$, $CONHNH_2$, $CONHNHSO_2CF_3$, OH,

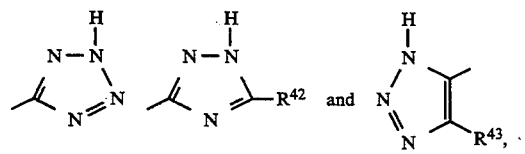

wherein each of $R^{42}$ and $R^{43}$ is independently selected from chromo, cyano, nitro, trifluoromethyl, methoxycarbonyl and trifluoromethylsulfonyl.

24 Claims, No Drawings

METHOD OF USING 5-ARYLHETEROARYLALKYL-1,3 5-TRISUBSTITUTED-1,2,4-TRIAZOLE COMPOUNDS FOR TREATMENT OF CIRCULATORY DISORDERS

This is a division of application Ser. No. 07/903,594 filed Jun. 24, 1991, now abandoned which is a division of application Ser. No. 07/674,276 filed Mar. 21, 1991 now U.S. Pat. No. 5,196,537.

FIELD OF THE INVENTION

Non-peptidic 5-arylheteroarylalkyl-1,3,5-trisubstituted-1,2,4-triazole compounds are described for use in treatment of circulatory disorders such as hypertension arid congestive heart failure. Of particular interest are angiotensin II antagonist compounds provided by 1,2,4-triazoles having a heteroarylmethyl moiety attached to the carbon atom at the five-position of the 1,2,4-triazole.

BACKGROUND OF THE INVENTION

The renin-angiotensin system is one of the hormonal mechanisms involved in regulation of pressure/volume homeostasis and in expression of hypertension. Activation of the renin-angiotensin cascade begins with renin secretion from the juxtaglomerular apparatus of the kidney and culminates in the formation of angiotensin II, the primary active species of this system. This octapeptide, angiotensin II, is a potent vasoconstrictor agent and also produces other physiological effects such as promoting aldosterone secretion, promoting sodium and fluid retention, inhibiting renin secretion, increasing sympathetic nervous system activity, increasing vasopressin secretion, causing positive cardiac inotropic effect and modulating other hormonal systems.

Previous studies have shown that antagonizing angiotensin II at its receptors is a viable approach to inhibit the renin-angiotensin system, given the pivotal role of this octapeptide which mediates the actions of the renin-angiotensin system through interaction with various tissue receptors. There are several known angiotensin II antagonists, most of which are peptidic in nature. Such peptidic compounds are of limited use due to their lack of oral bioavailability or their short duration of action. Also, commercially-available peptidic angiotensin II antagonists (e.g., Saralasin) have a significant residual agonist activity which further limit their therapeutic application.

Non-peptidic compounds with angiotensin II antagonist properties are known. For example, the sodium salt of 2-n-butyl-4-chloro-1-(2-chlorobenzyl)imidazole-5-acetic acid has specific competitive angiotensin II antagonist activity as shown in a series of binding experiments, functional assays and in vivo tests [P. C. Wong et al, *J. Pharmacol. Exp. Ther.*, 247 (1), 1–7 (1988)]. Also, the sodium salt of 2-butyl-4-chloro-1-(2-nitrobenzyl)imidazole-5-acetic acid has specific competitive angiotensin II antagonist activity as shown in a series of binding experiments, functional assays and in vivo tests [A. T. Chiu et al, *European J. Pharmacol.*, 157, 3121 (1988)]. A family of 1-benzylimidazole-5-acetate derivatives has been shown to have competitive angiotensin II antagonist properties [A. T. Chiu et al, *J. Pharmacol. Exp. Ther.*, 250(3), 867–874 (1989)]. U.S. Pat. No. 4,816,463 to Blankey et al describes a family of 4,5,6,7-tetrahydro-1H-imidazo(4,5-c)-tetrahydro-pyridine derivatives useful as antihypertensives, some of which are reported to antagonize the binding of labelled angiotensin II to rat adrenal receptor preparation and thus cause a significant decrease in mean arterial blood pressure in conscious hypertensive rats. EP No. 253,310, published 20 Jan. 1988, describes a series of aralkyl imidazole compounds, including in particular a family of biphenylmethyl substituted imidazoles, as antagonists to the angiotensin II receptor. EP No. 323,841 published 12 Jul. 1989 describes four classes of angiotensin II antagonists, namely, biphenylmethylpyrroles, biphenylmethylpyrazoles, biphenylmethyl-1,2,3-triazoles and biphenylmethyl 4-substituted-4H-1,2,4-triazoles, including the compound 3,5-dibutyl-4-[(2'-carboxybiphenyl-4-yl)methyl]-4H-1,2,4-triazole. U.S. Pat. No. 4,880,804 to Carini et al describes a family of biphenylmethylbenzimidazole compounds as angiotensin II receptor blockers for use in treatment of hypertension and congestive heart failure.

There are several families of known compounds having one or two oxo substituents on the triazole ring. For example, East German Patent No. 160,447 published 3 Aug. 1983 describes a family of 1,2,4-triazolin-5-one compounds, specifically 2,4-dihydro-4,5-bis(phenylmethyl)-3H-1,2,4-triazol-3-one, for use as herbicides. Belgian Patent No. 806,146 published 16 Oct. 1972 describes a family of triazolinone compounds, including the compound (3-(4-m-chlorophenyl-1-piperazinyl)-propyl)-3,4-diethyl-1,2,4-triazolin-5-one, having tranquilizer, hypotensive and analgesic activities. Belgian Patent No. 631,842 published 28 Feb. 1963 describes a family of 1,2,4-triazolones having hypnotic, tranquilizer, narcotic, sedative and analgetic activities, which includes a class of 4-N-aralkyl-1,2,4-triazol-5-one compounds. EP #7,180 published 15 Jun. 1978 describes a family of 1,2-disubstituted-4-alkyl-1,2,4-triazolidine-3,5-dione compounds having a wide variety of activities, such as antiulcer, bronchodilator, antifertility and cardiovascular-related activities which include antihypertensive, antiarrhythmic, platelet aggregation inhibition and smooth muscle activities. EP #283,310 published 18 Mar. 1987 describes a family of N1-diarylmethyl-N2-aminoalkyl-diaza-heterocyclic derivatives for treating cerebral vascular and ischmic diseases and for protecting against anoxia.

DESCRIPTION OF THE INVENTION

A class of 5-arylheteroarylalkyl-1,3,5-trisubstituted-1,2,4-triazole compounds useful in treating circulatory disorders, particularly cardiovascular disorders, is defined by Formula I:

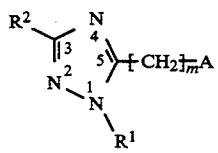

wherein A is selected from

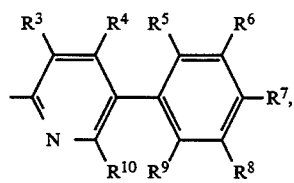

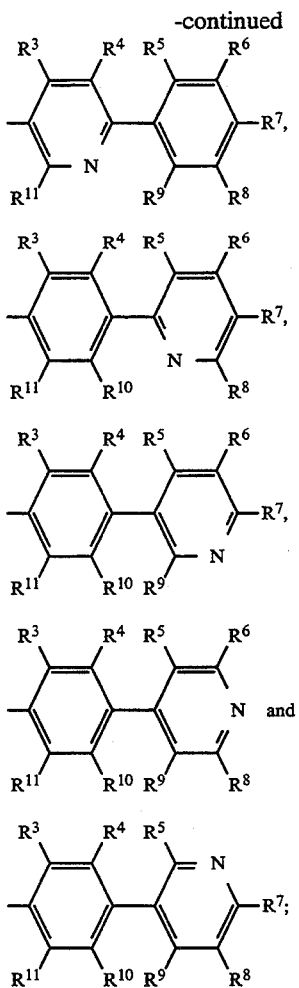

wherein m is a number selected from one to four, inclusive;
wherein $R^1$ is selected from hydrido, alkyl, hydroxyalkyl, haloalkyl, cycloalkyl, cycloalkylalkyl, formyl, aralkyl, aryl, aroyl, alkoxyalkyl, alkylcarbonyl, alkylcarbonylalkyl, alkoxycarbonyl, alkenyl, cycloalkenyl, aralkoxycarbonyl, alkynyl, alkylthiocarbonyl, alkylthiothiocarbonyl, arylthiocarbonyl, arylthiothiocarbonyl, aralkylthiocarbonyl, alkylthiocarbonyl, alkylsulfinyl, alkylsulfonyl, aralkylsulfinyl, aralkylsulfonyl, arylsulfinyl, arylsulfonyl, heteroaryl having one or more ring atoms selected from oxygen, sulfur and nitrogen atoms, and amido radicals of the formula

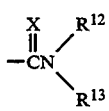

wherein X is oxygen atom or sulfur atom; wherein each of $R^{12}$ and $R^{13}$ is independently selected from hydrido, alkyl, cycloalkyl, cyano, amino, monoalkylamino, dialkylamino, hydroxyalkyl, cycloalkylalkyl, alkoxyalkyl, aralkyl and aryl, and wherein $R^{12}$ and $R^{13}$ taken together may form a heterocyclic group having five to seven ring members including the nitrogen atom of said amido radical and which heterocyclic group may further contain one or more hetero atoms as ring members selected from oxygen, nitrogen and sulfur atoms and which heterocyclic group may be saturated or partially unsaturated; wherein each of $R^{12}$ and $R^{13}$ taken together may form an aromatic heterocyclic group having five ring members including the nitrogen atom of said amido radical and which aromatic heterocyclic group may further contain one or more additional nitrogen atoms; wherein each of $R^2$ through $R^{11}$ is independently selected from hydrido, alkyl, hydroxyalkyl, halo, haloalkyl, cycloalkyl, cycloalkylalkyl, cycloalkylhaloalkyl, cycloalkylcarbonyl, formyl, alkoxy, aralkyl, aralkylhaloalkyl, aryl, aroyl, aryloxy, aryloxyalkyl, aralkoxy, alkoxyalkyl, alkylcarbonyl, alkylcarbonylalkyl, alkoxycarbonyl, alkenyl, cycloalkenyl, alkynyl, cyano, nitro, carboxyl, carboxyalkyl, alkylcarbonyloxy, alkylcarbonyloxyalkyl, alkoxycarbonylalkyl, aralkoxycarbonylalkyl, aralkylcarbonyloxyalkyl, mercaptocarbonyl, mercaptothiocarbonyl, mercaptoalkyl, alkoxycarbonyloxy, alkylthio, cycloalkylthio, cycloalkylalkylthio, alkylthiocarbonyl, alkylcarbonylthio, alkylthiocarbonyloxy, alkylthiocarbonylthio, alkylthiothiocarbonyl, alkylthiothiocarbonylthio, arylthio, arylthiocarbonyl, arylcarbonylthio, arylthiocarbonyloxy, arylthiocarbonylthio, arylthiothiocarbonyl, arylthiothiocarbonylthio, aralkylthio, aralkylthiocarbonyl, aralkylcarbonylthio, aralkylthiocarbonyloxy, aralkylthiocarbonylthio, alkylthiocarbonyl, aralkylthiocarbonylthio, mercapto, alkylsulfinyl, alkylsulfonyl, aralkylsulfinyl, aralkylsulfonyl, arylsulfinyl, arylsulfonyl, phthalimido, phthalimidoalkyl, heteroaryl, heteroarylalkyl, cycloheteroalkyl, cycloheteroalkylalkyl and cycloheteroalkylcarbonylalkyl wherein each of said heteroaryl- and cyclohetero-containing groups has one or more ring atoms selected from oxygen, sulfur and nitrogen atoms, and wherein each of $R^2$ through $R^{11}$ may be further independently selected from amino and amido radicals of the formula

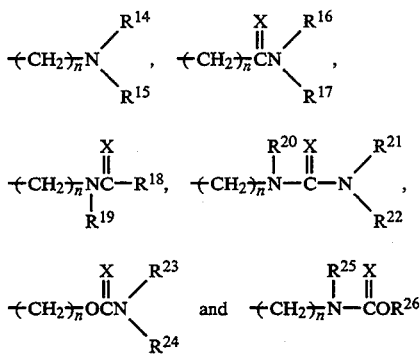

wherein X is oxygen atom or sulfur atom;
wherein each n is a number independently selected from zero to six, inclusive;
wherein each of $R^{14}$ through $R^{26}$ is independently selected from hydrido, alkyl, cycloalkyl, cyano, amino, monoalkylamino, dialkylamino, hydroxyalkyl, cycloalkylalkyl, alkoxyalkyl, aralkyl and aryl, and wherein $R^{14}$ and $R^{15}$ taken together, $R^{16}$ and $R^{17}$ taken together, $R^{18}$ and $R^{19}$ taken together, $R^{21}$ and $R^{22}$ taken together and $R^{23}$ and $R^{24}$ taken together may each form a heterocyclic group having five to seven ring members including the nitrogen atom of said amino or amido radical and which heterocyclic group may further contain one or more hetero atoms as ring members selected from oxygen, nitrogen and sulfur atoms and which heterocyclic group may be saturated or partially unsaturated; wherein $R^{14}$ and $R^{15}$ taken together, $R^{16}$ and $R^{17}$ taken together, $R^{21}$ and $R^{22}$ taken together and $R^{23}$ and $R^{24}$ taken together may each form an aromatic heterocyclic group having five ring members including the nitrogen atom of said amino or amido radical and which aromatic heterocyclic group may further contain one or more hetero atoms as ring atoms selected from oxygen, nitrogen and sulfur atoms;

and wherein each of $R^3$ through $R^{11}$ may be further independently selected from hydroxy and acidic moieties of the formula —$Y_nA$ wherein n is a number selected from zero through three, inclusive, and wherein A is an acidic group selected to contain at least one acidic hydrogen atom, and the amide, ester and salt derivatives of said acidic moieties; wherein Y is a spacer group independently selected from one or more of alkyl, cycloalkyl, cycloalkylalkyl, alkenyl, alkynyl, aryl, aralkyl and heteroaryl having one or more ring atoms selected from oxygen, sulfur and nitrogen atoms;

and wherein any of the foregoing $R^1$ through $R^{26}$, Y and A groups having a substitutable position may be substituted by one or more groups independently selected from hydroxy, alkyl, alkenyl, alkynyl, aralkyl, hydroxyalkyl, haloalkyl, halo, oxo, alkoxy, aryloxy, aralkoxy, aralkylthio, alkoxyalkyl, cycloalkyl, cycloalkylalkyl, aryl, aroyl, cycloalkenyl, cyano, cyanoamino, nitro, alkylcarbonyloxy, alkoxycarbonyloxy, alkylcarbonyl, alkoxycarbonyl, aralkoxycarbonyl, carboxyl, mercapto, mercaptocarbonyl, alkylthio, arylthio, alkylthiocarbonyl, alkylsulfinyl, alkylsulfonyl, haloalkylsulfonyl, aralkylsulfinyl, aralkylsulfonyl, arylsulfinyl, arylsulfonyl, heteroaryl having one or more ring atoms selected from oxygen, sulfur and nitrogen atoms, and amino and amido radicals of the formula

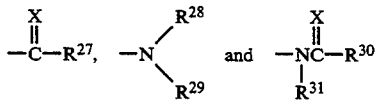

wherein X is oxygen atom or sulfur atom; wherein each of $R^{27}$ through $R^{31}$ is independently selected from hydrido, alkyl, cycloalkyl, cycloalkylalkyl, aralkyl, aryl, D$R^{32}$ and

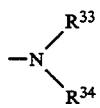

wherein D is selected from oxygen atom and sulfur atom and $R^{32}$ is selected from hydrido, alkyl, cycloalkyl, cycloalkylalkyl, aralkyl and aryl; wherein each of $R^{27}$, $R^{28}$, $R^{29}$, $R^{30}$, $R^{31}$, $R^{33}$ and $R^{34}$ is independently selected from hydrido, alkyl, cycloalkyl, cyano, hydroxyalkyl, haloalkyl, cycloalkylalkyl, alkoxyalkyl, alkylcarbonyl, alkoxycarbonyl, carboxyl, alkylsulfinyl, alkylsulfonyl, arylsulfinyl, arylsulfonyl, haloalkylsulfinyl, haloalkylsulfonyl, aralkyl and aryl, and wherein each of $R^{27}$, $R^{28}$, $R^{29}$, $R^{30}$, $R^{31}$, $R^{33}$ and $R^{34}$ is further independently selected from amino and amido radicals of the formula

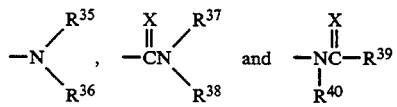

wherein X is oxygen atom or sulfur atom; wherein each of $R^{35}$, $R^{36}$, $R^{37}$ $R^{38}$, $R^{39}$ and $R^{40}$ is independently selected from hydrido, alkyl, cycloalkyl, cyano, hydroxyalkyl, cycloalkylalkyl, alkoxyalkyl, haloalkylsulfinyl, haloalkylsulfonyl, aralkyl and aryl, and wherein each of $R^{28}$ and $R^{29}$ taken together and each of $R^{30}$ and $R^{31}$ taken together may form a heterocyclic group having five to seven ring members including the nitrogen atom of said amino or amido radical, which heterocyclic group may further contain one or more hetero atoms as ring members selected from oxygen, nitrogen and sulfur atoms and which heterocyclic group may be saturated or partially unsaturated; wherein each of $R^{28}$ and $R^{29}$ taken together and each of $R^{33}$ and $R^{34}$ taken together may form an aromatic heterocyclic group having five ring members including the nitrogen atom of said amino or amido radical and which aromatic heterocyclic group may further contain one or more hetero atoms as ring atoms selected from oxygen, nitrogen and sulfur atoms; or a tautomer thereof or a pharmaceutically-acceptable salt thereof.

Compounds of Formula I would be useful in treating a variety of circulatory disorders, including cardiovascular disorders, such as hypertension, congestive heart failure and arteriosclerosis, and to treat other disorders such as glaucoma. These compounds would also be useful as adjunctive therapies. For example, compounds of Formula I may be used in combination with other drugs, such as a diuretic, to treat hypertension. Also, compounds of Formula I could be used in conjunction with certain surgical procedures. For example, these compounds could be used to prevent post-angioplasty re-stenosis. Compounds of Formula I are therapeutically effective in treatment of cardiovascular disorders by acting as antagonists to, or blockers of, the angiotensin II (AII) receptor. Compounds of Formula I would be therapeutically effective in treatment of the above-mentioned circulatory and cardiovascular disorders or would be precursors to, or prodrugs of, therapeutically-effective compounds.

The phrase "acidic group selected to contain at least one acidic hydrogen atom", as used to define the —$Y_nA$ moiety, is intended to embrace chemical groups which, when attached to any of the $R^3$ through $R^{11}$ positions of Formula I, confers acidic character to the compound of Formula I. "Acidic character" means proton-donor capability, that is, the capacity of the compound of Formula I to be a proton donor in the presence of a proton-receiving substance such as water. Typically, the acidic group should be selected to have proton-donor capability such that the product compound of Formula I has a p$K_a$ in a range from about one to about twelve. More typically, the Formula I compound would have a p$K_a$ in a range from about two to about seven. An example of an acidic group containing at least one acidic hydrogen atom is carboxyl group (—COOH). Where n is zero and A is —COOH, in the —$Y_nA$ moiety, such carboxyl group would be attached directly to one of the $R^3$ through $R^{11}$ positions. The Formula I compound may have one —$Y_nA$ moiety attached at one of the $R^3$ through $R^{11}$ positions, or may have a plurality of such —$Y_nA$ moieties attached at more than one of the $R^3$ through $R^{11}$ positions, up to a maximum of nine such —$Y_nA$ moieties. There are many examples of acidic groups other than carboxyl group, selectable to contain at least one acidic hydrogen atom. Such other acidic groups may be collectively referred to as "bioisosteres of carboxylic acid" or referred to as "acidic bioisosteres". Specific examples of such acidic bioisosteres are described hereinafter. Compounds of Formula I having the —$Y_nA$ moiety attached at one of positions $R^5$, $R^6$, $R^8$ and $R^9$ would be expected to have preferred properties, while attachment at $R^5$ or $R^9$ would be more preferred. Compounds of Formula I may have one or more acidic protons and, therefore, may have one or more $pK_a$ values. It is preferred, however, that at least one of these $pK_a$ values of the Formula I compound as conferred by the —$Y_nA$ moiety be in a range from about two to about seven. The —$Y_nA$ moiety may be attached to one of the $R^3$ through $R^{11}$ positions through any portion of the —$Y_nA$ moiety which results in a Formula I compound being relatively stable and also having a labile or acidic proton to meet the foregoing $pK_a$ criteria. For example, where the —$Y_nA$ acid moiety is tetrazole, the tetrazole is attached at the ring carbon atom.

A preferred class of compounds consists of those compounds of Formula I wherein m is one; wherein $R^1$ is selected from hydrido, alkyl, hydroxyalkyl, haloalkyl, cycloalkyl, cycloalkylalkyl, aralkyl, aryl, aroyl, alkoxyalkyl, alkylcarbonyl, alkoxycarbonyl, alkenyl, cycloalkenyl, alkynyl, cycloalkynyl, carboxyl, alkylthiocarbonyl, arylthiocarbonyl, arylthiothiocarbonyl, aralkylthiocarbonyl, alkylsulfonyl, aralkylsulfonyl, arylsulfonyl, heteroaryl having one or more ring atoms selected from oxygen, sulfur and nitrogen atoms, and amido radicals of the formula

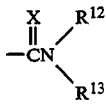

wherein X is oxygen atom or sulfur atom; wherein each of $R^{12}$ and $R^{13}$ is independently selected from hydrido, alkyl, cycloalkyl, cyano, amino, monoalkylamino, dialkylamino, hydroxyalkyl, cycloalkylalkyl, alkoxyalkyl, aralkyl and aryl;
wherein $R^2$ is selected from hydrido, alkyl, hydroxyalkyl, halo, haloalkyl, cycloalkyl, cycloalkylalkyl, cycloalkylhaloalkyl, cycloalkylcarbonyl, alkoxy, aralkyl, aralkylhaloalkyl, aryl, aroyl, aryloxy, aryloxyalkyl, aralkoxy, alkoxyalkyl, alkylcarbonyl, alkoxycarbonyl, alkenyl, cycloalkenyl, alkynyl, cycloalkynyl, cyano, nitro, carboxyl, carboxyalkyl, alkylcarbonyloxy, alkylcarbonyloxyalkyl, alkoxycarbonylalkyl, aralkoxycarbonylalkyl, aralkylcarbonyloxyalkyl, mercaptocarbonyl, mercaptothiocarbonyl, mercaptoalkyl, alkoxycarbonyloxy, alkylthio, cycloalkylthio, cycloalkylalkylthio, alkylthiocarbonyl, alkylcarbonylthio, alkylthiocarbonyloxy, alkylthiocarbonylthio, alkylthiothiocarbonyl, alkylthiothiocarbonylthio, arylthio, arylthiocarbonyl, arylcarbonylthio, arylthiocarbonyloxy, arylthiocarbonylthio, arylthiothiocarbonyl, arylthiothiocarbonylthio, aralkylthio, aralkylthiocarbonyl, aralkylcarbonylthio, aralkylthiocarbonyloxy, aralkylthiocarbonylthio, aralkylthiocarbonyl, aralkylthiocarbonylthio, mercapto, alkylsulfinyl, alkylsulfonyl, aralkylsulfinyl, aralkylsulfonyl, arylsulfinyl, arylsulfonyl, phthalimido, phthalimidoalkyl, heteroaryl, heteroarylalkyl, cycloheteroalkyl, cycloheteroalkylalkyl and cycloheteroalkylcarbonylalkyl wherein each of said heteroaryl- and cycloheteroalkyl-containing groups has one or more hetero ring atoms selected from oxygen, sulfur and nitrogen atoms, and wherein each of $R^2$ through $R^{11}$ may be further independently selected from amino and amido radicals of the formula

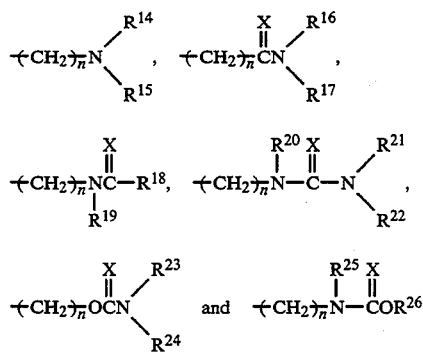

wherein X is selected from oxygen atom or sulfur atom; wherein each n is a number independently selected from zero to six, inclusive;
wherein each of $R^{14}$ through $R^{26}$ is independently selected from hydrido, alkyl, cycloalkyl, cyano, amino, monoalkylamino, dialkylamino, hydroxyalkyl, cycloalkylalkyl, alkoxyalkyl, aralkyl and aryl;
wherein each of $R^3$ through $R^{11}$ is independently selected from hydrido, hydroxy, alkyl, hydroxyalkyl, halo, haloalkyl, cycloalkyl, cycloalkylalkyl, alkoxy, aralkyl, aryl, aroyl, aryloxy, aralkoxy, alkoxyalkyl, alkylcarbonyl, alkoxycarbonyl, alkenyl, cycloalkenyl, alkynyl, cycloalkynyl, cyano, nitro, carboxyl, alkylcarbonyloxy, mercaptocarbonyl, mercaptothiocarbonyl, alkoxycarbonyloxy, alkylthio, alkylthiocarbonyl, alkylcarbonylthio, alkylthiocarbonyloxy, alkylthiocarbonylthio, alkylthiothiocarbonyl, arylthio, arylthiocarbonyl, arylcarbonylthio, arylthiocarbonyloxy, arylthiothiocarbonyl, aralkylthio, aralkylthiocarbonyl, aralkylcarbonylthio, aralkylthiocarbonyloxy, aralkylthiocarbonylthio, mercapto, alkylsulfonyl, aralkylsulfonyl and arylsulfonyl, and amino and amido radicals of the formula

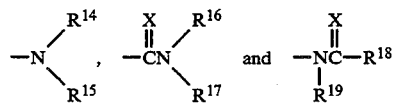

wherein X is oxygen atom or sulfur atom; wherein each of $R^{14}$, $R^{15}$, $R^{16}$, $R^{17}$, $R^{18}$ and $R^{19}$ is independently selected from hydrido, alkyl, cycloalkyl, cyano, hydroxyalkyl, cycloalkylalkyl, alkoxyalkyl, aralkyl and aryl;
and wherein each of $R^3$ through $R^{11}$ may be further independently selected from acidic moieties of the formula —$Y_nA$ wherein n is a number selected from zero through three, inclusive; wherein A is an acidic group selected from acids containing one or more atoms selected from oxygen, sulfur, phosphorus and nitrogen atoms, and wherein said acidic group is selected to contain at least one acidic hydrogen atom, and the amide, ester and salt derivatives of said acidic moieties; wherein Y is a spacer group independently selected from one or more of alkyl, cycloalkyl, cycloalkylalkyl, alkenyl, alkynyl, aryl, aralkyl and heteroaryl having one or more ring atoms selected from oxygen, sulfur and nitrogen atoms;

and wherein any of the foregoing $R^1$ through $R^{26}$, Y and A groups having a substitutable position may be substituted by one or more groups independently selected from hydroxy, alkyl, alkenyl, aralkyl, hydroxyalkyl, halo, haloalkyl, oxo, alkoxy, aryloxy, aralkoxy, alkoxyalkyl, alkylcarbonyl, alkoxycarbonyl, carboxyl, cyano, nitro, alkylsulfonyl, haloalkylsulfonyl, aryl, aralkyl, mercaptocarbonyl, alkylthio and alkylthiocarbonyl, and amino and amido radicals of the formula

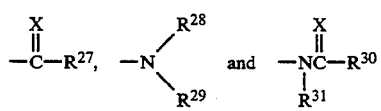

wherein X is oxygen atom or sulfur atom; wherein each of $R^{27}$ through $R^{31}$ is independently selected from hydrido, alkyl, cycloalkyl, cycloalkylalkyl, aralkyl, aryl, and $DR^{32}$ and

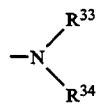

wherein D is selected from oxygen atom and sulfur atom, and $R^{32}$ is selected from hydrido, alkyl, cycloalkyl, cycloalkylalkyl, aralkyl and aryl; wherein each of $R^{27}$, $R^{28}$, $R^{29}$, $R^{30}$, $R^{31}$, $R^{33}$ and $R^{34}$ is independently selected from hydrido, alkyl, cycloalkyl, cyano, hydroxyalkyl, haloalkyl, cycloalkylalkyl, alkoxyalkyl, alkanoyl, alkoxycarbonyl, carboxyl, haloalkylsulfinyl, haloalkylsulfonyl, aralkyl and aryl;

or a tautomer thereof or a pharmaceutically-acceptable salt thereof.

A more preferred class of compounds consists of those compounds of Formula I wherein m is one; wherein $R^1$ is selected from alkyl, hydroxyalkyl, haloalkyl, cycloalkyl, cycloalkylalkyl, aralkyl, aryl, aroyl, alkoxyalkyl, alkylcarbonyl, alkoxycarbonyl, alkenyl, cycloalkenyl, alkynyl, cycloalkynyl, carboxyl, alkylsulfonyl, aralkylsulfonyl and arylsulfonyl, and amido radicals of the formula

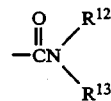

wherein each of $R^{12}$ and $R^{13}$ is independently selected from hydrido, alkyl, cycloalkyl, cyano, amino, monoalkylamino, dialkylamino, hydroxyalkyl, cycloalkylalkyl, alkoxyalkyl, aralkyl and aryl;
wherein $R^2$ is selected from hydrido, alkyl, hydroxyalkyl, halo, haloalkyl, cycloalkyl, cycloalkylalkyl, cycloalkylhaloalkyl, cycloalkylcarbonyl, alkoxy, aralkyl, aralkylhaloalkyl, aryl, aroyl, aryloxy, aryloxyalkyl, aralkoxy, alkoxyalkyl, alkylcarbonyl, alkoxycarbonyl, alkenyl, cycloalkenyl, alkynyl, cycloalkynyl, cyano, nitro, carboxyl, carboxyalkyl, alkylcarbonyloxy, mercaptocarbonyl, alkoxycarbonyloxy, alkylcarbonyloxy-
alkyl, alkoxycarbonylalkyl, aralkoxycarbonylalkyl, aralkylcarbonyloxyalkyl, alkylthio, cycloalkylthio, cycloalkylalkylthio, arylthio, aralkylthio, aralkylthiocarbonylthio, mercapto, alkylsulfinyl, alkylsulfonyl, aralkylsulfinyl, aralkylsulfonyl, arylsulfinyl, arylsulfonyl, phthalimido, phthalimidoalkyl, heteroaryl, heteroarylalkyl, cycloheteroalkyl, cycloheteroalkylalkyl and cycloheteroalklylcarbonylalkyl wherein each of said heteroaryl- and cycloheteroalkyl-containing groups has one or more hetero ring atoms selected from oxygen, sulfur and nitrogen atoms, and wherein $R^2$ may be further selected from amino and amido radicals of the formula

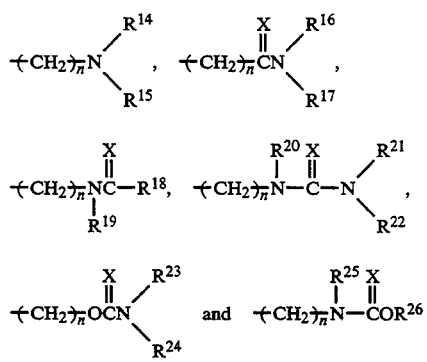

wherein X is selected from oxygen atom or sulfur atom; wherein each n is a number independently selected from zero to six, inclusive;
wherein each of $R^{14}$ through $R^{26}$ is independently selected from hydrido, alkyl, cycloalkyl, cyano, amino, monoalkylamino, dialkylamino, hydroxyalkyl, cycloalkylalkyl, alkoxyalkyl, aralkyl and aryl;
wherein each of $R^3$ through $R^{11}$ is independently selected from hydrido, hydroxy, alkyl, hydroxyalkyl, halo, haloalkyl, cycloalkyl, alkoxy, aralkyl, aryl, aroyl, aryloxy, aralkoxy, alkoxyalkyl, alkylcarbonyl, alkoxycarbonyl, alkenyl, cycloalkenyl, alkynyl, cyano, nitro, carboxyl, alkylcarbonyloxy, mercaptocarbonyl, alkoxycarbonyloxy, alkylthio, arylthio, aralkylthio, mercapto, alkylsulfonyl, aralkylsulfonyl and arylsulfonyl, and amino and amido radicals of the formula

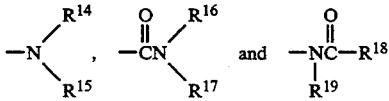

wherein each of $R^{14}$, $R^{15}$, $R^{16}$, $R^{17}$, $R^{18}$ and $R^{19}$ is independently selected from hydrido, alkyl, cycloalkyl, cyano, amino, monoalkylamino, dialkylamino, hydroxyalkyl, cycloalkylalkyl, alkoxyalkyl, aralkyl and aryl;
and wherein each of $R^3$ through $R^{11}$ may be further independently selected from acidic moieties of the formula —$Y_nA$ wherein n is a number selected from zero through three, inclusive;
wherein the A group is selected to have an acidic proton, such that when the —$Y_nA$ moiety is incorporated within a compound of Formula I, there is provided a compound of Formula I having a p$K_a$ in a range from about two to about seven, said A group selected from carboxylic acid and bioisosteres of carboxylic acid selected from

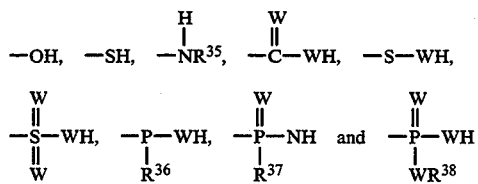

wherein each W is independently selected from oxygen atom, sulfur atom and $NR^{39}$; wherein each of $R^{35}$, $R^{36}$, $R^{37}$, $R^{38}$ and $R^{39}$ is independently selected from hydrido, alkyl, haloalkyl, haloalkylsulfonyl, haloalkylcarbonyl, cycloalkyl, cycloalkylalkyl, aryl and aralkyl; wherein each of $R^{35}$, $R^{36}$, $R^{37}$ and $R^{39}$ may be further independently selected from amino radical of the formula

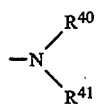

wherein each of $R^{40}$ and $R^{41}$ is independently selected from hydrido, alkyl, cycloalkyl, hydroxyalkyl, haloalkyl, cycloalkylalkyl, alkoxyalkyl, aralkyl and aryl, and wherein $R^{40}$ and $R^{41}$ taken together may form a heterocyclic group having five to seven ring members including the nitrogen atom of said amino radical, which heterocyclic group may further contain one or more hetero atoms as ring members selected from oxygen, nitrogen and sulfur atoms and which heterocyclic group may be saturated or partially unsaturated; wherein $R^{40}$ and $R^{41}$ taken together may form an aromatic heterocyclic group having five ring members including the nitrogen atom of said amino radical and which aromatic heterocyclic group may further contain one or more hetero atoms as ring atoms selected from oxygen, nitrogen and sulfur atoms; wherein each of $R^{36}$ and $R^{37}$ may be further independently selected from hydroxy, alkoxy, alkylthio, aryloxy, arylthio, aralkylthio and aralkoxy; and the amide, ester and salt derivatives of said acidic groups;

wherein said bioisostere of carboxylic acid may be further selected from heterocyclic acidic groups consisting of heterocyclic rings of four to about nine ring members, which heterocyclic ring contains at least one hetero atom selected from oxygen, sulfur and nitrogen atoms, which heterocyclic ring may be saturated, fully unsaturated or partially unsaturated, and which heterocyclic ring may be attached at a single position selected from $R^3$ through $R^{11}$ or may be attached at any two adjacent positions selected from $R^3$ through $R^{11}$ so as to form a fused-ring system with one of the phenyl rings of Formula I; and the amide, ester and salt derivatives of said heterocyclic acidic groups;

wherein Y is a spacer group independently selected from one or more of alkyl, cycloalkyl, cycloalkylalkyl, alkenyl, aryl and aralkyl;

and wherein any of the foregoing $R^1$ through $R^{26}$ and $R^{35}$ through $R^{41}$, Y and A groups having a substitutable position may be substituted by one or more groups independently selected from hydroxy, alkyl, alkenyl, aralkyl, hydroxyalkyl, halo, oxo, haloalkyl, alkoxy, aryloxy, aralkoxy, alkoxyalkyl, alkylcarbonyl, alkoxycarbonyl, carboxyl, cyano, nitro, alkylsulfonyl, haloalkylsulfonyl, aryl, aralkyl, mercaptocarbonyl, alkylthio and alkylthiocarbonyl, and amino and amido radicals of the formula

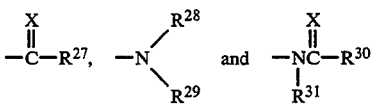

wherein X is selected from oxygen atom and sulfur atom; wherein $R^{27}$ is selected from hydrido, alkyl, cycloalkyl, cycloalkylalkyl, aralkyl, aryl and $DR^{32}$ and

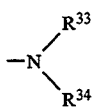

wherein D is selected from oxygen atom and sulfur atom; wherein $R^{32}$ is selected from hydrido, alkyl, cycloalkyl, cycloalkylalkyl, aralkyl and aryl; wherein each of $R^{27}$, $R^{28}$, $R^{29}$, $R^{30}$, $R^{31}$, $R^{33}$ and $R^{34}$ is independently selected from hydrido, alkyl, cycloalkyl, cyano, hydroxyalkyl, haloalkyl, cycloalkylalkyl, alkoxyalkyl, alkanoyl, alkoxycarbonyl, carboxyl, haloalkylsulfinyl, haloalkylsulfonyl, aralkyl and aryl;

or a tautomer thereof or a pharmaceutically-acceptable salt thereof.

An even more preferred class of compounds consists of those compounds of Formula I wherein m is one; wherein $R^1$ is selected from hydrido, alkyl, hydroxyalkyl, haloalkyl, cycloalkyl, cycloalkylalkyl, aralkyl, aryl, aroyl, alkoxyalkyl, alkylcarbonyl, alkenyl, cycloalkenyl, alkynyl, mercaptocarbonyl, alkylsulfonyl, aralkylsulfonyl, arylsulfonyl and amido radicals of the formula

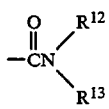

wherein each of $R^{12}$ and $R^{13}$ is independently selected from hydrido, alkyl, cycloalkyl, cyano, amino, monoalkylamino, dialkylamino, hydroxyalkyl, cycloalkylalkyl, alkoxyalkyl, aralkyl and aryl;

wherein $R^2$ is selected from hydrido, alkyl, hydroxyalkyl, halo, haloalkyl, cycloalkyl, cycloalkylalkyl, cycloalkylhaloalkyl, cycloalkylcarbonyl, alkoxy, aralkyl, aralkylhaloalkyl, aryl, aroyl, aryloxy, aryloxyalkyl, aralkoxy, alkoxyalkyl, alkylcarbonyl, alkoxycarbonyl, alkenyl, cycloalkenyl, alkynyl, cycloalkynyl, cyano, nitro, carboxyl, carboxyalkyl, alkylcarbonyloxy, alkylcarbonyloxyalkyl, alkoxycarbonylalkyl, aralkoxycarbonylalkyl, aralkylcarbonyloxyalkyl, mercaptocarbonyl, mercaptoalkyl, alkoxycarbonyloxy, alkylthio, cycloalkylthio, cycloalkylalkylthio, arylthio, aralkylthio, mercapto, alkylsulfinyl, alkylsulfonyl, aralkylsulfinyl, aralkylsulfonyl, arylsulfinyl, arylsulfonyl, phthalimido, phthalimidoalkyl, heteroaryl, heteroarylalkyl, cycloheteroalkyl, cycloheteroalkylalkyl and cycloheteroalkylcarbonylalkyl wherein each of said heteroaryl- and cycloheteroalkyl-containing groups has one or more hetero ring atoms selected from oxygen, sulfur and nitrogen atoms, and wherein each of $R^2$ through R[11] may be further independently selected from amino and amido radicals of the formula

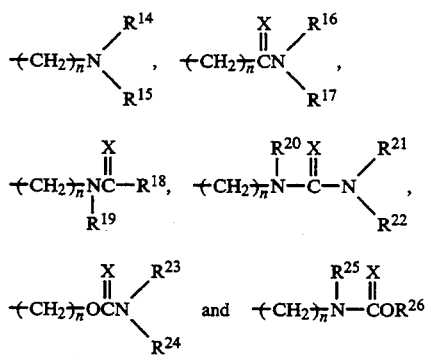

wherein X is selected from oxygen atom and sulfur atom;
wherein each n is a number independently selected from zero to six, inclusive;
wherein each of R[14] through R[26] is independently selected from hydrido, alkyl, cycloalkyl, cyano, amino, monoalkylamino, dialkylamino, hydroxyalkyl, cycloalkylalkyl, alkoxyalkyl, aralkyl and aryl;
wherein each of R[3] through R[11] is independently selected from hydrido, hydroxy, alkyl, hydroxyalkyl, halo, haloalkyl, cycloalkyl, alkoxy, aralkyl, aryl, aroyl, aryloxy, aralkoxy, alkoxyalkyl, alkylcarbonyl, alkoxycarbonyl, alkenyl, cycloalkenyl, alkynyl, cyano, nitro, carboxyl, alkylthio, aralkylthio and mercapto;
and wherein each of R[3] through R[11] may be further independently selected from acidic moieties of the formula —Y$_n$A wherein n is a number selected from zero through three, inclusive; wherein A is selected from carboxylic acid and bioisosteres of carboxylic acid selected from

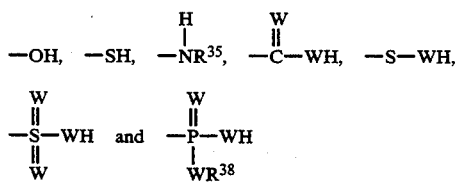

wherein each W is independently selected from oxygen atom, sulfur atom and NR[39]; wherein each of R[35], R[38] and R[39] is independently selected from hydrido, alkyl, haloalkyl, haloalkylsulfonyl, haloalkylcarbonyl, cycloalkyl, cycloalkylalkyl, aryl and aralkyl; wherein each of R[35] and R[39] may be further independently selected from amino radical of the formula

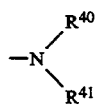

wherein each of R[40] and R[41] is independently selected from hydrido, alkyl, cycloalkyl, hydroxyalkyl, haloalkyl, cycloalkylalkyl, alkoxyalkyl, aralkyl and aryl, and wherein R[40] and R[41] taken together may form a heterocyclic group having five to seven ring members including the nitrogen atom of said amino radical, which heterocyclic group may further contain one or more hetero atoms as ring members selected from oxygen, nitrogen and sulfur atoms, and which heterocyclic group may be saturated or partially unsaturated; wherein R[40] and R[41] taken together may form an aromatic heterocyclic group having five ring members including the nitrogen atom of said amino radical and which aromatic heterocyclic group may further contain one or more hetero atoms as ring atoms selected from oxygen, nitrogen and sulfur atoms; and the amide, ester and salt derivatives of said acidic groups; wherein said bioisostere of carboxylic acid may be further selected from heterocyclic acidic groups consisting of heterocyclic rings of four to about nine ring members, which ring contains at least one hetero atom, selected from oxygen, sulfur and nitrogen atoms, which heterocyclic ring may be saturated, fully unsaturated or partially unsaturated, and which heterocyclic ring may be attached at a single position selected from R[3] through R[11] or may be attached at any two adjacent positions selected from R[3] through R[11] so as to form a fused-ring system with one of the phenyl rings of Formula I; and the amide, ester and salt derivatives of said heterocyclic acidic groups;
wherein Y is a spacer group independently selected from one or more of alkyl, cycloalkyl, cycloalkylalkyl, alkenyl, aryl and aralkyl;
wherein each of R[1] through R[26], R[35] and R[38] through R[41], Y and A independently may be substituted at any substitutable position with one or more groups selected from alkyl, hydroxy, halo, oxo, haloalkyl, alkoxycarbonyl, cyano, nitro, alkylsulfonyl, haloalkylsulfonyl, aryl, aralkyl, alkoxy, aryloxy and aralkoxy;
or a tautomer thereof or a pharmaceutically-acceptable salt thereof.

A highly preferred class of compounds within Formula I consists of those compounds wherein m is one; wherein R[1] is selected from hydrido, alkyl, hydroxyalkyl, haloalkyl, cycloalkyl, cycloalkylalkyl, aralkyl, aryl, aroyl, alkoxyalkyl, alkylcarbonyl, alkenyl, alkynyl, alkylsulfonyl, aralkylsulfonyl, arylsulfonyl and amido radicals of the formula

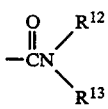

wherein each of R[12] and R[13] is independently selected from hydrido, alkyl, cycloalkyl, cyano, amino, hydroxyalkyl, alkoxyalkyl, phenalkyl and phenyl;
wherein R[2] is selected from hydrido, alkyl, hydroxyalkyl, halo, haloalkyl, cycloalkyl, cycloalkylalkyl, cycloalkylhaloalkyl, cycloalkylcarbonyl, alkoxy, aralkyl, aralkylhaloalkyl, aryl, benzoyl, phenoxy, phenoxyalkyl, phenalkyloxy, phenylthio, phenalkylthio, aralkoxy, alkoxyalkyl, alkylcarbonyl, alkoxycarbonyl, alkenyl, cycloalkenyl, alkynyl, cyano, nitro, carboxyl, carboxyalkyl, alkylcarbonyloxy, alkylcarbonyloxyalkyl, alkoxycarbonylalkyl, aralkoxycarbonylalkyl, aralkylcarbonyloxyalkyl, mercaptocarbonyl, mercaptoalkyl, alkoxycarbonyloxy, alkylthio, cycloalkylthio, cycloalkylalkylthio, phthalimido, phthalimidoalkyl, heteroaryl, heteroarylalkyl, cycloheteroalkyl, cycloheteroalkylalkyl and cycloheteroalkylcarbonylalkyl wherein each of said heteroaryl- and cycloheteroalkyl-containing groups has one or more hetero ring atoms selected from oxygen, sulfur and nitrogen atoms, and wherein each of R² through R¹¹ may be further independently selected from amino and amido radicals of the formula

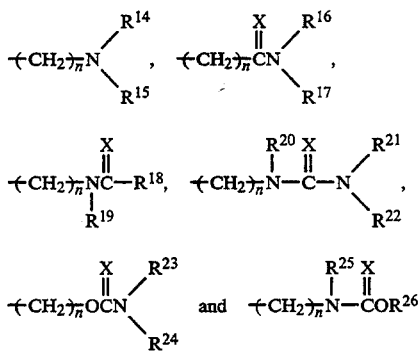

wherein X is selected from oxygen atom and sulfur atom;
wherein each n is a number independently selected from zero to six, inclusive;
wherein each of R¹⁴ through R²⁶ is independently selected from hydrido, alkyl, cycloalkyl, cyano, amino, hydroxyalkyl, alkoxyalkyl, phenalkyl and phenyl;
wherein each of R³ through R¹¹ is independently selected from hydrido, hydroxy, alkyl, hydroxyalkyl, halo, haloalkyl, cycloalkyl, alkoxy, phenalkyl, phenyl, benzoyl, phenoxy, phenalkyloxy, alkoxyalkyl, alkylcarbonyl, alkoxycarbonyl, alkenyl, cyano, nitro, carboxyl, alkylthio and mercapto;
and wherein each of R³ through R¹¹ may be further independently selected from acidic moieties of the formula —Y$_n$A wherein n is a number selected from zero through two, inclusive; wherein A is selected from carboxylic acid and bioisosteres of carboxylic acid selected from

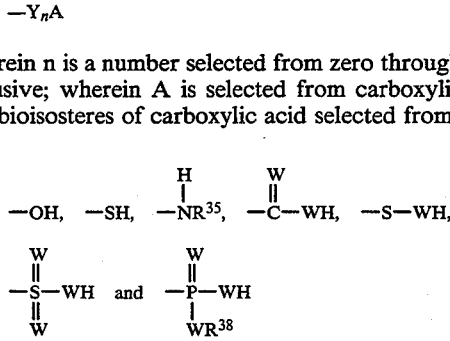

wherein each W is independently selected from oxygen atom, sulfur atom and NR³⁹; wherein each of R³⁵, R³⁸ and R³⁹ is independently selected from hydrido, alkyl, haloalkyl, haloalkylsulfonyl, haloalkylcarbonyl, cycloalkyl, phenyl and benzyl; wherein each of R³⁵ and R³⁹ may be further independently selected from amino radical of the formula

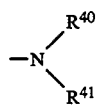

wherein each of R⁴⁰ and R⁴¹ is independently selected from hydrido, alkyl, cycloalkyl, hydroxyalkyl, haloalkyl, alkoxyalkyl, benzyl and phenyl; and the amide, ester and salt derivatives of said acidic groups;
wherein said bioisostere of carboxylic acid may be further selected from heterocyclic acidic groups consisting of heterocyclic rings of four to about nine ring members, which ring contains at least one hetero atom, selected from oxygen, sulfur and nitrogen atoms, which heterocyclic ring may be saturated, fully unsaturated or partially unsaturated, and which heterocyclic ring may be attached at a single position selected from R³ through R¹¹ or may be attached at any two adjacent positions selected from R³ through R¹¹ so as to form a fused-ring system with one of the phenyl rings of Formula I; and the amide, ester and salt derivatives of said heterocyclic acidic groups;
wherein Y is a spacer group independently selected from one or more of alkyl, cycloalkyl, cycloalkylalkyl, alkenyl, phenyl, phenalkyl and aralkyl;
wherein each of R¹ through R²⁶, R³⁵ and R³⁸ through R⁴¹, Y and A and independently may be substituted at any substitutable position with one or more groups selected from alkyl, cycloalkyl, cycloalkylalkyl, hydroxy, halo, oxo, haloalkyl, alkoxycarbonyl, cyano, nitro, alkylsulfonyl, haloalkylsulfonyl, aryl, aralkyl, alkoxy, aryloxy and aralkoxy;
or a tautomer thereof or a pharmaceutically-acceptable salt thereof.

An even more highly preferred class of compounds consists of those compounds of Formula I wherein m is one; wherein R¹ is selected from hydrido, alkyl, hydroxyalkyl, haloalkyl, cycloalkyl, cycloalkylalkyl, aralkyl, aryl, benzoyl, alkoxyalkyl, alkylcarbonyl, alkoxycarbonyl, alkenyl and alkynyl;
where R² is selected from alkyl, aminoalkyl, hydroxyalkyl, halo, haloalkyl, cycloalkyl, cycloalkylalkyl, alkylcarbonyl, cycloalkylhaloalkyl, cycloalkylcarbonyl, alkoxy, aralkyl, aralkylhaloalkyl, aryl, benzoyl, phenoxy, phenoxyalkyl, phenalkyloxy, phenylthio, phenalkylthio, aralkoxy, alkoxyalkyl, acetyl, alkoxycarbonyl, alkenyl, cycloalkenyl, alkynyl, cyano, nitro, carboxyl, carboxyalkyl, alkylcarbonyloxy, mercaptoalkyl, mercaptocarbonyl, alkoxycarbonyloxy, alkylcarbonyloxyalkyl, alkoxycarbonylalkyl, aralkoxycarbonylalkyl, aralkylcarbonyloxyalkyl, phthalimido, phthalimidoalkyl, imidazoalkyl, tetrazole, tetrazolealkyl, alkylthio, cycloalkylthio, cycloalkylalkylthio, and amino and amido radicals of the formula

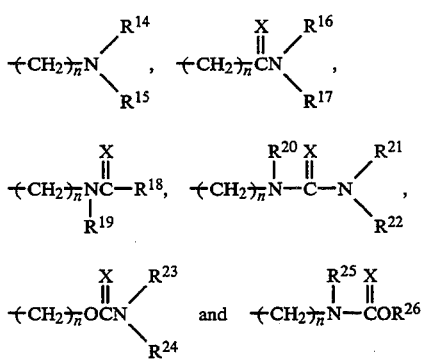

wherein X is selected from oxygen atom and sulfur atom;
wherein each n is a number independently selected from zero to six, inclusive;
wherein each of R¹⁴ through R²⁶ is independently selected from hydrido, alkyl, cycloalkyl, cyano, amino, hydroxyalkyl, alkoxyalkyl, phenalkyl and phenyl;
wherein each of R³ through R¹¹ is independently selected from hydrido, hydroxy, alkyl, hydroxyalkyl, halo, haloalkyl, alkoxy, phenyl, benzoyl, phenoxy, alkoxyalkyl, acetyl, alkoxycarbonyl, alkenyl, cyano, nitro, carboxyl, alkylthio and mercapto;

and wherein each of $R^3$ through $R^{11}$ may be further independently selected from acidic moieties consisting of $CO_2H$, $CO_2CH_3$, SH, $CH_2SH$, $C_2H_4SH$, $PO_3H_2$, $NHSO_2CF_3$, $NHSO_2C_6F_5$, $SO_3H$, $CONHNH_2$, $CONHNHSO_2CF_3$, $CONHOCH_3$, $CONHOC_2H_5$, $CONHCF_3$, OH, $CH_2OH$, $C_2H_4OH$, $OPO_3H_2$, $OSO_3H$,

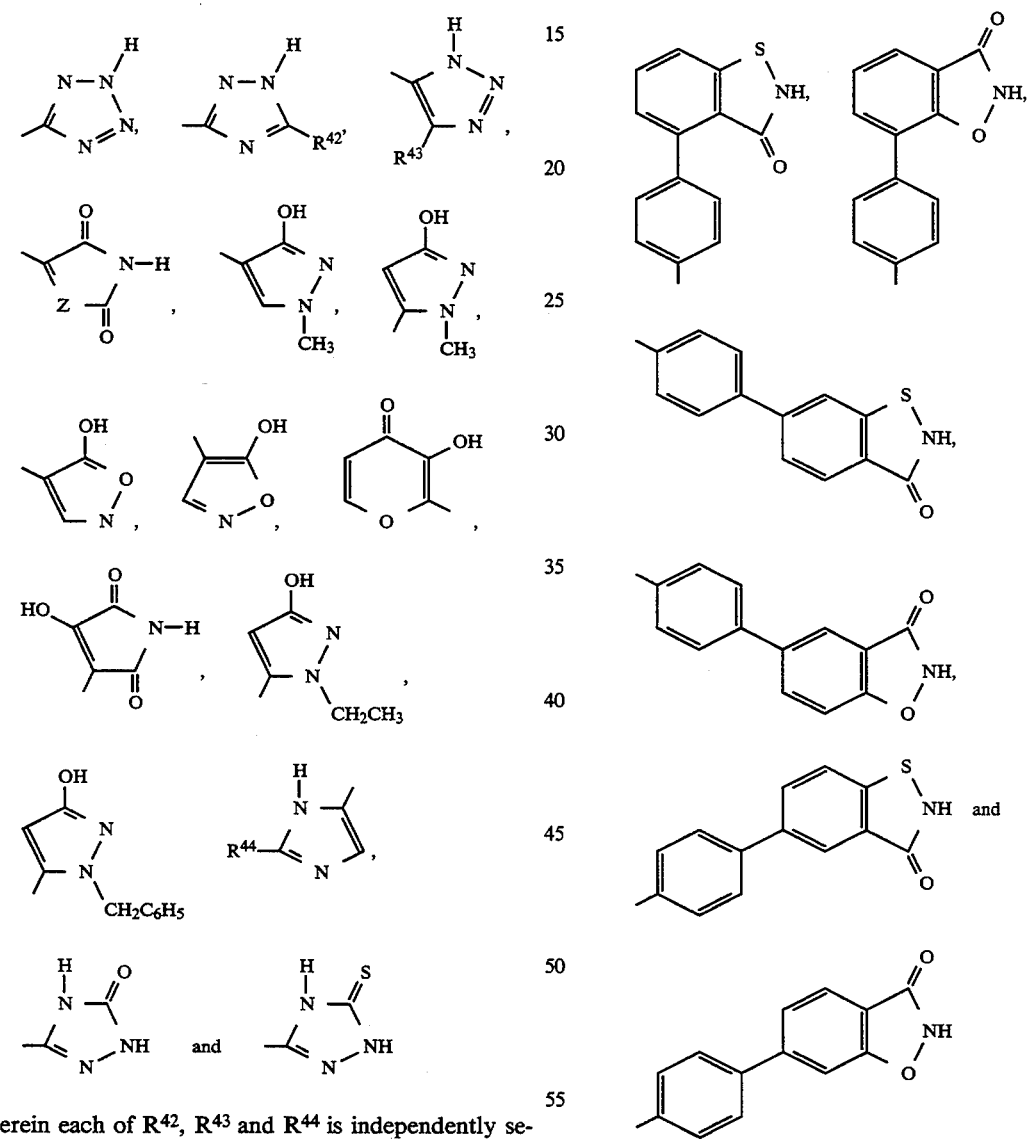

wherein each of $R^{42}$, $R^{43}$ and $R^{44}$ is independently selected from H, Cl, CN, $NO_2$, $CF_3$, $C_2F_5$, $C_3F_7$, $CHF_2$, $CH_2F$, $CO_2CH_3$, $CO_2C_2H_5$, $SO_2CH_3$, $SO_2CF_3$ and $SO_2C_6F_5$; wherein Z is selected from O, S, $NR^{45}$ and $CH_2$; wherein $R^{45}$ is selected from hydrido, $CH_3$ and $CH_2C_6H_5$; and wherein said acidic moiety may be a heterocyclic acidic group attached at any two adjacent positions of $R^3$ through $R^{11}$ so as to form a fused ring system with one of the phenyl rings of the biphenyl moiety of Formula I, said biphenyl fused ring system selected from

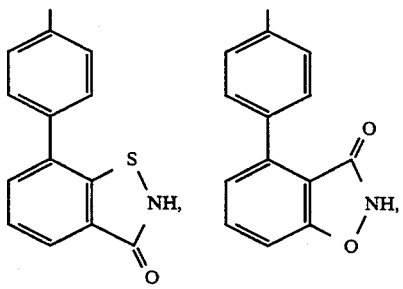

and the esters, amides and salts of said acidic moieties; or a tautomer thereof or a pharmaceutically-acceptable salt thereof.

A class of compounds of particular interest consists of those compounds of Formula I wherein m is one; wherein $R^1$ is selected from methyl, ethyl, n-propyl, isopropyl, n-butyl, sec-butyl, isobutyl, tert-butyl, n-pentyl, isopentyl, neopentyl, phenyl, benzyl, phenethyl, cyclohexyl, cyclohexylmethyl, 2-butenyl, 3-butenyl, 2-butynyl, 3-butynyl and 2-hydroxybutyl; wherein $R^2$ is selected from C₄H₉(n), CH₃CH₂CH=CH, C₃H₇(n), SC₃H₇,

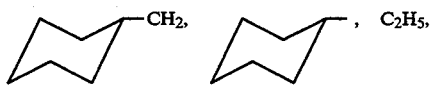

C₅H₁₁(n), C₆H₁₃(n), SC₄H₉, 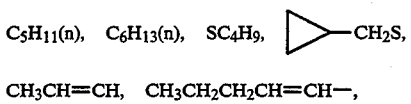

CH₃CH=CH, CH₃CH₂CH₂CH=CH—, amino, aminomethyl, aminoethyl, aminopropyl, acetyl, CH₂OH, CH₂OCOCH₃, CH₂Cl, Cl, CH₂OCH₃, CH₂OCH(CH₃)₂, I, CHO, CH₂CO₂H, CH(CH₃)CO₂H, NO₂, Cl,

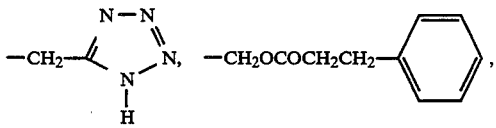

—CO₂CH₃, —CONH₂, —CONHCH₃, CON(CH₃)₂,

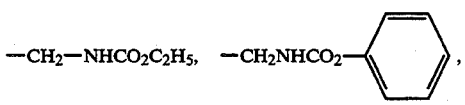

—CH₂NHCO₂CH₃, —CH₂NHCO₂C₃H₇,

—CH₂NHCO₂CH₂(CH₃)₂, —CH₂NHCO₂C₄H₉, CH₂NHCO₂-adamantyl, —CH₂NHCO₂-(1-napthyl), —CH₂NHCONHCH₃, —CH₂NHCONHC₂H₅, —CH₂NHCONHC₃H₇, —CH₂NHCONHC₄H₉, —CH₂NHCONHCH(CH₃)₂, —CH₂NHCONH(1-napthyl), —CH₂NHCONH(1-adamantyl), CO₂H,

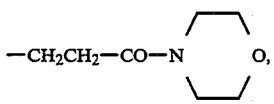

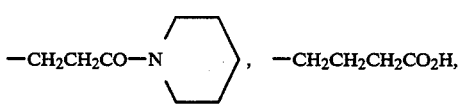

—CH₂CH₂F, —CH₂OCONHCH₃, —CH₂OCSNHCH₃,
—CH₂NHCSOC₃H₇, —CH₂CH₂CH₂F, —CH₂ONO₂,

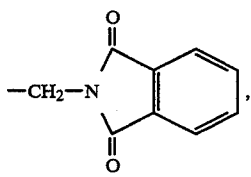

—CH₂SH, 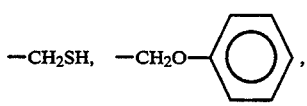

H, Cl, NO₂, CF₃, CH₂OH, Br, F, I, methyl, ethyl, n-propyl, isopropyl, n-butyl, sec-butyl, isobutyl, tert-butyl, n-pentyl, isopentyl, neopentyl, phenyl, cyclohexyl, cyclohexylmethyl, 1-oxoethyl, 1-oxopropyl, 1-oxobutyl, 1-oxopentyl, 1,1-dimethoxypropyl, 1,1-dimethoxypentyl, hydroxyalkyl, halo, 1-oxo-2-phenylethyl, 1-oxo-2-cyclohexylethyl, 1,1-difluoro-2-phenylethyl, 1,1-difluoro-2-cyclohexylethyl, 2-cyclohexylethyl, 1,1-difluoro-3-cyclohexylpropyl, 1,1-dimethoxybutyl, 1,1-difluoroethyl, 1,1-difluoropropyl, 1,1-difluorobutyl, 1,1-difluoropentyl, benzyl, 2-phenylethyl, 1,1-difluoro-3-phenylpropyl, cyclohexylmethyl, cyclohexanoyl, 1-butenyl, 2-butenyl, 3-butenyl, 1-butynyl, 2-butynyl, 3-butynyl and difluoromethyl; wherein each of $R^3$ through $R^{11}$ is hydrido with the proviso that at least one of $R^5$, $R^6$, $R^8$ and $R^9$ is an acidic group selected from CO₂H, SH, PO₃H₂, SO₃H, CONHNH₂, CONHNHSO₂CF₃, OH,

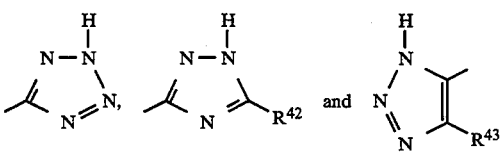

wherein each of $R^{42}$ and $R^{43}$ is independently selected from chloro, cyano, nitro, trifluoromethyl, methoxycarbonyl and trifluoromethylsulfonyl;

or a tautomer thereof or a pharmaceutically-acceptable salt thereof.

A class of compounds of more particular interest consists of those compounds of Formula I wherein m is one; wherein $R^1$ is selected from methyl, ethyl, n-propyl, isopropyl, n-butyl, sec-butyl, isobutyl, tert-butyl, 4-methylbutyl, n-pentyl, neopentyl, phenyl, benzyl, phenethyl, cyclohexyl, cyclohexylmethyl, 2-butenyl, 3-butenyl, 2-butynyl, 3-butynyl and 2-hydroxybutyl; wherein $R^2$ is selected from ethyl, n-propyl, isopropyl, n-butyl, sec-butyl, isobutyl, 4-methylbutyl, tert-butyl, n-pentyl, neopentyl, 1-oxoethyl, 1-oxopropyl, 1-oxobutyl, 1-oxopentyl 1-oxo-2-phenylethyl, 1-oxo-2-cyclohexylethyl, 1,1-difluoro-2-phenylethyl, 1,1-difluoro-2-cyclohexylethyl, 2-cyclohexylethyl, 1,1-difluoro-3-cyclohexylpropyl, 1,1-dimethoxybutyl, 1,1-difluoroethyl, 1,1-difluoropropyl, 1,1-difluorobutyl, 1,1-difluoropentyl, benzyl, 2-phenylethyl, 1,1-difluoro-3-phenylpropyl, cyclohexylmethyl, cyclohexanoyl, acetyl, 1-butenyl, 2-butenyl, 3-butenyl, 1-butynyl, 2-butynyl, 3-butynyl, propylthio and butylthio; wherein each of $R^3$ through $R^{11}$ is hydrido with the proviso that at least one of $R^5$, $R^6$, $R^8$ and $R^9$ is an acidic group selected from CO₂H, SH, PO₃H₂, SO₃H, CONHNH₂, CONHNHSO₂CF₃, OH,

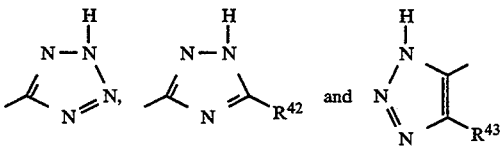

wherein each of $R^{42}$ and $R^{43}$ is independently selected from chloro, cyano, nitro, trifluoromethyl, methoxycarbonyl and trifluoromethylsulfonyl;

or a tautomer thereof or a pharmaceutically-acceptable salt thereof.

A subclass of compounds of Formula I which is of even more particular interest consists of those compounds of Formula II

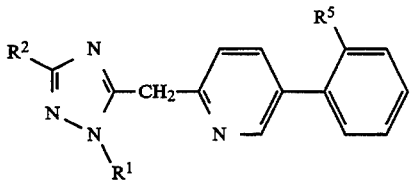 (II)

wherein m is one; wherein $R^1$ is selected from methyl, ethyl, n-propyl, isopropyl, n-butyl, sec-butyl, isobutyl, tert-butyl, 4-methylbutyl, n-pentyl, neopentyl, phenyl, benzyl, phenethyl, cyclohexyl, cyclohexylmethyl, 2-butenyl, 3-butenyl, 2-butynyl, 3-butynyl and 2-hydroxybutyl; wherein $R^2$ is selected from ethyl, n-propyl, isopropyl, n-butyl, sec-butyl, isobutyl, 4-methylbutyl, n-pentyl, 1-oxo-2-phenylethyl, 1-oxo-2-cyclohexylethyl, 1,1-difluoro-2-phenylethyl, 1,1-difluoro-2-cyclohexylethyl, 2-cyclohexylethyl, 1,1-difluoro-3-cyclohexylpropyl, 1-dimethoxybutyl, 1,1-difluoroethyl, 1,1-difluoropropyl, 1,1-difluorobutyl, 1,1-difluoropentyl, benzyl, 2-phenylethyl, 1,1-difluoro-3-phenylpropyl, cyclohexylmethyl, cyclohexanoyl, 1-butenyl, 2-butenyl, 3-butenyl, 1-butynyl, 2-butynyl, 3-butynyl, propylthio and butylthio; wherein $R^5$ is an acidic group selected from $CO_2H$ and

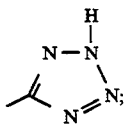

or a tautomer thereof or a pharmaceutically-acceptable salt thereof.

A family of specific compounds of particular interest within Formula II consists of the following compounds:

2-[6-[(1-propyl-3-methyl-1H-1,2,4-triazol-5-yl) methyl]-3-pyridinyl]benzoic acid;
2-[6-[(1-propyl-3-ethyl-1H-1,2,4-triazol-5-yl)methyl]-3-pyridinyl]benzoic acid;
2-[6-[(1,3-dipropyl-1H-1,2,4-triazol-5-yl) methyl]-3-pyridinyl]benzoic acid;
2-[6-[(1-propyl-3-isopropyl-1H-1,2,4-triazol-5-yl)methyl]-3-pyridinyl]benzoic acid;
2-[6-[(1-propyl-3-butyl-1H-1,2,4-triazol-5-yl)methyl]-3-pyridinyl]benzoic acid;
2-[6-[(1-propyl-3-secbutyl-1H-1,2,4-triazol-5-yl)methyl]-3-pyridinyl]benzoic acid;
2-[6-[(1-propyl-3-isobutyl-1H-1,2,4-triazol-5-yl)methyl]-3-pyridinyl]benzoic acid;
2-[6-[(1-propyl-3-tertbutyl-1H-1,2,4-triazol-5-yl)methyl]-3-pyridinyl]benzoic acid;
2-[6-[(1-propyl-3-pentyl-1H-1,2,4-triazol-5-yl)methyl]-3-pyridinyl]benzoic acid;
2-[6-[(1-propyl-3-isopentyl-1H-1,2,4-triazol-5-yl)methyl]-3-pyridinyl]benzoic acid;
2-[6-[(1-propyl-3-cyclohexyl-1H-1,2,4-triazol-5yl)methyl]-3-pyridinyl]benzoic acid;
2-[6-[(1-propyl-3-cyclohexylmethyl-1H-1,2,4-triazol-5-yl)methyl]-3-pyridinyl]benzoic acid;
2-[6-[[1-propyl-3-(2-cyclohexylethyl)-1H-1,2,4-triazol-5-yl]methyl]-3-pyridinyl]benzoic acid;
2-[6-[(1-propyl-3-phenyl-1H-1,2,4-triazol-5-yl)methyl]-3-pyridinyl]benzoic acid;
2-[6-[(1-propyl-3-phenylmethyl-1H-1,2,4-triazol-5-yl)methyl]-3-pyridinyl]benzoic acid;
2-[6-[[1-propyl-3-(2-phenylethyl)-1H-1,2,4-triazol-5-yl]methyl]-3-pyridinyl]benzoic acid;
2-[6-[(1-propyl-3-cyclohexanoyl-1H-1,2,4-triazol-5-yl)methyl]-3-pyridinyl]benzoic acid;
2-[6-[[1-propyl-3-(1-oxo-2-cyclohexylethyl)-1H-1,2,4-triazol-5-yl]methyl]-3-pyridinyl]benzoic acid;
2-[6-[(1-propyl-3-benzoyl-1H-1,2,4-triazol-5-yl)methyl]-3-pyridinyl]benzoic acid;
2-[6-[[1-propyl-3-(1-oxo-2-phenylethyl)-1H-1,2,4-triazol-5-yl]methyl]-3-pyridinyl]benzoic acid;
2-[6-[[1-propyl-3-(1,1-dimethoxypropyl)-1H-1,2,4-triazol-5-yl]methyl]-3-pyridinyl]benzoic acid;
2-[6-[[1-propyl-3-(1,1-dimethoxybutyl)-1H-1,2,4-triazol-5-yl]methyl]-3-pyridinyl]benzoic acid;
2-[6-[[1-propyl-3-(1,1-dimethoxypentyl)-1H-1,2,4-triazol-5-yl]methyl]-3-pyridinyl]benzoic acid;
2-[6-[[1-propyl-3-(1-oxopropyl)-1H-1,2,4-triazol-5-yl]methyl]-3-pyridinyl]benzoic acid;
2-[6-[[1-propyl-3-(1-oxobutyl)-1H-1,2,4-triazol-5-yl]methyl]-3-pyridinyl]benzoic acid;
2-[6-[[1-propyl-3-(1-oxopentyl)-1H-1,2,4-triazol-5-yl]methyl]-3-pyridinyl]benzoic acid;
2-[6-[[1-propyl-3-(1,1-difluorobutyl)-1H-1,2,4-triazol-5-yl]methyl]-3-pyridinyl]benzoic acid;
2-[6-[(1-butyl-3-methyl-1H-1,2,4-triazol-5-yl)methyl]-3-pyridinyl]benzoic acid;
2-[6-[(1-butyl-3-ethyl-1H-1,2,4-triazol-5-yl)methyl]-3-pyridinyl]benzoic acid;
2-[6-[(1-butyl-3-propyl-1H-1,2,4-triazol-5-yl)methyl]-3-pyridinyl]benzoic acid;
2-[6-[(1-butyl-3-isopropyl-1H-1,2,4-triazol-5-yl)methyl]-3-pyridinyl]benzoic acid;
2-[6-[(1,3-dibutyl-1H-1,2,4-triazol-5-yl)methyl]-3-pyridinyl]benzoic acid;
2-[6-[(1-butyl-3-secbutyl-1H-1,2,4-triazol-5-yl)methyl]-3-pyridinyl]benzoic acid;
2-[6-[(1-butyl-3-isobutyl-1H-1,2,4-triazol-5-yl)methyl]-3-pyridinyl]benzoic acid;
2-[6-[(1-butyl-3-tertbutyl-1H-1,2,4-triazol-5-yl)methyl]-3-pyridinyl]benzoic acid;
2-[6-[(1-butyl-3-pentyl-1H-1,2,4-triazol-5-yl)methyl]-3-pyridinyl]benzoic acid;
2-[6-[(1-butyl-3-isopentyl-1H-1,2,4-triazol-5-yl)methyl]-3-pyridinyl]benzoic acid;
2-[6-[(1-butyl-3-cyclohexyl-1H-1,2,4-triazol-5-yl)methyl]-3-pyridinyl]benzoic acid;
2-[6-[(1-butyl-3-cyclohexylmethyl-1H-1,2,4-triazol-5-yl)methyl]-3-pyridinyl]benzoic acid;
2-[6-[[1-butyl-3-(2-cyclohexylethyl)-1H-1,2,4-triazol-5-yl]methyl]-3-pyridinyl]benzoic acid;
2-[6-[(1-butyl-3-phenyl-1H-1,2,4-triazol-5-yl)methyl]-3-pyridinyl]benzoic acid;
2-[6-[(1-butyl-3-phenylmethyl-1H-1,2,4-triazol-5-yl)methyl]-3-pyridinyl]benzoic acid;
2-[6-[[1-butyl-3-(2-phenylethyl)-1H-1,2,4-triazol-5-yl]methyl]-3-pyridinyl]benzoic acid;
2-[6-[(1-butyl-3-cyclohexanoyl-1H-1,2,4-triazol-5-yl)methyl]-3-pyridinyl]benzoic acid;
2-[6-[[1-butyl-3-(1-oxo-2-cyclohexylethyl)-1H-1,2,4-triazol-5-yl]methyl]-3-pyridinyl]benzoic acid;
2-[6-[(1-butyl-3-benzoyl-1H-1,2,4-triazol-5-yl)methyl]-3-pyridinyl]benzoic acid;
2-[6-[[1-butyl-3-(1-oxo-2-phenylethyl)-1H-1,2,4-triazol-5-yl]methyl]-3-pyridinyl]benzoic acid;
2-[6-[[1-butyl-3-(1,1-dimethoxypropyl)-1H-1,2,4-triazol-5-yl]methyl]-3-pyridinyl]benzoic acid;
2-[6-[[1-butyl-3-(1,1-dimethoxybutyl)-1H-1,2,4-triazol-5-yl]methyl]-3-pyridinyl]benzoic acid;

2-[6-[[1-butyl-3-(1,1-dimethoxypentyl)-1H-1,2,4-triazol-5-yl]methyl]-3-pyridinyl]benzoic acid;
2-[6-[[1-butyl-3-(1-oxopropyl)-1H-1,2,4-triazol-5-yl]methyl]-3-pyridinyl]benzoic acid;
2-[6-[[1-butyl-3-(1-oxobutyl)-1H-1,2,4-triazol-5-yl]methyl]-3-pyridinyl]benzoic acid;
2-[6-[[1-butyl-3-(1-oxopentyl)-1H-1,2,4-triazol-5-yl]methyl]-3-pyridinyl]benzoic acid;
2-[6-[[1-butyl-3-(1,1-difluorobutyl)-1H-1,2,4-triazol-5-yl]methyl]-3-pyridinyl]benzoic acid;
2-[6-[(1-pentyl-3-methyl-1H-1,2,4-triazol-5-yl)methyl]-3-pyridinyl]benzoic acid;
2-[6-[(1-pentyl-3-ethyl-1H-1,2,4-triazol-5-yl)methyl]-3-pyridinyl]benzoic acid;
2-[6-[(1-pentyl-3-propyl-1H-1,2,4-triazol-5-yl)methyl]-3-pyridinyl]benzoic acid;
2-[6-[(1-pentyl-3-isopropyl-1H-1,2,4-triazol-5-yl)methyl]-3-pyridinyl]benzoic acid;
2-[6-[(1-pentyl-3-butyl-1H-1,2,4-triazol-5-yl)methyl]-3-pyridinyl]benzoic acid;
2-[6-[(1-pentyl-3-secbutyl-1H-1,2,4-triazol-5-yl)methyl]-3-pyridinyl]benzoic acid;
2-[6-[(1-pentyl-3-isobutyl-1H-1,2,4-triazol-5-yl)methyl]-3-pyridinyl]benzoic acid;
2-[6-[(1-pentyl-3-tertbutyl-1H-1,2,4-triazol-5-yl)methyl]-3-pyridinyl]benzoic acid;
2-[6-[(1,3-dipentyl-1H-1,2,4-triazol-5-yl)methyl]-3-pyridinyl]benzoic acid;
2-[6-[(1-pentyl-3-isopentyl-1H-1,2,4-triazol-5-yl)methyl]-3-pyridinyl]benzoic acid;
2-[6-[(1-pentyl-3-cyclohexyl-1H-1,2,4-triazol-5-yl)methyl]-3-pyridinyl]benzoic acid;
2-[6-[(1-pentyl-3-cyclohexylmethyl-1H-1,2,4-triazol-5-yl)methyl]-3-pyridinyl]benzoic acid;
2-[6-[[1-pentyl-3-(2-cyclohexylethyl)-1H-1,2,4-triazol-5-yl]methyl]-3-pyridinyl]benzoic acid;
2-[6-[(1-pentyl-3-phenyl-1H-1,2,4-triazol-5-yl)methyl]-3-pyridinyl]benzoic acid;
2-[6-[(1-pentyl-3-phenylmethyl-1H-1,2,4-triazol-5-yl)methyl]-3-pyridinyl]benzoic acid;
2-[6-[[1-pentyl-3-(2-phenylethyl)-1H-1,2,4-triazol-5-yl]methyl]-3-pyridinyl]benzoic acid;
2-[6-[(1-pentyl-3-cyclohexanoyl-1H-1,2,4-triazol-5-yl)methyl]-3-pyridinyl]benzoic acid;
2-[6-[[1-pentyl-3-(1-oxo-2-cyclohexylethyl)-1H-1,2,4-triazol-5-yl]methyl]-3-pyridinyl]benzoic acid;
2-[6-[(1-pentyl-3-benzoyl-1H-1,2,4-triazol-5-yl)methyl]-3-pyridinyl]benzoic acid;
2-[6-[[1-pentyl-3-(1-oxo-2-phenylethyl)-1H-1,2,4-triazol-5-yl]methyl]-3-pyridinyl]benzoic acid;
2-[6-[[1-pentyl-3-(1,1-dimethoxypropyl)-1H-1,2,4-triazol-5-yl]methyl]-3-pyridinyl]benzoic acid;
2-[6-[[1-pentyl-3-(1,1-dimethoxybutyl)-1H-1,2,4-triazol-5-yl]methyl]-3-pyridinyl]benzoic acid;
2-[6-[[1-pentyl-3-(1,1-dimethoxypentyl)-1H-1,2,4-triazol-5-yl]methyl]-3-pyridinyl]benzoic acid;
2-[6-[[1-pentyl-3-(1-oxopropyl)-1H-1,2,4-triazol-5-yl]methyl]-3-pyridinyl]benzoic acid;
2-[6-[[1-pentyl-3-(1-oxobutyl)-1H-1,2,4-triazol-5-yl]methyl]-3-pyridinyl]benzoic acid;
2-[6-[[1-pentyl-3-(1-oxopentyl)-1H-1,2,4-triazol-5-yl]methyl]-3-pyridinyl]benzoic acid;
2-[6-[[1-pentyl-3-(1,1-difluorobutyl)-1H-1,2,4-triazol-5-yl]methyl]-3-pyridinyl]benzoic acid;
5-[2-[6-[(1-propyl-3-methyl-1H-1,2,4-triazol-5-yl)methyl]-3-pyridinyl]phenyl]-1H-tetrazole;
5-[2-[6-[(1-propyl-3-ethyl-1H-1,2,4-triazol-5-yl)methyl]-3-pyridinyl]phenyl]-1H-tetrazole;
5-[2-[6-[(1,3-dipropyl-1H-1,2,4-triazol-5-yl)methyl]-3-pyridinyl]phenyl]-1H-tetrazole;
5-[2-[6-[(1-propyl-3-isopropyl-1H-1,2,4-triazol-5-yl)methyl]-3-pyridinyl]phenyl]-1H-tetrazole;
5-[2-[6-[(1-propyl-3-butyl-1H-1,2,4-triazol-5-yl)methyl]-3-pyridinyl]phenyl]-1H-tetrazole;
5-[2-[6-[(1-propyl-3-secbutyl-1H-1,2,4-triazol-5-yl)methyl]-3-pyridinyl]phenyl]-1H-tetrazole;
5-[2-[6-[(1-propyl-3-isobutyl-1H-1,2,4-triazol-5-yl)methyl]-3-pyridinyl]phenyl]-1H-tetrazole;
5-[2-[6-[(1-propyl-3-tertbutyl-1H-1,2,4-triazol-5-yl)methyl]-3-pyridinyl]phenyl]-1H-tetrazole;
5-[2-[6-[(1-propyl-3-pentyl-1H-1,2,4-triazol-5-yl)methyl]-3-pyridinyl]phenyl]-1H-tetrazole;
5-[2-[6-[(1-propyl-3-isopentyl-1H-1,2,4-triazol-5-yl)methyl]-3-pyridinyl]phenyl]-1H-tetrazole;
5-[2-[6-[(1-propyl-3-cyclohexyl-1H-1,2,4-triazol-5-yl)methyl]-3-pyridinyl]phenyl]-1H-tetrazole;
5-[2-[6-[(1-propyl-3-cyclohexylmethyl-1H-1,2,4-triazol-5-yl)methyl]-3-pyridinyl]phenyl]-1H-tetrazole;
5-[2-[6-[[1-propyl-3-(2-cyclohexylethyl)-1H-1,2,4-triazol-5-yl]methyl]-3-pyridinyl]phenyl]-1H-tetrazole;
5-[2-[6-[(1-propyl-3-phenyl-1H-1,2,4-triazol-5-yl)methyl]-3-pyridinyl]phenyl]-1H-tetrazole;
5-[2-[6-[(1-propyl-3-phenylmethyl-1H-1,2,4-triazol-5-yl)methyl]-3-pyridinyl]phenyl]-1H-tetrazole;
5-[2-[6-[[1-propyl-3-(2-phenylethyl)-1H-1,2,4-triazol-5-yl]methyl]-3-pyridinyl]phenyl]-1H-tetrazole;
5-[2-[6-[(1-propyl-3-cyclohexanoyl-1H-1,2,4-triazol-5-yl)methyl]-3-pyridinyl]phenyl]-1H-tetrazole;
5-[2-[6-[[1-propyl-3-(1-oxo-2-cyclohexylethyl)-1H-1,2,4-triazol-5-yl]methyl]-3-pyridinyl]phenyl]-1H-tetrazole;
5-[2-[6-[(1-propyl-3-benzoyl-1H-1,2,4-triazol-5-yl)methyl]-3-pyridinyl]phenyl]-1H-tetrazole;
5-[2-[6-[[1-propyl-3-(1-oxo-2-phenylethyl)-1H-1,2,4-triazol-5-yl]methyl]-3-pyridinyl]phenyl]-1H-tetrazole;
5-[2-[6-[[1-propyl-3-(1,1-dimethoxypropyl)-1H-1,2,4-triazol-5-yl]methyl]-3-pyridinyl]phenyl]-1H-tetrazole;
5-[2-[6-[[1-propyl-3-(1,1-dimethoxybutyl)-1H-1,2,4-triazol-5-yl]methyl]-3-pyridinyl]phenyl]-1H-tetrazole;
5-[2-[6-[[1-propyl-3-(1,1-dimethoxypentyl)-1H-1,2,4-triazol-5-yl]methyl]-3-pyridinyl]phenyl]-1H-tetrazole;
5-[2-[6-[[1-propyl-3-(1-oxopropyl)-1H-1,2,4-triazol-5-yl]methyl]-3-pyridinyl]phenyl]-1H-tetrazole;
5-[2-[6-[[1-propyl-3-(1-oxobutyl)-1H-1,2,4-triazol-5-yl]methyl]-3-pyridinyl]phenyl]-1H-tetrazole;
5-[2-[6-[[1-propyl-3-(1-oxopentyl)-1H-1,2,4-triazol-5-yl]methyl]-3-pyridinyl]phenyl]-1H-tetrazole;
5-[2-[6-[[1-propyl-3-(1,1-difluorobutyl)-1H-1,2,4-triazol-5-yl]methyl]-3-pyridinyl]phenyl]-1H-tetrazole;
5-[2-[6-[(1-butyl-3-methyl-1H-1,2,4-triazol-5-yl)methyl]-3-pyridinyl]phenyl]-1H-tetrazole;
5-[2-[6-[(1-butyl-3-ethyl-1H-1,2,4-triazol-5-yl)methyl]-3-pyridinyl]phenyl]-1H-tetrazole;
5-[2-[6-[(1-butyl-3-propyl-1H-1,2,4-triazol-5-yl)methyl]-3-pyridinyl]phenyl]-1H-tetrazole;
5-[2-[6-[(1-butyl-3-isopropyl-1H-1,2,4-triazol-5-yl)methyl]-3-pyridinyl]phenyl]-1H-tetrazole;
5-[2-[6-[(1,3-dibutyl-1H-1,2,4-triazol-5-yl)methyl]-3-pyridinyl]phenyl]-1H-tetrazole;
5-[2-[6-[(1-butyl-3-secbutyl-1H-1,2,4-triazol-5-yl)methyl]-3-pyridinyl]phenyl]-1H-tetrazole;

5-[2-[6-[(1-butyl-3-isobutyl-1H-1,2,4-triazol-5-yl)methyl]-3-pyridinyl]phenyl]-1H-tetrazole;
5-[2-[6-[(1-butyl-3-tertbutyl-1H-1,2,4-triazol-5-yl)methyl]-3-pyridinyl]phenyl]-1H-tetrazole;
5-[2-[6-[(1-butyl-3-pentyl-1H-1,2,4-triazol-5-yl)methyl]-3-pyridinyl]phenyl]-1H-tetrazole;
5-[2-[6-[(1-butyl-3-isopentyl-1H-1,2,4-triazol-5-yl)methyl]-3-pyridinyl]phenyl]-1H-tetrazole;
5-[2-[6-[(1-butyl-3-cyclohexyl-1H-1,2,4-triazol-5-yl)methyl]-3-pyridinyl]phenyl]-1H-tetrazole;
5-[2-[6-[(1-butyl-3-cyclohexylmethyl-1H-1,2,4-triazol-5-yl)methyl]-3-pyridinyl]phenyl]-1H-tetrazole;
5-[2-[6-[[1-butyl-3-(2-cyclohexylethyl)-1H-1,2,4-triazol-5-yl]methyl]-3-pyridinyl]phenyl]-1H-tetrazole;
5-[2-[6-[(1-butyl-3-phenyl-1H-1,2,4-triazol-5-yl)methyl]-3-pyridinyl]phenyl]-1H-tetrazole;
5-[2-[6-[(1-butyl-3-phenylmethyl-1H-1,2,4-triazol-5-yl)methyl]-3-pyridinyl]phenyl]-1H-tetrazole;
5-[2-[6-[[1-butyl-3-(2-phenylethyl)-1H-1,2,4-triazol-5-yl]methyl]-3-pyridinyl]phenyl]-1H-tetrazole;
5-[2-[6-[(1-butyl-3-cyclohexanoyl-1H-1,2,4-triazol-5-yl)methyl]-3-pyridinyl]phenyl]-1H-tetrazole;
5-[2-[6-[[1-butyl-3-(1-oxo-2-cyclohexylethyl)-1H-1,2,4-triazol-5-yl]methyl]-3-pyridinyl]phenyl]-1H-tetrazole;
5-[2-[6-[(1-butyl-3-benzoyl-1H-1,2,4-triazol-5-yl)methyl]-3-pyridinyl]phenyl]-1H-tetrazole;
5-[2-[6-[[1-butyl-3-(1-oxo-2-phenylethyl)-1H-1,2,4-triazol-5-yl]methyl]-3-pyridinyl]phenyl]-1H-tetrazole;
5-[2-[6-[[1-butyl-3-(1,1-dimethoxypropyl)-1H-1,2,4-triazol-5-yl]methyl]-3-pyridinyl]phenyl]-1H-tetrazole;
5-[2-[6-[[1-butyl-3-(1,1-dimethoxybutyl)-1H-1,2,4-triazol-5-yl]methyl]-3-pyridinyl]phenyl]-1H-tetrazole;
5-[2-[6-[[1-butyl-3-(1,1-dimethoxypentyl)-1H-1,2,4-triazol-5-yl]methyl]-3-pyridinyl]phenyl]-1H-tetrazole;
5-[2-[6-[[1-butyl-3-(1-oxopropyl)-1H-1,2,4-triazol-5-yl]methyl]-3-pyridinyl]phenyl]-1H-tetrazole;
5-[2-[6-[[1-butyl-3-(1-oxobutyl)-1H-1,2,4-triazol-5-yl]methyl]-3-pyridinyl]phenyl]-1H-tetrazole;
5-[2-[6-[[1-butyl-3-(1-oxopentyl)-1H-1,2,4-triazol-5-yl]methyl]-3-pyridinyl]phenyl]-1H-tetrazole;
5-[2-[6-[[1-butyl-3-(1,1-difluorobutyl)-1H-1,2,4-triazol-5-yl]methyl]-3-pyridinyl]phenyl]-1H-tetrazole;
5-[2-[6-[(1-pentyl-3-methyl-1H-1,2,4-triazol-5-yl)methyl]-3-pyridinyl]phenyl]-1H-tetrazole;
5-[2-[6-[(1-pentyl-3-ethyl-1H-1,2,4-triazol-5-yl)methyl]-3-pyridinyl]phenyl]-1H-tetrazole;
5-[2-[6-[(1-pentyl-3-propyl-1H-1,2,4-triazol-5-yl)methyl]-3-pyridinyl]phenyl]-1H-tetrazole;
5-[2-[6-[(1-pentyl-3-isopropyl-1H-1,2,4-triazol-5-yl)methyl]-3-pyridinyl]phenyl]-1H-tetrazole;
5-[2-[6-[(1-pentyl-3-butyl-1H-1,2,4-triazol-5-yl)methyl]-3-pyridinyl]phenyl]-1H-tetrazole;
5-[2-[6-[(1-pentyl-3-secbutyl-1H-1,2,4-triazol-5-yl)methyl]-3-pyridinyl]phenyl]-1H-tetrazole;
5-[2-[6-[(1-pentyl-3-isobutyl-1H-1,2,4-triazol-5-yl)methyl]-3-pyridinyl]phenyl]-1H-tetrazole;
5-[2-[6-[(1-pentyl-3-tertbutyl-1H-1,2,4-triazol-5-yl)methyl]-3-pyridinyl]phenyl]-1H-tetrazole;
5-[2-[6-[(1,3-di-pentyl-1H-1,2,4-triazol-5-yl)methyl]-3-pyridinyl]phenyl]-1H-tetrazole;
5-[2-[6-[(1-pentyl-3-isopentyl-1H-1,2,4-triazol-5-yl)methyl]-3-pyridinyl]phenyl]-1H-tetrazole;
5-[2-[6-[(1-pentyl-3-cyclohexyl-1H-1,2,4-triazol-5-yl)methyl]-3-pyridinyl]phenyl]-1H-tetrazole;
5-[2-[6-[(1-pentyl-3-cyclohexylmethyl-1H-1,2,4-triazol-5-yl)methyl]-3-pyridinyl]phenyl]-1H-tetrazole;
5-[2-[6-[[1-pentyl-3-(2-cyclohexylethyl)-1H-1,2,4-triazol-5-yl]methyl]-3-pyridinyl]phenyl]-1H-tetrazole;
5-[2-[6-[(1-pentyl-3-phenyl-1H-1,2,4-triazol-5-yl)methyl]-3-pyridinyl]phenyl]-1H-tetrazole;
5-[2-[6-[(1-pentyl-3-phenylmethyl-1H-1,2,4-triazol-5-yl)methyl]-3-pyridinyl]phenyl]-1H-tetrazole;
5-[2-[6-[[1-pentyl-3-(2-phenylethyl)-1H-1,2,4-triazol-5-yl]methyl]-3-pyridinyl]phenyl]-1H-tetrazole;
5-[2-[6-[(1-pentyl-3-cyclohexanoyl-1H-1,2,4-triazol-5-yl)methyl]-3-pyridinyl]phenyl]-1H-tetrazole;
5-[2-[6-[[1-pentyl-3-(1-oxo-2-cyclohexylethyl)-1H-1,2,4-triazol-5-yl]methyl]-3-pyridinyl]phenyl]-1H-tetrazole;
5-[2-[6-[(1-pentyl-3-benzoyl-1H-1,2,4-triazol-5-yl)methyl]-3-pyridinyl]phenyl]-1H-tetrazole;
5-[2-[6-[[1-pentyl-3-(1-oxo-2-phenylethyl)-1H-1,2,4-triazol-5-yl]methyl]-3-pyridinyl]phenyl]-1H-tetrazole;
5-[2-[6-[[1-pentyl-3-(1,1-dimethoxypropyl)-1H-1,2,4-triazol-5-yl]methyl]-3-pyridinyl]phenyl]-1H-tetrazole;
5-[2-[6-[[1-pentyl-3-(1,1-dimethoxybutyl)-1H-1,2,4-triazol-5-yl]methyl]-3-pyridinyl]phenyl]-1H-tetrazole;
5-[2-[6-[[1-pentyl-3-(1,1-dimethoxypentyl)-1H-1,2,4-triazol-5-yl]methyl]-3-pyridinyl]phenyl]-1H-tetrazole;
5-[2-[6-[[1-pentyl-3-(1-oxopropyl)-1H-1,2,4-triazol-5-yl]methyl]-3-pyridinyl]phenyl]-1H-tetrazole;
5-[2-[6-[[1-pentyl-3-(1-oxobutyl)-1H-1,2,4-triazol-5-yl]methyl]-3-pyridinyl]phenyl]-1H-tetrazole;
5-[2-[6-[[1-pentyl-3-(1-oxopentyl)-1H-1,2,4-triazol-5-yl]methyl]-3-pyridinyl]phenyl]-1H-tetrazole; and
5-[2-[6-[[1-pentyl-3-(1,1-difluorobutyl)-1H-1,2,4-triazol-5-yl]methyl]-3-pyridinyl]phenyl]-1H-tetrazole.

A family of specific compounds of more particular interest within Formula II consists of the following compounds:

5-[2-[6-[(1-butyl-3-methyl-1H-1,2,4-triazol-5-yl)methyl]-3-pyridinyl]phenyl]-1H-tetrazole;
5-[2-[6-[(1-butyl-3-ethyl-1H-1,2,4-triazol-5-yl)methyl]-3-pyridinyl]phenyl]-1H-tetrazole;
5-[2-[6-[(1-butyl-3-propyl-1H-1,2,4-triazol-5-yl)methyl]-3-pyridinyl]phenyl]-1H-tetrazole;
5-[2-[6-[(1-butyl-3-isopropyl-1H-1,2,4-triazol-5-yl)methyl]-3-pyridinyl]phenyl]-1H-tetrazole;
5-[2-[6-[(1,3-dibutyl-1H-1,2,4-triazol-5-yl)methyl]-3-pyridinyl]phenyl]-1H-tetrazole;
5-[2-[6-[(1-butyl-3-secbutyl-1H-1,2,4-triazol-5-yl)methyl]-3-pyridinyl]phenyl]-1H-tetrazole;
5-[2-[6-[(1-butyl-3-isobutyl-1H-1,2,4-triazol-5-yl)methyl]-3-pyridinyl]phenyl]-1H-tetrazole;
5-[2-[6-[(1-butyl-3-tertbutyl-1H-1,2,4-triazol-5-yl)methyl]-3-pyridinyl]phenyl]-1H-tetrazole;
5-[2-[6-[(1-butyl-3-pentyl-1H-1,2,4-triazol-5-yl)methyl]-3-pyridinyl]phenyl]-1H-tetrazole;
5-[2-[6-[(1-butyl-3-isopentyl-1H-1,2,4-triazol-5-yl)methyl]-3-pyridinyl]phenyl]-1H-tetrazole;
5-[2-[6-[(1-butyl-3-cyclohexyl-1H-1,2,4-triazol-5-yl)methyl]-3-pyridinyl]phenyl]-1H-tetrazole;
5-[2-[6-[(1-butyl-3-cyclohexylmethyl-1H-1,2,4-triazol-5-yl)methyl]-3-pyridinyl]phenyl]-1H-tetrazole;

5-[2-[6-[[1-butyl-3-(2-cyclohexylethyl)-1H-1,2,4-triazol-5-yl)methyl]-3-pyridinyl]phenyl]-1H-tetrazole;

5-[2-[6-[(1-butyl-3-phenyl-1H-1,2,4-triazol-5-yl)methyl]-3-pyridinyl]phenyl]-1H-tetrazole;

5-[2-[6-[(1-butyl-3-phenylmethyl-1H-1,2,4-triazol-5-yl)methyl]-3-pyridinyl]phenyl]-1H-tetrazole; and 5-[2-[6-[(1-butyl-3-(2-phenylethyl)-1H-1,2,4-triazol-5-yl)methyl]-3-pyridinyl]phenyl]-1H-tetrazole.

Another subclass of compounds of Formula I which is of even more particular interest consists of those compounds of Formula III

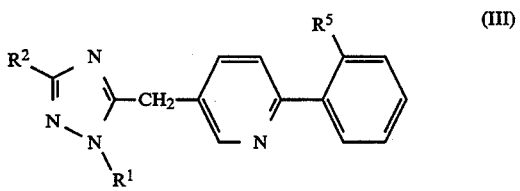

wherein m is one; wherein $R^1$ is selected from methyl, ethyl, n-propyl, isopropyl, n-butyl, sec-butyl, isobutyl, tert-butyl, 4-methylbutyl, n-pentyl, neopentyl, phenyl, benzyl, phenethyl, cyclohexyl, cyclohexylmethyl, 2-butenyl, 3-butenyl, 2-butynyl, 3-butynyl and 2-hydroxybutyl; wherein $R^2$ is selected from ethyl, n-propyl, isopropyl, n-butyl, sec-butyl, isobutyl, 4-methylbutyl, n-pentyl, 1-oxo-2-phenylethyl, 1-oxo-2-cyclohexylethyl, 1,1-difluoro-2-phenylethyl, 1,1-difluoro-2-cyclohexylethyl, 2-cyclohexylethyl, 1,1-difluoro-3-cyclohexylpropyl, 1,1-dimethoxybutyl, 1,1-difluoroethyl, 1,1-difluoropropyl, 1,1-difluorobutyl, 1,1-difluoropentyl, benzyl, 2-phenylethyl, 1,1-difluoro-3-phenylpropyl, cyclohexylmethyl, cyclohexanoyl, 1-butenyl, 2-butenyl, 3-butenyl, 1-butynyl, 2-butynyl, 3-butynyl, propylthio and butylthio; wherein $R^5$ is an acidic group selected from $CO_2H$ and

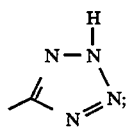

or a tautomer thereof or a pharmaceutically-acceptable salt thereof.

A family of specific compounds of particular interest within Formula III consists of the following compounds:

2-[5-[(1-propyl-3-methyl-1H-1,2,4-triazol-5-yl)methyl]-2-pyridinyl]benzoic acid;

2-[5-[(1-propyl-3-ethyl-1H-1,2,4-triazol-5-yl)methyl]-2pyridinyl]benzoic acid;

2-[5-[(1,3-dipropyl-1H-1,2,4-triazol-5-yl)methyl]-2pyridinyl]benzoic acid;

2-[5-[(1-propyl-3-isopropyl-1H-1,2,4-triazol-5-yl)methyl]-2-pyridinyl]benzoic acid;

2-[5-[(1-propyl-3-butyl-1H-1,2,4-triazol-5-yl)methyl]-2pyridinyl]benzoic acid;

2-[5-[(1-propyl-3-secbutyl-1H-1,2,4-triazol-5-yl)methyl]-2-pyridinyl]benzoic acid;

2-[5-[(1-propyl-3-isobutyl-1H-1,2,4-triazol-5-yl)methyl]-2-pyridinyl]benzoic acid;

2-[5-[(1-propyl-3-tertbutyl-1H-1,2,4-triazol-5-yl)methyl]-2-pyridinyl]benzoic acid;

2-[5-[(1-propyl-3-pentyl-1H-1,2,4-triazol-5-yl)methyl]-2-pyridinyl]benzoic acid;

2-[5-[(1-propyl-3-isopentyl-1H-1,2,4-triazol-5-yl)methyl]-2-pyridinyl]benzoic acid;

2-[5-[(1-propyl-3-cyclohexyl-1H-1,2,4-triazol-5-yl)methyl]-2-pyridinyl]benzoic acid;

2-[5-[(1-propyl-3-cyclohexylmethyl-1H-1,2,4-triazol-5-yl)methyl]-2-pyridinyl]benzoic acid;

2-[5-[[1-propyl-3-(2-cyclohexylethyl)-1H-1,2,4-triazol-5-yl]methyl]-2-pyridinyl]benzoic acid;

2-[5-[(1-propyl-3-phenyl-1H-1,2,4-triazol-5-yl)methyl]-2-pyridinyl]benzoic acid;

2-[5-[(1-propyl-3-phenylmethyl-1H-1,2,4-triazol-5-yl)methyl]-2-pyridinyl]benzoic acid;

2-[5-[[1-propyl-3-(2-phenylethyl)-1H-1,2,4-triazol-5-yl]methyl]-2-pyridinyl]benzoic acid;

2-[5-[(1-propyl-3-cyclohexanoyl-1H-1,2,4-triazol-5-yl)methyl]-2-pyridinyl]benzoic acid;

2-[5-[[1-propyl-3-(1-oxo-2-cyclohexylethyl)-1H-1,2,4-triazol-5-yl]methyl]-2-pyridinyl]benzoic acid;

2-[5-[(1-propyl-3-benzoyl-1H-1,2,4-triazol-5-yl)methyl]-2-pyridinyl]benzoic acid;

2-[5-[[1-propyl-3-(1-oxo-2-phenylethyl)-1H-1,2,4-triazol-5-yl]methyl]-2-pyridinyl]benzoic acid;

2-[5-[[1-propyl-3-(1,1-dimethoxypropyl)-1H-1,2,4-triazol-5-yl]methyl]-2-pyridinyl]benzoic acid;

2-[5-[[1-propyl-3-(1,1-dimethoxybutyl)-1H-1,2,4-triazol-5-yl]methyl]-2-pyridinyl]benzoic acid;

2-[5-[[1-propyl-3-(1,1-dimethoxypentyl)-1H-1,2,4-triazol-5-yl]methyl]-2-pyridinyl]benzoic acid;

2-[5-[[1-propyl-3-(1-oxopropyl)-1H-1,2,4-triazol-5-yl]methyl]-2-pyridinyl]benzoic acid;

2-[5-[[1-propyl-3-(1-oxobutyl)-1H-1,2,4-triazol-5-yl]methyl]-2-pyridinyl]benzoic acid;

2-[5-[[1-propyl-3-(1-oxopentyl)-1H-1,2,4-triazol-5-yl]methyl]-2-pyridinyl]benzoic acid;

2-[5-[[1-propyl-3-(1,1-difluorobutyl)-1H-1,2,4-triazol-5-yl]methyl]-2-pyridinyl]benzoic acid;

2-[5-[(1-butyl-3-methyl-1H-1,2,4-triazol-5-yl)methyl]-2-pyridinyl]benzoic acid;

2-[5-[(1-butyl-3-ethyl-1H-1,2,4-triazol-5-yl)methyl]-2-pyridinyl]benzoic acid;

2-[5-[(1-butyl-3-propyl-1H-1,2,4-triazol-5-yl)methyl]-2-pyridinyl]benzoic acid;

2-[5-[(1-butyl-3-isopropyl-1H-1,2,4-triazol-5-yl)methyl]-2-pyridinyl]benzoic acid;

2-[5-[(1,3-dibutyl-1H-1,2,4-triazol-5-yl)methyl]-2-pyridinyl]benzoic acid;

2-[5-[(1-butyl-3-secbutyl-1H-1,2,4-triazol-5-yl)methyl]-2-pyridinyl]benzoic acid;

2-[5-[(1-butyl-3-isobutyl-1H-1,2,4-triazol-5-yl)methyl]-2-pyridinyl]benzoic acid;

2-[5-[(1-butyl-3-tertbutyl-1H-1,2,4-triazol-5-yl)methyl]-2-pyridinyl]benzoic acid;

2-[5-[(1-butyl-3-pentyl-1H-1,2,4-triazol-5-yl)methyl]-2-pyridinyl]benzoic acid;

2-[5-[(1-butyl-3-isopentyl-1H-1,2,4-triazol-5-yl)methyl]-2-pyridinyl]benzoic acid;

2-[5-[(1-butyl-3-cyclohexyl-1H-1,2,4-triazol-5-yl)methyl]-2-pyridinyl]benzoic acid;

2-[5-[(1-butyl-3-cyclohexylmethyl-1H-1,2,4-triazol-5-yl)methyl]-2-pyridinyl]benzoic acid;

2-[5-[[1-butyl-3-(2-cyclohexylethyl)-1H-1,2,4-triazol-5-yl]methyl]-2-pyridinyl]benzoic acid;

2-[5-[(1-butyl-3-phenyl-1H-1,2,4-triazol-5-yl)methyl]-2-pyridinyl]benzoic acid;

2-[5-[(1-butyl-3-phenylmethyl-1H-1,2,4-triazol-5-yl)methyl]-2-pyridinyl]benzoic acid;

2-[5-[[1-butyl-3-(2-phenylethyl)-1H-1,2,4-triazol-5-yl]methyl]-2-pyridinyl]benzoic acid;

2-[5-[(1-butyl-3-cyclohexanoyl-1H-1,2,4-triazol-5-yl)methyl]-2-pyridinyl]benzoic acid;
2-[5-[[1-butyl-3-(1-oxo-2-cyclohexylethyl)-1H-1,2,4-triazol-5-yl]methyl]-2-pyridinyl]benzoic acid;
2-[5-[(1-butyl-3-benzoyl-1H-1,2,4-triazol-5-yl)methyl]-2-pyridinyl]benzoic acid;
2-[5-[[1-butyl-3-(1-oxo-2-phenylethyl)-1H-1,2,4-triazol-5-yl]methyl]-2-pyridinyl]benzoic acid;
2-[5-[[1-butyl-3-(1,1-dimethoxypropyl)-1H-1,2,4-triazol-5-yl]methyl]-2-pyridinyl]benzoic acid;
2-[5-[[1-butyl-3-(1,1-dimethoxybutyl)-1H-1,2,4-triazol-5-yl]methyl]-2-pyridinyl]benzoic acid;
2-[5-[[1-butyl-3-(1,1-dimethoxypentyl)-1H-1,2,4-triazol-5-yl]methyl]-2-pyridinyl]benzoic acid;
2-[5-[[1-butyl-3-(1-oxopropyl)-1H-1,2,4-triazol-5-yl]methyl]-2-pyridinyl]benzoic acid;
2-[5-[[1-butyl-3-(1-oxobutyl)-1H-1,2,4-triazol-5-yl]methyl]-2-pyridinyl]benzoic acid;
2-[5-[[1-butyl-3-(1-oxopentyl)-1H-1,2,4-triazol-5-yl]methyl]-2-pyridinyl]benzoic acid;
2-[5-[[1-butyl-3-(1,1-difluorobutyl)-1H-1,2,4-triazol-5-yl]methyl]-2-pyridinyl]benzoic acid;
2-[5-[(1-pentyl-3-methyl-1H-1,2,4-triazol-5-yl)methyl]-2-pyridinyl]benzoic acid;
2-[5-[(1-pentyl-3-ethyl-1H-1,2,4-triazol-5-yl)methyl]-2-pyridinyl]benzoic acid;
2-[5-[(1-pentyl-3-propyl-1H-1,2,4-triazol-5-yl)methyl]-2-pyridinyl]benzoic acid;
2-[5-[(1-pentyl-3-isopropyl-1H-1,2,4-triazol-5-yl)methyl]-2-pyridinyl]benzoic acid;
2-[5-[(1-pentyl-3-butyl-1H-1,2,4-triazol-5-yl)methyl]-2-pyridinyl]benzoic acid;
2-[5-[(1-pentyl-3-secbutyl-1H-1,2,4-triazol-5-yl)methyl]-2-pyridinyl]benzoic acid;
2-[5-[(1-pentyl-3-isobutyl-1H-1,2,4-triazol-5-yl)methyl]-2-pyridinyl]benzoic acid;
2-[5-[(1-pentyl-3-tertbutyl-1H-1,2,4-triazol-5-yl)methyl]-2-pyridinyl]benzoic acid;
2-[5-[(1,3-dipentyl-1H-1,2,4-triazol-5-yl)methyl]-2-pyridinyl]benzoic acid;
2-[5-[(1-pentyl-3-isopentyl-1H-1,2,4-triazol-5-yl)methyl]-2-pyridinyl]benzoic acid;
2-[5-[(1-pentyl-3-cyclohexyl-1H-1,2,4-triazol-5-yl)methyl]-2-pyridinyl]benzoic acid;
2-[5-[(1-pentyl-3-cyclohexylmethyl-1H-1,2,4-triazol-5-yl)methyl]-2-pyridinyl]benzoic acid;
2-[5-[[1-pentyl-3-(2-cyclohexylethyl)-1H-1,2,4-triazol-5-yl]methyl]-2-pyridinyl]benzoic acid;
2-[5-[(1-pentyl-3-phenyl-1H-1,2,4-triazol-5-yl)methyl]-2-pyridinyl]benzoic acid;
2-[5-[(1-pentyl-3-phenylmethyl-1H-1,2,4-triazol-5-yl)methyl]-2-pyridinyl]benzoic acid;
2-[5-[[1-pentyl-3-(2-phenylethyl)-1H-1,2,4-triazol-5-yl]methyl]-2-pyridinyl]benzoic acid;
2-[5-[(1-pentyl-3-cyclohexanoyl-1H-1,2,4-triazol-5-yl)methyl]-2-pyridinyl]benzoic acid;
2-[5-[[1-pentyl-3-(1-oxo-2-cyclohexylethyl)-1H-1,2,4-triazol-5-yl]methyl]-2-pyridinyl]benzoic acid;
2-[5-[(1-pentyl-3-benzoyl-1H-1,2,4-triazol-5-yl)methyl]-2-pyridinyl]benzoic acid;
2-[5-[[1-pentyl-3-(1-oxo-2-phenylethyl)-1H-1,2,4-triazol-5-yl]methyl]-2-pyridinyl]benzoic acid;
2-[5-[[1-pentyl-3-(1,1-dimethoxypropyl)-1H-1,2,4-triazol-5-yl]methyl]-2-pyridinyl]benzoic acid;
2-[5-[[1-pentyl-3-(1,1-dimethoxybutyl)-1H-1,2,4-triazol-5-yl]methyl]-2-pyridinyl]benzoic acid;
2-[5-[[1-pentyl-3-(1,1-dimethoxypentyl)-1H-1,2,4-triazol-5-yl]methyl]-2-pyridinyl]benzoic acid;
2-[5-[[1-pentyl-3-(1-oxopropyl)-1H-1,2,4-triazol-5-yl]methyl]-2-pyridinyl]benzoic acid;
2-[5-[[1-pentyl-3-(1-oxobutyl)-1H-1,2,4-triazol-5-yl]methyl]-2-pyridinyl]benzoic acid;
2-[5-[[1-pentyl-3-(1-oxopentyl)-1H-1,2,4-triazol-5-yl]methyl]-2-pyridinyl]benzoic acid;
2-[5-[[1-pentyl-3-(1,1-difluorobutyl)-1H-1,2,4-triazol-5-yl]methyl]-2-pyridinyl]benzoic acid;
5-[2-[5-[(1-propyl-3-methyl-1H-1,2,4-triazol-5-yl)methyl]-2-pyridinyl]phenyl]-1H-tetrazole;
5-[2-[5-[(1-propyl-3-ethyl-1H-1,2,4-triazol-5-yl)methyl]-2-pyridinyl]phenyl]-1H-tetrazole;
5-[2-[5-[(1,3-dipropyl-1H-1,2,4-triazol-5-yl)methyl]-2-pyridinyl]phenyl]-1H-tetrazole;
5-[2-[5-[(1-propyl-3-isopropyl-1H-1,2,4-triazol-5-yl)methyl]-2-pyridinyl]phenyl]-1H-tetrazole;
5-[2-[5-[(1-propyl-3-butyl-1H-1,2,4-triazol-5-yl)methyl]-2-pyridinyl]phenyl]-1H-tetrazole;
5-[2-[5-[(1-propyl-3-secbutyl-1H-1,2,4-triazol-5-yl)methyl]-2-pyridinyl]phenyl]-1H-tetrazole;
5-[2-[5-[(1-propyl-3-isobutyl-1H-1,2,4-triazol-5-yl)methyl]-2-pyridinyl]phenyl]-1H-tetrazole;
5-[2-[5-[(1-propyl-3-tertbutyl-1H-1,2,4-triazol-5-yl)methyl]-2-pyridinyl]phenyl]-1H-tetrazole;
5-[2-[5-[(1-propyl-3-pentyl-1H-1,2,4-triazol-5-yl)methyl]-2-pyridinyl]phenyl]-1H-tetrazole;
5-[2-[5-[(1-propyl-3-isopentyl-1H-1,2,4-triazol-5-yl)methyl ]-2-pyridinyl]phenyl]-1H-tetrazole;
5-[2-[5-[(1-propyl-3-cyclohexyl-1H-1,2,4-triazol-5-yl)methyl]-2-pyridinyl]phenyl]-1H-tetrazole;
5-[2-[5-[(1-propyl-3-cyclohexylmethyl-1H-1,2,4-triazol-5-yl)methyl]-2-pyridinyl]phenyl]-1H-tetrazole;
5-[2-[5-[[1-propyl-3-(2-cyclohexylethyl)-1H-1,2,4-triazol-5-yl]methyl]-2-pyridinyl]phenyl]-1H-tetrazole;
5-[2-[5-[(1-propyl-3-phenyl-1H-1,2,4-triazol-5-yl)methyl]-2-pyridinyl]phenyl]-1H-tetrazole;
5-[2-[5-[(1-propyl-3-phenylmethyl-1H-1,2,4-triazol-5-yl)methyl]-2-pyridinyl]phenyl]-1H-tetrazole;
5-[2-[5-[[1-propyl-3-(2-phenylethyl)-1H-1,2,4-triazol-5-yl]methyl]-2-pyridinyl]phenyl]-1H-tetrazole;
5-[2-[5-[(1-propyl-3-cyclohexanoyl-1H-1,2,4-triazol-5-yl)methyl]-2-pyridinyl]phenyl]-1H-tetrazole;
5-[2-[5-[[1-propyl-3-(1-oxo-2-cyclohexylethyl)-1H-1,2,4-triazol-5-yl]methyl]-2-pyridinyl]phenyl]-1H-tetrazole;
5-[2-[5-[(1-propyl-3-benzoyl-1H-1,2,4-triazol-5-yl)methyl]-2-pyridinyl]phenyl]-1H-tetrazole;
5-[2-[5-[[1-propyl-3-(1-oxo-2-phenylethyl)-1H-1,2,4-triazol-5-yl]methyl]-2-pyridinyl]phenyl]-1H-tetrazole;
5-[2-[5-[[1-propyl-3-(1,1-dimethoxypropyl)-1H-1,2,4-triazol-5-yl]methyl]-2-pyridinyl]phenyl]-1H-tetrazole;
5-[2-[5-[[1-propyl-3-(1,1-dimethoxybutyl)-1H-1,2,4-triazol-5-yl]methyl]-2-pyridinyl]phenyl]-1H-tetrazole;
5-[2-[5-[[1-propyl-3-(1,1-dimethoxypentyl)-1H-1,2,4-triazol-5-yl]methyl]-2-pyridinyl]phenyl]-1H-tetrazole;
5-[2-[5-[[1-propyl-3-(1-oxopropyl)-1H-1,2,4-triazol-5-yl]methyl]-2-pyridinyl]phenyl]-1H-tetrazole;
5-[2-[5-[[1-propyl-3-(1-oxobutyl)-1H-1,2,4-triazol-5-yl]methyl]-2-pyridinyl]phenyl]-1H-tetrazole;
5-[2-[5-[[1-propyl-3-(1-oxopentyl)-1H-1,2,4-triazol-5-yl]methyl]-2-pyridinyl]phenyl]-1H-tetrazole;
5-[2-[5-[[1-propyl-3-(1,1-difluorobutyl)-1H-1,2,4-triazol-5-yl]methyl]-2-pyridinyl]phenyl]-1H-tetrazole;

5-[2-[5-[(1-butyl-3-methyl-1H-1,2,4-triazol-5-yl)methyl]-2-pyridinyl]phenyl]-1H-tetrazole;

5-[2-[5-[(1-butyl-3-ethyl-1H-1,2,4-triazol-5-yl)methyl]--pyridinyl]phenyl]-1H-tetrazole;

5-[2-[5-[(1-butyl-3-propyl-1H-1,2,4-triazol-5-yl)methyl]-2-pyridinyl]phenyl]-1H-tetrazole;

5-[2-[5-[(1-butyl-3-isopropyl-1H-1,2,4-triazol-5-yl)methyl]-2-pyridinyl]phenyl]-1H-tetrazole;

5-[2-[5-[(1,3-dibutyl-1H-1,2,4-triazol-5-yl)methyl]-2-pyridinyl]phenyl]-1H-tetrazole;

5-[2-[5-[(1-butyl-3-secbutyl-1H-1,2,4-triazol-5-yl)methyl]-2-pyridinyl]phenyl]-1H-tetrazole;

5-[2-[5-[(1-butyl-3-isobutyl-1H-1,2,4-triazol-5-yl)methyl]-2-pyridinyl]phenyl]-1H-tetrazole;

5-[2-[5-[(1-butyl-3-tertbutyl-1H-1,2,4-triazol-5-yl)methyl]-2-pyridinyl]phenyl]-1H-tetrazole;

5-[2-[5-[(1-butyl-3-pentyl-1H-1,2,4-triazol-5-yl)methyl]-2-pyridinyl]phenyl]-1H-tetrazole;

5-[2-[5-[(1-butyl-3-isopentyl-1H-1,2,4-triazol-5-yl)methyl]-2-pyridinyl]phenyl]-1H-tetrazole;

5-[2-[5-[(1-butyl-3-cyclohexyl-1H-1,2,4-triazol-5-yl)methyl]-2-pyridinyl]phenyl]-1H-tetrazole;

5-[2-[5-[(1-butyl-3-cyclohexylmethyl-1H-1,2,4-triazol-5-yl)methyl]-2-pyridinyl]phenyl]-1H-tetrazole;

5-[2-[5-[[1-butyl-3-(2-cyclohexylethyl)-1H-1,2,4-triazol-5-yl]methyl]-2-pyridinyl]phenyl]-1H-tetrazole;

5-[2-[5-[(1-butyl-3-phenyl-1H-1,2,4-triazol-5-yl)methyl]-2-pyridinyl]phenyl]-1H-tetrazole;

5-[2-[5-[(1-butyl-3-phenylmethyl-1H-1,2,4-triazol-5-yl)methyl]-2-pyridinyl]phenyl]-1H-tetrazole;

5-[2-[5-[[1-butyl-3-(2-phenylethyl)-1H-1,2,4-triazol-5-yl]methyl]-2-pyridinyl]phenyl]-1H-tetrazole;

5-[2-[5-[(1-butyl-3-cyclohexanoyl-1H-1,2,4-triazol-5-yl)methyl]-2-pyridinyl]phenyl]-1H-tetrazole;

5-[2-[5-[[1-butyl-3-(1-oxo-2-cyclohexylethyl)-1H-1,2,4-triazol-5-yl]methyl]-2-pyridinyl]phenyl]-1H-tetrazole;

5-[2-[5-[(1-butyl-3-benzoyl-1H-1,2,4-triazol-5-yl)methyl]-2-pyridinyl]phenyl]-1H-tetrazole;

5-[2-[5-[[1-butyl-3-(1-oxo-2-phenylethyl)-1H-1,2,4-triazol-5-yl]methyl]-2-pyridinyl]phenyl]-1H-tetrazole;

5-[2-[5-[[1-butyl-3-(1,1-dimethoxypropyl)-1H-1,2,4-triazol-5-yl]methyl]-2-pyridinyl]phenyl]-1H-tetrazole;

5-[2-[5-[[1-butyl-3-(1,1-dimethoxybutyl)-1H-1,2,4-triazol-5-yl]methyl]-2-pyridinyl]phenyl]-1H-tetrazole;

5-[2-[5-[[1-butyl-3-(1,1-dimethoxypentyl)-1H-1,2,4-triazol-5-yl]methyl]-2-pyridinyl]phenyl]-1H-tetrazole;

5-[2-[5-[[1-butyl-3-(1-oxopropyl)-1H-1,2,4-triazol-5-yl]methyl]-2-pyridinyl]phenyl]-1H-tetrazole;

5-[2-[5-[[1-butyl-3-(1-oxobutyl)-1H-1,2,4-triazol-5-yl]methyl]-2-pyridinyl]phenyl]-1H-tetrazole;

5-[2-[5-[[1-butyl-3-(1-oxopentyl)-1H-1,2,4-triazol-5-yl]methyl]-2-pyridinyl]phenyl]-1H-tetrazole;

5-[2-[5-[[1-butyl-3-(1,1-difluorobutyl)-1H-1,2,4-triazol-5-yl]methyl]-2-pyridinyl]phenyl]-1H-tetrazole;

5-[2-[5-[(1-pentyl-3-methyl-1H-1,2,4-triazol-5-yl)methyl]-2-pyridinyl]phenyl]-1H-tetrazole;

5-[2-[5-[(1-pentyl-3-ethyl-1H-1,2,4-triazol-5-yl)methyl]-2-pyridinyl]phenyl]-1H-tetrazole;

5-[2-[5-[(1-pentyl-3-propyl-1H-1,2,4-triazol-5-yl)methyl]-2-pyridinyl]phenyl]-1H-tetrazole;

5-[2-[5-[(1-pentyl-3-isopropyl-1H-1,2,4-triazol-5-yl)methyl]-2-pyridinyl]phenyl]-1H-tetrazole;

5-[2-[5-[(1-pentyl-3-butyl-1H-1,2,4-triazol-5-yl)methyl]-2-pyridinyl]phenyl]-1H-tetrazole;

5-[2-[5-[(1-pentyl-3-secbutyl-1H-1,2,4-triazol-5-yl)methyl]-2-pyridinyl]phenyl]-1H-tetrazole;

5-[2-[5-[(1-pentyl-3-isobutyl-1H-1,2,4-triazol-5-yl)methyl]-2-pyridinyl]phenyl]-1H-tetrazole;

5-[2-[5-[(1-pentyl-3-tertbutyl-1H-1,2,4-triazol-5-yl)methyl]-2-pyridinyl]phenyl]-1H-tetrazole;

5-[2-[5-[(1,3-dipentyl-1H-1,2,4-triazol-5-yl)methyl]-2-pyridinyl]phenyl]-1H-tetrazole;

5-[2-[5-[(1-pentyl-3-isopentyl-1H-1,2,4-triazol-5-yl)methyl]-2-pyridinyl]phenyl]-1H-tetrazole;

5-[2-[5-[(1-pentyl-3-cyclohexyl-1H-1,2,4-triazol-5-yl)methyl]-2-pyridinyl]phenyl]-1H-tetrazole;

5-[2-[5-[(1-pentyl-3-cyclohexylmethyl-1H-1,2,4-triazol-5-yl)methyl]-2-pyridinyl]phenyl]-1H-tetrazole;

5-[2-[5-[[1-pentyl-3-(2-cyclohexylethyl)-1H-1,2,4-triazol-5-yl]methyl]-2-pyridinyl]phenyl]-1H-tetrazole;

5-[2-[5-[(1-pentyl-3-phenyl-1H-1,2,4-triazol-5-yl)methyl]-2-pyridinyl]phenyl]-1H-tetrazole;

5-[2-[5-[(1-pentyl-3-phenylmethyl-1H-1,2,4-triazol-5-yl)methyl]-2-pyridinyl]phenyl]-1H-tetrazole;

5-[2-[5-[[1-pentyl-3-(2-phenylethyl)-1H-1,2,4-triazol-5-yl]methyl]-2-pyridinyl]phenyl]-1H-tetrazole;

5-[2-[5-[(1-pentyl-3-cyclohexanoyl-1H-1,2,4-triazol-5-yl)methyl]-2-pyridinyl]phenyl]-1H-tetrazole;

5-[2-[5-[[1-pentyl-3-(1-oxo-2-cyclohexylethyl)-1H-1,2,4-triazol-5-yl]methyl]-2-pyridinyl]phenyl]-1H-tetrazole;

5-[2-[5-[(1-pentyl-3-benzoyl-1H-1,2,4-triazol-5-yl)methyl]-2-pyridinyl]phenyl]-1H-tetrazole;

5-[2-[5-[[1-pentyl-3-(1-oxo-2-phenylethyl)-1H-1,2,4-triazol-5-yl]methyl]-2-pyridinyl]phenyl]-1H-tetrazole;

5-[2-[5-[[1-pentyl-3-(1,1-dimethoxypropyl)-1H-1,2,4-triazol-5-yl]methyl]-2-pyridinyl]phenyl]-1H-tetrazole;

5-[2-[5-[[1-pentyl-3-(1,1-methoxybutyl)-1H-1,2,4-triazol-5-yl]methyl]-2-pyridinyl]phenyl]-1H-tetrazole;

5-[2-[5-[[1-pentyl-3-(1,1-dimethoxypentyl)-1H-1,2,4-triazol-5-yl]methyl]-2-pyridinyl]phenyl]-1H-tetrazole;

5-[2-[5-[[1-pentyl-3-(1-oxopropyl)-1H-1,2,4-triazol-5-yl]methyl]-2-pyridinyl]phenyl]-1H-tetrazole;

5-[2-[5-[[1-pentyl-3-(1-oxobutyl)-1H-1,2,4-triazol-5-yl]methyl]-2-pyridinyl]phenyl]-1H-tetrazole;

5-[2-[5-[[1-pentyl-3-(1-oxopentyl)-1H-1,2,4-triazol-5-yl]methyl]-2-pyridinyl]phenyl]-1H-tetrazole; and 5-[2-[5-[[1-pentyl-3-(1,1-difluorobutyl)-1H-1,2,4-triazol-5-yl]methyl]-2-pyridinyl]phenyl]-1H-tetrazole.

A family of specific compounds of more particular interest within Formula III consists of the following compounds:

5-[2-[5-[(1-butyl-3-methyl-1H-1,2,4-triazol-5-yl)methyl]-2-pyridinyl]phenyl]-1H-tetrazole;

5-[2-[5-[(1-butyl-3-ethyl-1H-1,2,4-triazol-5-yl)methyl]-2-pyridinyl]phenyl]-1H-tetrazole;

5-[2-[5-[(1-butyl-3-propyl-1H-1,2,4-triazol-5-yl)methyl]-2-pyridinyl]phenyl]-1H-tetrazole;

5-[2-[5-[(1-butyl-3-isopropyl-1H-1,2,4-triazol-5-yl)methyl]-2-pyridinyl]phenyl]-1H-tetrazole;

5-[2-[5-[(1,3-dibutyl-1H-1,2,4-triazol-5-yl)methyl]-2-pyridinyl]phenyl]-1H-tetrazole;

5-[2-[5-[(1-butyl-3-secbutyl-1H-1,2,4-triazol-5-yl)methyl]-2-pyridinyl]phenyl]-1H-tetrazole;

5-[2-[5-[(1-butyl-3-isobutyl-1H-1,2,4-triazol-5-yl)methyl]-2-pyridinyl]phenyl]-1H-tetrazole;
5-[2-[5-[(1-butyl-3-tertbutyl-1H-1,2,4-triazol-5-yl)methyl]-2-pyridinyl]phenyl]-1H-tetrazole;
5-[2-[5-[(1-butyl-3-pentyl-1H-1,2,4-triazol-5-yl)methyl]-2-pyridinyl]phenyl]-1H-tetrazole;
5-[2-[5-[(1-butyl-3-isopentyl-1H-1,2,4-triazol-5-yl)methyl]-2-pyridinyl]phenyl]-1H-tetrazole;
5-[2-[5-[(1-butyl-3-cyclohexyl-1H-1,2,4-triazol-5-yl)methyl]-2-pyridinyl]phenyl]-1H-tetrazole;
5-[2-[5-[(1-butyl-3-cyclohexylmethyl-1H-1,2,4-triazol-5-yl)methyl]-2-pyridinyl]phenyl]-1H-tetrazole;
5-[2-[5-[[1-butyl-3-(2-cyclohexylethyl)-1H-1,2,4-triazol-5-yl]methyl]-2-pyridinyl]phenyl]-1H-tetrazole;
5-[2-[5-[(1-butyl-3-phenyl-1H-1,2,4-triazol-5-yl)methyl]-2-pyridinyl]phenyl]-1H-tetrazole;
5-[2-[5-[(1-butyl-3-phenylmethyl-1H-1,2,4-triazol-5-yl)methyl]-2-pyridinyl]phenyl]-1H-tetrazole; and
5-[2-[5-[[1-butyl-3-(2-phenylethyl)-1H-1,2,4-triazol-5-yl]methyl]-2-pyridinyl]phenyl]-1H-tetrazole.

Another subclass of compounds of Formula I which is of even more particular interest consists of those compounds of Formula IV

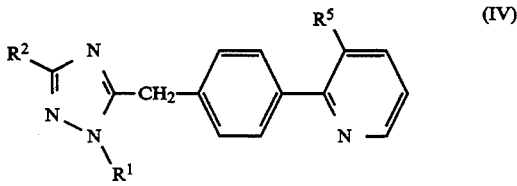

(IV)

wherein m is one; wherein $R^1$ is selected from methyl, ethyl, n-propyl, isopropyl, n-butyl, sec-butyl, isobutyl, tert-butyl, 4-methylbutyl, n-pentyl, neopentyl, phenyl, benzyl, phenethyl, cyclohexyl, cyclohexylmethyl, 2-butenyl, 3-butenyl, 2-butynyl, 3-butynyl and 2-hydroxybutyl; wherein $R^2$ is selected from ethyl, n-propyl, isopropyl, n-butyl, sec-butyl, isobutyl, 4-methylbutyl, n-pentyl, 1-oxo-2-phenylethyl, 1-oxo-2-cyclohexylethyl, 1,1-difluoro-2-phenylethyl, 1,1-difluoro-2-cyclohexylethyl, 2-cyclohexylethyl, 1,1-difluoro-3-cyclohexylpropyl, 1,1-dimethoxybutyl, 1,1-difluoroethyl, 1,1-difluoropropyl, 1,1-difluorobutyl, 1,1-difluoropentyl, benzyl, 2-phenylethyl, 1,1-difluoro-3-phenylpropyl, cyclohexylmethyl, cyclohexanoyl, 1-butenyl, 2-butenyl, 3-butenyl, 1-butynyl, 2-butynyl, 3-butynyl, propylthio and butylthio; wherein $R^5$ is an acidic group selected from $CO_2H$ and

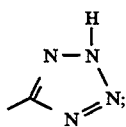

or a tautomer thereof or a pharmaceutically-acceptable salt thereof.

A family of specific compounds of particular interest within Formula IV consists of the following compounds:
2-[4-[(1-propyl-3-methyl-1H-1,2,4-triazol-5-yl)methyl]phenyl]-3-pyridinecarboxylic acid;
2-[4-[(1-propyl-3-ethyl-1H-1,2,4-triazol-5-yl)methyl]phenyl]-3-pyridinecarboxylic acid;
2-[4-[(1,3-dipropyl-1H-1,2,4-triazol-5-yl)methyl]phenyl]-3-pyridinecarboxylic acid;
2-[4-[(1-propyl-3-isopropyl-1H-1,2,4-triazol-5-yl)methyl]phenyl]-3-pyridinecarboxylic acid;
2-[4-[(1-propyl-3-butyl-1H-1,2,4-triazol-5-yl)methyl]phenyl]-3-pyridinecarboxylic acid;
2-[4-[(1-propyl-3-secbutyl-1H-1,2,4-triazol-5-yl)methyl]phenyl]-3-pyridinecarboxylic acid;
2-[4-[(1-propyl-3-isobutyl-1H-1,2,4-triazol-5-yl)methyl]phenyl]-3-pyridinecarboxylic acid;
2-[4-[(1-propyl-3-tertbutyl-1H-1,2,4-triazol-5-yl)methyl]phenyl]-3-pyridinecarboxylic acid;
2-[4-[(1-propyl-3-pentyl-1-1,2,4-triazol-5-yl)methyl]phenyl]-3-pyridinecarboxylic acid;
2-[4-[(1-propyl-3-isopentyl-1H-1,2,4-triazol-5-yl)methyl]phenyl]-3-pyridinecarboxylic acid;
2-[4-[(1-propyl-3-cyclohexyl-1H-1,2,4-triazol-5-yl)methyl]phenyl]-3-pyridinecarboxylic acid;
2-[4-[(1-propyl-3-cyclohexylmethyl-1H-1,2,4-triazol-5-yl)methyl]phenyl]-3-pyridinecarboxylic acid;
2-[4-[[1-propyl-3-(2-cyclohexylethyl)-1H-1,2,4-triazol-5-yl]methyl]phenyl]-3-pyridinecarboxylic acid;
2-[4-[(1-propyl-3-phenyl-1H-1,2,4-triazol-5-yl)methyl]phenyl]-3-pyridinecarboxylic acid;
2-[4-[(1-propyl-3-phenylmethyl-1H-1,2,4-triazol-5-yl)methyl]phenyl]-3-pyridinecarboxylic acid;
2-[4-[[1-propyl-3-(2-phenylethyl)-1H-1,2,4-triazol-5-yl]methyl]phenyl]-3-pyridinecarboxylic acid;
2-[4-[(1-propyl-3-cyclohexanoyl-1H-1,2,4-triazol-5-yl)methyl]phenyl]-3-pyridinecarboxylic acid;
2-[4-[[1-propyl-3-(1-oxo-2-cyclohexyethyl)-1H-1,2,4-triazol-5-yl]methyl]phenyl]-3-pyridinecarboxylic acid;
2-[4-[(1-propyl-3-benzoyl-1H-1,2,4-triazol-5-yl)methyl]phenyl]-3-pyridinecarboxylic acid;
2-[4-[[1-propyl-3-(1-oxo-2-phenylethyl)-1H-1,2,4-triazol-5-yl]methyl]phenyl]-3-pyridinecarboxylic acid;
2-[4-[[1-propyl-3-(1,1-dimethoxypropyl)-1H-1,2,4-triazol-5-yl]methyl]phenyl]-3-pyridinecarboxylic acid;
2-[4-[[1-propyl-3-(1,1-dimethoxybutyl)-1H-1,2,4-triazol-5-yl]methyl]phenyl]-3-pyridinecarboxylic acid;
2-[4-[[1-propyl-3-(1,1-dimethoxypentyl)-1H-1,2,4-triazol-5-yl]methyl]phenyl]-3-pyridinecarboxylic acid;
2-[4-[[1-propyl-3-(1-oxopropyl)-1H-1,2,4-triazol-5-yl]methyl]phenyl]-3-pyridinecarboxylic acid;
2-[4-[[1-propyl-3-(1-oxobutyl)-1H-1,2,4-triazol-5-yl]methyl]phenyl]-3-pyridinecarboxylic acid;
2-[4-[[i-propyl-3-(1-oxopentyl)-1H-1,2,4-triazol-5-yl]methyl]phenyl]-3-pyridinecarboxylic acid;
2-[4-[[1-propyl-3-(1,1-difluorobutyl)-1H-1,2,4-triazol-5-yl]methyl]phenyl]-3-pyridinecarboxylic acid;
2-[4-[(1-butyl-3-methyl-1H-1,2,4-triazol-5-yl)methyl]phenyl]-3-pyridinecarboxylic acid;
2-[4-[(1-butyl-3-ethyl-1H-1,2,4-triazol-5-yl)methyl]phenyl]-3-pyridinecarboxylic acid;
2-[4-[(1-butyl-3-propyl-1H-1,2,4-triazol-5-yl)methyl]phenyl]-3-pyridinecarboxylic acid;
2-[4-[(1-butyl-3-isopropyl-1H-1,2,4-triazol-5-yl)methyl]phenyl]-3-pyridinecarboxylic acid;
2-[4-[(1,3-dibutyl-1H-1,2,4-triazol-5-yl)methyl]phenyl]-3-pyridinecarboxylic acid;
2-[4-[(1-butyl-3-secbutyl-1H-1,2,4-triazol-5-yl)methyl]phenyl]-3-pyridinecarboxylic acid;
2-[4-[(1-butyl-3-isobutyl-1H-1,2,4-triazol-5-yl)methyl]phenyl]-3-pyridinecarboxylic acid;
2-[4-[(1-butyl-3-tertbutyl-1H-1,2,4-triazol-5-yl)methyl]phenyl]-3-pyridinecarboxylic acid;

2-[4-[(1-butyl-3-pentyl-1H-1,2,4-triazol-5-yl)methyl]-phenyl]-3-pyridinecarboxylic acid;
2-[4-[(1-butyl-3-isopentyl-1H-1,2,4-triazol-5-yl)methyl]-phenyl]-3-pyridinecarboxylic acid;
2-[4-[(1-butyl-3-cyclohexyl-1H-1,2,4-triazol-5-yl)methyl]phenyl]-3-pyridinecarboxylic acid;
2-[4-[(1-butyl-3-cyclohexylmethyl-1H-1,2,4-triazol-5-yl)methyl]phenyl]-3-pyridinecarboxylic acid;
2-[4-[[1-butyl-3-(2-cyclohexylethyl)-1H-1,2,4-triazol-5-yl]methyl]phenyl]-3-pyridinecarboxylic acid;
2-[4-[(1-butyl-3-phenyl-1H-1,2,4-triazol-5-yl)methyl]-phenyl]-3-pyridinecarboxylic acid;
2-[4-[(1-butyl-3-phenylmethyl-1H-1,2,4-triazol-5-yl)methyl]phenyl]-3-pyridinecarboxylic acid;
2-[4-[[1-butyl-3-(2-phenylethyl)-1H-1,2,4-triazol-5-yl]methyl]phenyl]-3-pyridinecarboxylic acid;
2-[4-[(1-butyl-3-cyclohexanoyl-1H-1,2,4-triazol-5-yl)methyl]phenyl]-3-pyridinecarboxylic acid;
2-[4-[[1-butyl-3-(1-oxo-2-cyclohexyethyl)-1H-1,2,4-triazol-5-yl]methyl]phenyl]-3-pyridinecarboxylic acid;
2-[4-[(1-butyl-3-benzoyl-1H-1,2,4-triazol-5-yl)methyl]-phenyl]-3-pyridinecarboxylic acid;
2-[4-[[1-butyl-3-(1-oxo-2-phenylethyl)-1H-1,2,4-triazol-5-yl]methyl]phenyl]-3-pyridinecarboxylic acid;
2-[4-[[1-butyl-3-(1,1-dimethoxypropyl)-1H-1,2,4-triazol-5-yl]methyl]phenyl]-3-pyridinecarboxylic acid;
2-[4-[[1-butyl-3-(1,1-dimethoxybutyl)-1H-1,2,4-triazol-5-yl]methyl]phenyl]-3-pyridinecarboxylic acid;
2-[4-[[1-butyl-3-(1,1-dimethoxypentyl)-1H-1,2,4-triazol-5-yl]methyl]phenyl]-3-pyridinecarboxylic acid;
2-[4-[[1-butyl-3-(1-oxopropyl)-1H-1,2,4-triazol-5-yl]methyl]phenyl]-3-pyridinecarboxylic acid;
2-[4-[[1-butyl-3-(1-oxobutyl)-1H-1,2,4-triazol-5-yl]methyl]phenyl]-3-pyridinecarboxylic acid;
2-[4-[[1-butyl-3-(1-oxopentyl)-1H-1,2,4-triazol-5-yl]methyl]phenyl]-3-pyridinecarboxylic acid;
2-[4-[[1-butyl-3-(1,1-difluorobutyl)-1H-1,2,4-triazol-5-yl]methyl]phenyl]-3-pyridinecarboxylic acid;
2-[4-[(1-pentyl-3-methyl-1H-1,2,4-triazol-5-yl)methyl]-phenyl]-3-pyridinecarboxylic acid;
2-[4-[(1-pentyl-3-ethyl-1H-1,2,4-triazol-5-yl)methyl]-phenyl]-3-pyridinecarboxylic acid;
2-[4-[(1-pentyl-3-propyl-1H-1,2,4-triazol-5-yl)methyl]-phenyl]-3-pyridinecarboxylic acid;
2-[4-[(1-pentyl-3-isopropyl-1H-1,2,4-triazol-5-yl)methyl]phenyl]-3-pyridinecarboxylic acid;
2-[4-[(1-pentyl-3-butyl-1H-1,2,4-triazol-5-yl)methyl]-phenyl]-3-pyridinecarboxylic acid;
2-[4-[(1-pentyl-3-secbutyl-1H-1,2,4-triazol-5-yl)methyl]-phenyl]-3-pyridinecarboxylic acid;
2-[4-[(1-pentyl-3-isobutyl-1H-1,2,4-triazol-5-yl)methyl]-phenyl]-3-pyridinecarboxylic acid;
2-[4-[(1-pentyl-3-tertbutyl-1H-1,2,4-triazol-5-yl)methyl]phenyl]-3-pyridinecarboxylic acid;
2-[4-[(1,3-dipentyl-1H-1,2,4-triazol-5-yl)methyl]-phenyl]-3-pyridinecarboxylic acid;
2-[4-[(1-pentyl-3-isopentyl-1H-1,2,4-triazol-5-yl)methyl]phenyl]-3-pyridinecarboxylic acid;
2-[4-[(1-pentyl-3-cyclohexyl-1H-1,2,4-triazol-5-yl)methyl]phenyl]-3-pyridinecarboxylic acid;
2-[4-[(1-pentyl-3-cyclohexylmethyl-1H-1,2,4-triazol-5-yl)methyl]phenyl]-3-pyridinecarboxylic acid;
2-[4-[[1-pentyl-3-(2-cyclohexylethyl)-1H-1,2,4-triazol-5-yl]methyl]phenyl]-3-pyridinecarboxylic acid;
2-[4-[(1-pentyl-3-phenyl-1H-1,2,4-triazol-5-yl)methyl]-phenyl]-3-pyridinecarboxylic acid;
2-[4-[(1-pentyl-3-phenylmethyl-1H-1,2,4-triazol-5-yl)methyl]phenyl]-3-pyridinecarboxylic acid;
2-[4-[[1-pentyl-3-(2-phenylethyl)-1H-1,2,4-triazol-5-yl]methyl]phenyl]-3-pyridinecarboxylic acid;
2-[4-[(1-pentyl-3-cyclohexanoyl-1H-1,2,4-triazol-5-yl)methyl]phenyl]-3-pyridinecarboxylic acid;
2-[4-[[1-pentyl-3-(1-oxo-2-cyclohexyethyl)-1H-1,2,4-triazol-5-yl]methyl]phenyl]-3-pyridinecarboxylic acid;
2-[4-[(1-pentyl-3-benzoyl-1H-1,2,4-triazol-5-yl)methyl]-phenyl]-3-pyridinecarboxylic acid;
2-[4-[[1-pentyl-3-(1-oxo-2-phenylethyl)-1H-1,2,4-triazol-5-yl]methyl]phenyl]-3-pyridinecarboxylic acid;
2-[4-[[1-pentyl-3-(1,1-dimethoxypropyl)-1H-1,2,4-triazol-5-yl]methyl]phenyl]-3-pyridinecarboxylic acid;
2-[4-[[1-pentyl-3-(1,1-dimethoxybutyl)-1H-1,2,4-triazol-5-yl]methyl]phenyl]-3-pyridinecarboxylic acid;
2-[4-[[1-pentyl-3-(1,1-dimethoxypentyl)-1H-1,2,4-triazol-5-yl]methyl]phenyl]-3-pyridinecarboxylic acid;
2-[4-[[1-pentyl-3-(1-oxopropyl)-1H-1,2,4-triazol-5-yl]methyl]phenyl]-3-pyridinecarboxylic acid;
2-[4-[[1-pentyl-3-(t-oxobutyl)-1H-1,2,4-triazol-5-yl]methyl]phenyl]-3-pyridinecarboxylic acid;
2-[4-[[1-pentyl-3-(1-oxopentyl)-1H-1,2,4-triazol-5-yl]methyl]phenyl]-3-pyridinecarboxylic acid;
2-[4-[[1-pentyl-3-(1,1-difluorobutyl)-1H-1,2,4-triazol-5-yl]methyl]phenyl]-3-pyridinecarboxylic acid;
5-[2-[4-[(1-propyl-3-methyl-1H-1,2,4-triazol-5-yl)methyl]phenyl]-3-pyridinyl]-1H-tetrazole;
5-[2-[4-[(1-propyl-3-ethyl-1H-1,2,4-triazol-5-yl)methyl]-phenyl]-3-pyridinyl]-1H-tetrazole;
5-[2-[4-[(1,3-dipropyl-1H-1,2,4-triazol-5-yl)methyl]-phenyl]-3-pyridinyl]-1H-tetrazole;
5-[2-[4-[(1-propyl-3-isopropyl-1H-1,2,4-triazol-5-yl)methyl]phenyl]-3-pyridinyl]-1H-tetrazole;
5-[2-[4-[(1-propyl-3-butyl-1H-1,2,4-triazol-5-yl)methyl]-phenyl]-3-pyridinyl]-1H-tetrazole;
5-[2-[4-[(1-propyl-3-secbutyl-1H-1,2,4-triazol-5-yl)methyl]phenyl]-3-pyridinyl]-1H-tetrazole;
5-[2-[4-[(1-propyl-3-isobutyl-1H-1,2,4-triazol-5-yl)methyl]phenyl]-3-pyridinyl]-1H-tetrazole;
5-[2-[4-[(1-propyl-3-tertbutyl-1H-1,2,4-triazol-5-yl)methyl]phenyl]-3-pyridinyl]-1H-tetrazole;
5-[2-[4-[(1-propyl-3-pentyl-1H-1,2,4-triazol-5-yl)methyl]phenyl]-3-pyridinyl]-1H-tetrazole;
5-[2-[4-[(1-propyl-3-isopentyl-1H-1,2,4-triazol-5-yl)methyl]phenyl]-3-pyridinyl]-1H-tetrazole;
5-[2-[4-[(1-propyl-3-cyclohexyl-1H-1,2,4-triazol-5-yl)methyl]phenyl]-3-pyridinyl]-1H-tetrazole;
5-[2-[4-[(1-propyl-3-cyclohexylmethyl-1H-1,2,4-triazol-5-yl)methyl]phenyl]-3-pyridinyl]-1H-tetrazole;
5-[2-[4-[[1-propyl-3-(2-cyclohexylethyl)-1H-1,2,4-triazol-5-yl]methyl]phenyl]-3-pyridinyl]-1H-tetrazole;
5-[2-[4-[(1-propyl-3-phenyl-1H-1,2,4-triazol-5-yl)methyl]phenyl]-3-pyridinyl]-1H-tetrazole;
5-[2-[4-[(1-propyl-3-phenylmethyl-1H-1,2,4-triazol-5-yl)methyl]phenyl]-3-pyridinyl]-1H-tetrazole;
5-[2-[4-[[1-propyl-3-(2-phenylethyl)-1H-1,2,4-triazol-5-yl]methyl]phenyl]-3-pyridinyl]-1H-tetrazole;
5-[2-[4-[(1-propyl-3-cyclohexanoyl-1H-1,2,4-triazol-5-yl)methyl]phenyl]-3-pyridinyl]-1H-tetrazole;
5-[2-[4-[[1-propyl-3-(1-oxo-2-cyclohexylethyl)-1H-1,2,4-triazol-5-yl]methyl]phenyl]-3-pyridinyl]-1H-tetrazole;

5-[2-[4-[(1-propyl-3-benzoyl-1H-1,2,4-triazol-5-yl)methyl]phenyl]-3-pyridinyl]-1H-tetrazole;
5-[2-[4-[[1-propyl-3-(1-oxo-2-phenylethyl)-1H-1,2,4-triazol-5-yl]methyl]phenyl]-3-pyridinyl]-1H-tetrazole;
5-[2-[4-[[1-propyl-3-(1,1-dimethoxypropyl)-1H-1,2,4-triazol-5-yl]methyl]phenyl]-3-pyridinyl]-1H-tetrazole;
5-[2-[4-[[1-propyl-3-(1,1-dimethoxypentyl)-1H-1,2,4-triazol-5-yl]methyl]phenyl]-3-pyridinyl]-1H-tetrazole;
5-[2-[4-[(1-propyl-3-(1,1-dimethoxybutyl)-1H-1,2,4triazol-5-yl)methyl]phenyl]-3-pyridinyl]-1H-tetrazole;
5-[2-[4-[[1-propyl-3-(1-oxopropyl)-1H-1,2,4-triazol-5-yl]methyl]phenyl]-3-pyridinyl]-1H-tetrazole;
5-[2-[4-[[1-propyl-3-(1-oxobutyl)-1H-1,2,4-triazol-5-yl]methyl]phenyl]-3-pyridinyl]-1H -tetrazole;
5-[2-[4-[[1-propyl-3-(1-oxopentyl)-1H-1,2,4-triazol-5-yl]methyl]phenyl]-3-pyridinyl]-1H-tetrazole;
5-[2-[4-[[1-propyl-3-(1,1-difluorobutyl)-1H-1,2,4-triazol-5-yl]methyl]phenyl]-3-pyridinyl]-1H-tetrazole;
5-[2-[4-[(1-butyl-3-methyl-1H-1,2,4-triazol-5-yl)methyl]phenyl]-3-pyridinyl]-1H-tetrazole;
5-[2-[4-[(1-butyl-3-ethyl-1H-1,2,4-triazol-5-yl)methyl]phenyl]-3-pyridinyl]-1H-tetrazole;
5-[2-[4-[(1-butyl-3-propyl-1H-1,2,4-triazol-5-yl)methyl]phenyl]-3-pyridinyl]-1H-tetrazole;
5-[2-[4-[(1-butyl-3-isopropyl-1H-1,2,4-triazol-5-yl)methyl]phenyl]-3-pyridinyl]-1H-tetrazole;
5-[2-[4-[(1,3-dibutyl-1H-1,2,4-triazol-5-yl)methyl]phenyl]-3-pyridinyl]-1H-tetrazole;
5-[2-[4-[(1-butyl-3-secbutyl-1H-1,2,4-triazol-5-yl)methyl]phenyl]-3-pyridinyl]-1H-tetrazole;
5-[2-[4-[(1-butyl-3-isobutyl-1H-1,2,4-triazol-5-yl)methyl]phenyl]-3-pyridinyl]-1H-tetrazole;
5-[2-[4-[(1-butyl-3-tertbutyl-1H-1,2,4-triazol-5-yl)methyl]phenyl]-3-pyridinyl]-1H-tetrazole;
5-[2-[4-[(1-butyl-3-pentyl-1H-1,2,4-triazol-5-yl)methyl]phenyl]-3-pyridinyl]-1H-tetrazole;
5-[2-[4-[(1-butyl-3-isopentyl-1H-1,2,4-triazol-5-yl)methyl]phenyl]-3-pyridinyl]-1H-tetrazole;
5-[2-[4-[(1-butyl-3-cyclohexyl-1H-1,2,4-triazol-5-yl)methyl]phenyl]-3-pyridinyl]-1H-tetrazole;
5-[2-[4-[(1-butyl-3-cyclohexylmethyl-1H-1,2,4-triazol-5-yl)methyl]phenyl]-3-pyridinyl]-1H-tetrazole;
5-[2-[4-[[1-butyl-3-(2-cyclohexylethyl)-1H-1,2,4-triazol-5-yl]methyl]phenyl]-3-pyridinyl]-1H-tetrazole;
5-[2-[4-[(1-butyl-3-phenyl-1H-1,2,4-triazol-5-yl)methyl]phenyl]-3-pyridinyl]-1H-tetrazole;
5-[2-[4-[(1-butyl-3-phenylmethyl-1H-1,2,4-triazol-5-yl)methyl]phenyl]-3-pyridinyl]-1H-tetrazole;
5-[2-[4-[[1-butyl-3-(2-phenylethyl)-1H-1,2,4-triazol-5-yl]methyl]phenyl]-3-pyridinyl]-1H-tetrazole;
5-[2-[4-[(1-butyl-3-cyclohexanoyl-1H-1,2,4-triazol-5-yl)methyl]phenyl]-3-pyridinyl]-1H-tetrazole;
5-[2-[4-[[1-butyl-3-(1-oxo-2-cyclohexylethyl)-1H-1,2,4-triazol-5-yl]methyl]phenyl]-3-pyridinyl]-1H-tetrazole;
5-[2-[4-[(1-butyl-3-benzoyl-1H-1,2,4-triazol-5-yl)methyl]phenyl]-3-pyridinyl]-1H-tetrazole;
5-[2-[4-[[1-butyl-3-(1-oxo-2-phenylethyl)-1H-1,2,4-triazol-5-yl]methyl]phenyl]-3-pyridinyl]-1H-tetrazole;
5-[2-[4-[[1-butyl-3-(1,1-dimethoxypropyl)-1H-1,2,4-triazol-5-yl]methyl]phenyl]-3-pyridinyl]-1H-tetrazole;
5-[2-[4-[[1-butyl-3-(1,1-dimethoxypentyl)-1H-1,2,4-triazol-5-yl]methyl]phenyl]-3-pyridinyl]-1H-tetrazole;
5-[2-[4-[(1-butyl-3-(1,1-dimethoxybutyl)-1H-1,2,4-triazol-5-yl)methyl]phenyl]-3-pyridinyl]-1H-tetrazole;
5-[2-[4-[[1-butyl-3-(1-oxopropyl)-1H-1,2,4-triazol-5-yl]methyl]phenyl]-3-pyridinyl]-1H-tetrazole;
5-[2-[4-[[1-butyl-3-(1-oxobutyl)-1H-1,2,4-triazol-5-yl]methyl]phenyl]-3-pyridinyl]-1H-tetrazole;
5-[2-[4-[[1-butyl-3-(1-oxopentyl)-1H-1,2,4-triazol-5-yl]methyl]phenyl]-3-pyridinyl]-1H-tetrazole;
5-[2-[4-[[1-butyl-3-(1,1-difluorobutyl)-1H-1,2,4-triazol-5-yl]methyl]phenyl]-3-pyridinyl]-1H-tetrazole;
5-[2-[4-[(1-pentyl-3-methyl-1H-1,2,4-triazol-5-yl)methyl]phenyl]-3-pyridinyl]-1H-tetrazole;
5-[2-[4-[(1-pentyl-3-ethyl-1H-1,2,4-triazol-5-yl)methyl]phenyl]-3-pyridinyl]-1H-tetrazole;
5-[2-[4-[(1-pentyl-3-propyl-1H-1,2,4-triazol-5-yl)methyl]phenyl]-3-pyridinyl]-1H-tetrazole;
5-[2-[4-[(1-pentyl-3-isopropyl-1H-1,2,4-triazol-5-yl)methyl]phenyl]-3-pyridinyl]-1H-tetrazole;
5-[2-[4-[(1-pentyl-3-butyl-1H-1,2,4-triazol-5-yl)methyl]phenyl]-3-pyridinyl]-1H-tetrazole;
5-[2-[4-[(1-pentyl-3-secbutyl-1H-1,2,4-triazol-5-yl)methyl]phenyl]-3-pyridinyl]-1H-tetrazole;
5-[2-[4-[(1-pentyl-3-isobutyl-1H-1,2,4-triazol-5-yl)methyl]phenyl]-3-pyridinyl]-1H-tetrazole;
5-[2-[4-[(1-pentyl-3-tertbutyl-1H-1,2,4-triazol-5-yl)methyl]phenyl]-3-pyridinyl]-1H-tetrazole;
5-[2-[4-[(1,3-dipentyl-1H-1,2,4-triazol-5-yl)methyl]phenyl]-3-pyridinyl]-1H-tetrazole;
5-[2-[4-[(1-pentyl-3-isopentyl-1H-1,2,4-triazol-5-yl)methyl]phenyl]-3-pyridinyl]-1H-tetrazole;
5-[2-[4-[(1-pentyl-3-cyclohexyl-1H-1,2,4-triazol-5-yl)methyl]phenyl]-3-pyridinyl]-1H-tetrazole;
5-[2-[4-[(1-pentyl-3-cyclohexylmethyl-1H-1,2,4-triazol-5-yl)methyl]phenyl]-3-pyridinyl]-1H-tetrazole;
5-[2-[4-[[1-pentyl-3-(2-cyclohexylethyl)-1H-1,2,4-triazol-5-yl]methyl]phenyl]-3-pyridinyl]-1H-tetrazole;
5-[2-[4-[(1-pentyl-3-phenyl-1H-1,2,4-triazol-5-yl)methyl]phenyl]-3-pyridinyl]-1H-tetrazole;
5-[2-[4-[(1-pentyl-3-phenylmethyl-1H-1,2,4-triazol-5-yl)methyl]phenyl]-3-pyridinyl]-1H-tetrazole;
5-[2-[4-[[1-pentyl-3-(2-phenylethyl)-1H-1,2,4-triazol-5-yl]methyl]phenyl]-3-pyridinyl]-1H-tetrazole;
5-[2-[4-[(1-pentyl-3-cyclohexanoyl-1H-1,2,4-triazol-5-yl)methyl]phenyl]-3-pyridinyl]-1H-tetrazole;
5-[2-[4-[[1-pentyl-3-(1-oxo-2-cyclohexylethyl)-1H-1,2,4-triazol-5-yl]methyl]phenyl]-3-pyridinyl]-1H-tetrazole;
5-[2-[4-[(1-pentyl-3-benzoyl-1H-1,2,4-triazol-5-yl)methyl]phenyl]-3-pyridinyl]-1H-tetrazole;
5-[2-[4-[[1-pentyl-3-(i-oxo-2-phenylethyl)-1H-1,2,4-triazol-5-yl]methyl]phenyl]-3-pyridinyl]-1H-tetrazole;
5-[2-[4-[[1-pentyl-3-(1,1-dimethoxypropyl)-1H-1,2,4-triazol-5-yl]methyl]phenyl]-3-pyridinyl]-1H-tetrazole;
5-[2-[4-[[1-pentyl-3-(1,1-dimethoxypentyl)-1H-1,2,4-triazol-5-yl]methyl]phenyl]-3-pyridinyl]-1H-tetrazole;
5-[2-[4-[(1-pentyl-3-(1,1-dimethoxybutyl)-1H-1,2,4-triazol-5-yl) methyl]phenyl]-3-pyridinyl]-1H-tetrazole;
5-[2-[4-[[1-pentyl-3-(1-oxopropyl)-1H-1,2,4-triazol-5-yl]methyl]phenyl]-3-pyridinyl]-1H-tetrazole;

5-[2-[4-[[1-pentyl-3-(1-oxobutyl)-1H-1,2,4-triazol-5-yl]methyl]phenyl]-3-pyridinyl]-1H-tetrazole;
5-[2-[4-[[1-pentyl-3-(1-oxopentyl)-1H-1,2,4-triazol-5yl]-methyl]phenyl]-3-pyridinyl]-1H-tetrazole; and
5-[2-[4-[[1-pentyl-3-(1,1-difluorobutyl)-1H-1,2,4-triazol-5-yl]methyl]phenyl]-3-pyridinyl]-1H-tetrazole.

A family of specific compounds of more particular interest within Formula IV consists of
5-[2-[4-[(1-butyl-3-methyl-1H-1,2,4-triazol-5-yl)methyl]phenyl]-3-pyridinyl]-1H-tetrazole;
5-[2-[4-[(1-butyl-3-ethyl-1H-1,2,4-triazol-5-yl)methyl]phenyl]-3-pyridinyl]-1H-tetrazole;
5-[2-[4-[(1-butyl-3-propyl-1H-1,2,4-triazol-5-yl)methyl]phenyl]-3-pyridinyl]-1H-tetrazole;
5-[2-[4-[(1-butyl-3-isopropyl-1H-1,2,4-triazol-5-yl)methyl]phenyl]-3-pyridinyl]-1H-tetrazole;
5-[2-[4-[(1,3-dibutyl-1H-1,2,4-triazol-5-yl)methyl]phenyl]-3-pyridinyl]-1H-tetrazole;
5-[2-[4-[(1-butyl-3-secbutyl-1H-1,2,4-triazol-5-yl)methyl]phenyl]-3-pyridinyl]-1H-tetrazole;
5-[2-[4-[(1-butyl-3-isobutyl-1H-1,2,4-triazol-5-yl)methyl]phenyl]-3-pyridinyl]-1H-tetrazole;
5-[2-[4-[(1-butyl-3-tertbutyl-1H-1,2,4-triazol-5-yl)methyl]phenyl]-3-pyridinyl]-1H-tetrazole;
5-[2-[4-[(1-butyl-3-pentyl-1H-1,2,4-triazol-5-yl)methyl]phenyl]-3-pyridinyl]-1H-tetrazole;
5-[2-[4-[(1-butyl-3-isopentyl-1H-1,2,4-triazol-5-yl)methyl]phenyl]-3-pyridinyl]-1H-tetrazole;
5-[2-[4-[(1-butyl-3-cyclohexyl-1H-1,2,4-triazol-5-yl)methyl]phenyl]-3-pyridinyl]-1H-tetrazole;
5-[2-[4-[(1-butyl-3-cyclohexylmethyl-1H-1,2,4-triazol-5-yl)methyl]phenyl]-3-pyridinyl]-1H-tetrazole;
5-[2-[4-[[1-butyl-3-(2-cyclohexylethyl)-1H-1,2,4-triazol-5-yl]methyl]phenyl]-3-pyridinyl]-1H-tetrazole;
5-[2-[4-[(1-butyl-3-phenyl-1H-1,2,4-triazol-5-yl)methyl]phenyl]-3-pyridinyl]-1H-tetrazole;
5-[2-[4-[(1-butyl-3-phenylmethyl-1H-1,2,4-triazol-5-yl)methyl]phenyl]-3-pyridinyl]-1H-tetrazole; and
5-[2-[4-[[1-butyl-3-(2-phenylethyl)-1H-1,2,4-triazol-5-yl]methyl]phenyl]-3-pyridinyl]-1H-tetrazole.

Another subclass of compounds of Formula I which is of even more particular interest consists of those compounds of Formula V

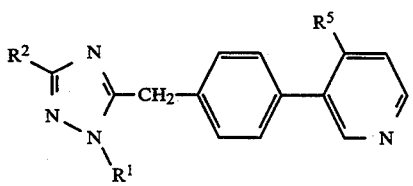

wherein m is one; wherein $R^1$ is selected from methyl, ethyl, n-propyl, isopropyl, n-butyl, sec-butyl, isobutyl, tert-butyl, 4-methylbutyl, n-pentyl, neopentyl, phenyl, benzyl, phenethyl, cyclohexyl, cyclohexylmethyl, 2-butenyl, 3-butenyl, 2-butynyl, 3-butynyl and 2-hydroxybutyl; wherein $R^2$ is selected from ethyl, n-propyl, isopropyl, n-butyl, sec-butyl, isobutyl, 4-methylbutyl, n-pentyl, 1-oxo-2-phenylethyl, 1-oxo-2-cyclohexylethyl, 1,1-difluoro-2-phenylethyl, 1,1-difluoro-2-cyclohexylethyl, 2-cyclohexylethyl, 1,1-difluoro-3-cyclohexylpropyl, 1,1-dimethoxybutyl, 1,1-difluoroethyl, 1,1-difluoropropyl, 1,1-difluorobutyl, 1,1-difluoropentyl, benzyl, 2-phenylethyl, 1,1-difluoro-3-phenylpropyl, cyclohexylmethyl, cyclohexanoyl, 1-butenyl, 2-butenyl, 3-butenyl, 1-butynyl, 2-butynyl, 3-butynyl, propylthio and butylthio; wherein $R^5$ is an acidic group selected from $CO_2H$ and

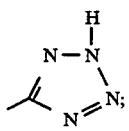

or a tautomer thereof or a pharmaceutically-acceptable salt thereof.

A family of specific compounds of particular interest within Formula V consists of the following compounds:
3-[4-[(1-propyl-3-methyl-1H-1,2,4-triazol-5-yl)methyl]phenyl]-4-pyridinecarboxylic acid;
3-[4-[(1-propyl-3-ethyl-1H-1,2,4-triazol-5-yl)methyl]phenyl]-4-pyridinecarboxylic acid;
3-[4-[(1,3-dipropyl-1H-1,2,4-triazol-5-yl)methyl]phenyl]-4-pyridinecarboxylic acid;
3-[4-[(1-propyl-3-isopropyl-1H-1,2,4-triazol-5-yl)methyl]phenyl]-4-pyridinecarboxylic acid;
3-[4-[(1-propyl-3-butyl-1H-1,2,4-triazol-5-yl)methyl]phenyl]-4-pyridinecarboxylic acid;
3-[4-[(1-propyl-3-secbutyl-1H-1,2,4-triazol-5-yl)methyl]phenyl]-4-pyridinecarboxylic acid;
3-[4-[(1-propyl-3-isobutyl-1H-1,2,4-triazol-5-yl)methyl]phenyl]-4-pyridinecarboxylic acid;
3-[4-[(1-propyl-3-tertbutyl-1H-1,2,4-triazol-5-yl)methyl]phenyl]-4-pyridinecarboxylic acid;
3-[4-[(1-propyl-3-pentyl-1H-1,2,4-triazol-5-yl)methyl]phenyl]-4-pyridinecarboxylic acid;
3-[4-[(1-propyl-3-isopentyl-1H-1,2,4-triazol-5-yl)methyl]phenyl]-4-pyridinecarboxylic acid;
3-[4-[(1-propyl-3-cyclohexyl-1H-1,2,4-triazol-5-yl)methyl]phenyl]-4-pyridinecarboxylic acid;
3-[4-[(1-propyl-3-cyclohexylmethyl-1H-1,2,4-triazol-5-yl)methyl]phenyl]-4-pyridinecarboxylic acid;
3-[4-[[1-propyl-3-(2-cyclohexylethyl)-1H-1,2,4-triazol-5-yl]methyl]phenyl]-4-pyridinecarboxylic acid;
3-[4-[(1-propyl-3-phenyl-1H-1,2,4-triazol-5-yl)methyl]phenyl]-4-pyridinecarboxylic acid;
3-[4-[(1-propyl-3-phenylmethyl-1H-1,2,4-triazol-5-yl)methyl]phenyl]-4-pyridinecarboxylic acid;
3-[4-[[1-propyl-3-(2-phenylethyl)-1H-1,2,4-triazol-5-yl]methyl]phenyl]-4-pyridinecarboxylic acid;
3-[4-[(1-propyl-3-cyclohexanoyl-1H-1,2,4-triazol-5-yl)methyl]phenyl]-4-pyridinecarboxylic acid;
3-[4-[[1-propyl-3-(1-oxo-2-cyclohexylethyl)-1H-1,2,4-triazol-5-yl]methyl]phenyl]-4-pyridinecarboxylic acid;
3-[4-[(1-propyl-3-benzoyl-1H-1,2,4-triazol-5-yl)methyl]phenyl]-4-pyridinecarboxylic acid;
3-[4-[[1-propyl-3-(1-oxo-2-phenylethyl)-1H-1,2,4-triazol-5-yl]methyl]phenyl]-4-pyridinecarboxylic acid;
3-[4-[[1-propyl-3-(1,1-dimethoxypropyl)-1H-1,2,4-triazol-5-yl]methyl]phenyl]-4-pyridinecarboxylic acid;
3-[4-[[1-propyl-3-(1,1-dimethoxybutyl)-1H-1,2,4-triazol-5-yl]methyl]phenyl]-4-pyridinecarboxylic acid;
3-[4-[[1-propyl-3-(1,1-dimethoxypentyl)-1H-1,2,4-triazol-5-yl]methyl]phenyl]-4-pyridinecarboxylic acid;
3-[4-[[1-propyl-3-(1-oxopropyl)-1H-1,2,4-triazol-5-yl]methyl]phenyl]-4-pyridinecarboxylic acid;
3-[4-[[1-propyl-3-(1-oxobutyl)-1H-1,2,4-triazol-5-yl]methyl]phenyl]-4-pyridinecarboxylic acid;

3-[4-[[1-propyl-3-(1-oxopentyl)-1H-1,2,4-triazol-5-yl]methyl]phenyl]-4-pyridinecarboxylic acid;
3-[4-[[1-propyl-3-(1,1-difluorobutyl)-1H-1,2,4-triazol-5-yl]methyl]phenyl]-4-pyridinecarboxylic acid;
3-[4-[(1-butyl-3-methyl-1H-1,2,4-triazol-5-yl)methyl]phenyl]-4-pyridinecarboxylic acid;
3-[4-[(1-butyl-3-ethyl-1H-1,2,4-triazol-5-yl)methyl]phenyl]-4-pyridinecarboxylic acid;
3-[4-[(1-butyl-3-propyl-1H-1,2,4-triazol-5-yl)methyl]phenyl]-4-pyridinecarboxylic acid;
3-[4-[(1-butyl-3-isopropyl-1H-1,2,4-triazol-5-yl)methyl]phenyl]-4-pyridinecarboxylic acid;
3-[4-[(1,3-dibutyl-1H-1,2,4-triazol-5-yl)methyl]phenyl]-4-pyridinecarboxylic acid;
3-[4-[(1-butyl-3-secbutyl-1H-1,2,4-triazol-5-yl)methyl]phenyl]-4-pyridinecarboxylic acid;
3-[4-[(1-butyl-3-isobutyl-1H-1,2,4-triazol-5-yl)methyl]phenyl]-4-pyridinecarboxylic acid;
3-[4-[(1-butyl-3-tertbutyl-1H-1,2,4-triazol-5-yl)methyl]phenyl]-4-pyridinecarboxylic acid;
3-[4-[(1-butyl-3-pentyl-1H-1,2,4-triazol-5-yl)methyl]phenyl]-4-pyridinecarboxylic acid;
3-[4-[(1-butyl-3-isopentyl-1H-1,2,4-triazol-5-yl)methyl]phenyl]-4-pyridinecarboxylic acid;
3-[4-[(1-butyl-3-cyclohexyl-1H-1,2,4-triazol-5-yl)methyl]phenyl]-4-pyridinecarboxylic acid;
3-[4-[(1-butyl-3-cyclohexylmethyl-1H-1,2,4-triazol-5-yl)methyl]phenyl]-4-pyridinecarboxylic acid;
3-[4-[[1-butyl-3-(2-cyclohexylethyl)-1H-1,2,4-triazol-5-yl]methyl]phenyl]-4-pyridinecarboxylic acid;
3-[4-[(1-butyl-3-phenyl-1H-1,2,4-triazol-5-yl)methyl]phenyl]-4-pyridinecarboxylic acid;
3-[4-[(1-butyl-3-phenylmethyl-1H-1,2,4-triazol-5-yl)methyl]phenyl]-4-pyridinecarboxylic acid;
3-[4-[[1-butyl-3-(2-phenylethyl)-1H-1,2,4-triazol-5-yl]methyl]phenyl]-4-pyridinecarboxylic acid;
3-[4-[(1-butyl-3-cyclohexanoyl-1H-1,2,4-triazol-5-yl)methyl]phenyl]-4-pyridinecarboxylic acid;
3-[4-[[l-butyl-3-(1-oxo-2-cyclohexylethyl)-1H-1,2,4-triazol-5-yl]methyl]phenyl]-4-pyridinecarboxylic acid;
3-[4-[(1-butyl-3-benzoyl-1H-1,2,4-triazol-5-yl)methyl]phenyl]-4-pyridinecarboxylic acid;
3-[4-[[i-butyl-3-(1-oxo-2-phenylethyl)-1H-1,2,4-triazol-5-yl]methyl]phenyl]-4-pyridinecarboxylic acid;
3-[4-[[1-butyl-3-(1,1-dimethoxypropyl)-1H-1,2,4-triazol-5-yl]methyl]phenyl]-4-pyridinecarboxylic acid;
3-[4-[[1-butyl-3-(1,1-dimethoxybutyl)-1H-1,2,4-triazol-5-yl]methyl]phenyl]-4-pyridinecarboxylic acid;
3-[4-[[1-butyl-3-(1,1-dimethoxybutyl)-1H-1,2,4-triazol-5-yl]methyl]phenyl]-4-pyridinecarboxylic acid;
3-[4-[[1-butyl-3-(1-oxopropyl)-1H-1,2,4-triazol-5-yl]methyl]phenyl]-4-pyridinecarboxylic acid;
3-[4-[[1-butyl-3-(1-oxobutyl)-1H-1,2,4-triazol-5-yl]methyl]phenyl]-4-pyridinecarboxylic acid;
3-[4-[[1-butyl-3-(1-oxopentyl)-1H-1,2,4-triazol-5-yl]methyl]phenyl]-4-pyridinecarboxylic acid;
3-[4-[[1-butyl-3-(1-difluorobutyl)-1H-1,2,4-triazol-5-yl]methyl]phenyl]-4-pyridinecarboxylic acid;
3-[4-[(1-pentyl-3-methyl-1H-1,2,4-triazol-5-yl)methyl]phenyl]-4-pyridinecarboxylic acid;
3-[4-[(1-pentyl-3-ethyl-1H-1,2,4-triazol-5-yl)methyl]phenyl]-4-pyridinecarboxylic acid;
3-[4-[(1-pentyl-3-propyl-1H-1,2,4-triazol-5)methyl]phenyl]-4-pyridinecarboxylic acid;
3-[4-[(1-pentyl-3-isopropyl-1H-1,2,4-triazol-5-yl)methyl]phenyl]-4-pyridinecarboxylic acid;
3-[4-[(1-pentyl-3-butyl-1H-1,2,4-triazol-5-yl)methyl]phenyl]-4-pyridinecarboxylic acid;
3-[4-[(1-pentyl-3-secbutyl-1H-1,2,4-triazol-5-yl)methyl]phenyl]-4-pyridinecarboxylic acid;
3-[4-[(1-pentyl-3-isobutyl-1H-1,2,4-triazol-5-yl)methyl]phenyl]-4-pyridinecarboxylic acid;
3-[4-[(1-pentyl-3-tertbutyl-1H-1,2,4-triazol-5-yl)methyl]phenyl]-4-pyridinecarboxylic acid;
3-[4-[(1,3-dipentyl-1H-1,2,4-triazol-5-yl)methyl]phenyl]-4-pyridinecarboxylic acid;
3-[4-[(1-pentyl-3-isopentyl-1H-1,2,4-triazol-5-yl)methyl]phenyl]-4-pyridinecarboxylic acid;
3-[4-[(1-pentyl-3-cyclohexyl-1H-1,2,4-triazol-5-yl)methyl]phenyl]-4-pyridinecarboxylic acid;
3-[4-[(1-pentyl-3-cyclohexylmethyl-1H-1,2,4-triazol-5-yl)methyl]phenyl]-4-pyridinecarboxylic acid;
3-[4-[[1-pentyl-3-(2-cyclohexylethyl)-1H-1,2,4-triazol-5-yl]methyl]phenyl]-4-pyridinecarboxylic acid;
3-[4-[(1-pentyl-3-phenyl-1H-1,2,4-triazol-5-yl)methyl]phenyl]-4-pyridinecarboxylic acid;
3-[4-[(1-pentyl-3-phenylmethyl-1H-1,2,4-triazol-5-yl)methyl]phenyl]-4-pyridinecarboxylic acid;
3-[4-[[1-pentyl-3-(2-phenylethyl)-1H-1,2,4-triazol-5-yl]methyl]phenyl]-4-pyridinecarboxylic acid;
3-[4-[(1-pentyl-3-cyclohexanoyl-1H-1,2,4-triazol-5-yl)methyl]phenyl]-4-pyridinecarboxylic acid;
3-[4-[[1-pentyl-3-(1-oxo-2-cyclohexylethyl)-1H-1,2,4-triazol-5-yl]methyl]phenyl]-4-pyridinecarboxylic acid;
3-[4-[(1-pentyl-3-benzoyl-1H-1,2,4-triazol-5-yl)methyl]phenyl]-4-pyridinecarboxylic acid;
3-[4-[[1-pentyl-3-(1-oxo-2-phenylethyl)-1H-1,2,4-triazol-5-yl]methyl]phenyl]-4-pyridinecarboxylic acid;
3-[4-[[1-pentyl-3-(1,1-dimethoxypropyl)-1H-1,2,4-triazol-5-yl]methyl]phenyl]-4-pyridinecarboxylic acid;
3-[4-[[1-pentyl-3-(1,1-dimethoxybutyl)-1H-1,2,4-triazol-5-yl]methyl]phenyl]-4-pyridinecarboxylic acid;
3-[4-[[1-pentyl-3-(1,1-dimethoxypentyl)-1H-1,2,4-triazol-5-yl]methyl]phenyl]-4-pyridinecarboxylic acid;
3-[4-[[1-pentyl-3-(1-oxopropyl)-1H-1,2,4-triazol-5-yl]methyl]phenyl]-4-pyridinecarboxylic acid;
3-[4-[[1-pentyl-3-(1-oxobutyl)-1H-1,2,4-triazol-5-yl]methyl]phenyl]-4-pyridinecarboxylic acid;
3-[4-[[1-pentyl-3-(1-oxopentyl)-1H-1,2,4-triazol-5-yl]methyl]phenyl]-4-pyridinecarboxylic acid;
3-[4-[[1-pentyl-3-(1,1-difluorobutyl)-1H-1,2,4-triazol-5-yl]methyl]phenyl]-4-pyridinecarboxylic acid;
5-[3-[4-[(1-propyl-3-methyl-1H-1,2,4-triazol-5-yl)methyl]phenyl]-4-pyridinyl]-1H-tetrazole;
5-[3-[4-[(1-propyl-3-ethyl-1H-1,2,4-triazol-5-yl)methyl]phenyl]-4-pyridinyl]-1H-tetrazole;
5-[3-[4-[(1,3-dipropyl-1H-1,2,4-triazol-5-yl)methyl]phenyl]-4-pyridinyl]-1H-tetrazole;
5-[3-[4-[(1-propyl-3-isopropyl-1H-1,2,4-triazol-5-yl)methyl]phenyl]-4-pyridinyl]-1H-tetrazole;
5-[3-[4-[(1-propyl-3-butyl-1H-1,2,4-triazol-5-yl)methyl]phenyl]-4-pyridinyl]-1H-tetrazole;
5-[3-[4-[(1-propyl-3-secbutyl-1H-1,2,4-triazol-5-yl)methyl]phenyl]-4-pyridinyl]-1H-tetrazole;
5-[3-[4-[(1-propyl-3-isobutyl-1H-1,2,4-triazol-5-yl)methyl]phenyl]-4-pyridinyl]-1H-tetrazole;
5-[3-[4-[(1-propyl-3-tertbutyl-1H-1,2,4-triazol-5-yl)methyl]phenyl]-4-pyridinyl]-1H-tetrazole;
5-[3-[4-[(1-propyl-3-pentyl-1H-1,2,4-triazol-5-yl)methyl]phenyl]-4-pyridinyl]-1H-tetrazole;

5-[3-[4-[(1-propyl-3-isopentyl-1H-1,2,4-triazol-5-yl)methyl]phenyl]-4-pyridinyl]-1H-tetrazole;
5-[3-[4-[(1-propyl-3-cyclohexyl-1H-1,2,4-triazol-5-yl)methyl]phenyl]-4-pyridinyl]-1H-tetrazole;
5-[3-[4-[(1-propyl-3-cyclohexylmethyl-1H-1,2,4-triazol-5-yl)methyl]phenyl]-4-pyridinyl]-1H-tetrazole;
5-[3-[4-[[1-propyl-3-(2-cyclohexylethyl)-1H-1,2,4-triazol-5-yl]methyl]phenyl]-4-pyridinyl]-1H-tetrazole;
5-[3-[4-[(1-propyl-3-phenyl-1H-1,2,4-triazol-5-yl)methyl]phenyl]-4-pyridinyl]-1H-tetrazole;
5-[3-[4-[(1-propyl-3-phenylmethyl-1H-1,2,4-triazol-5-yl)methyl]phenyl]-4-pyridinyl]-1H-tetrazole;
5-[3-[4-[[1-propyl-3-(2-phenylethyl)-1H-1,2,4-triazol-5-yl]methyl]phenyl]-4-pyridinyl]-1H-tetrazole;
5-[3-[4-[(1-propyl-3-cyclohexanoyl-1H-1,2,4-triazol-5-yl)methyl]phenyl]-4-pyridinyl]-1H-tetrazole;
5-[3-[4-[[1-propyl-3-(1-oxo-2-cyclohexylethyl)-1H-1,2,4-triazol-5-yl]methyl]phenyl]-4-pyridinyl]-1H-tetrazole;
5-[3-[4-[(1-propyl-3-benzoyl-1H-1,2,4-triazol-5-yl)methyl]phenyl]-4-pyridinyl]-1H-tetrazole;
5-[3-[4-[[1-propyl-3-(1-oxo-2-phenylethyl)-1H-1,2,4-triazol-5-yl]methyl]phenyl]-4-pyridinyl]-1H-tetrazole;
5-[3-[4-[[1-propyl-3-(1,1-dimethoxypropyl)-1H-1,2,4-triazol-5-yl]methyl]phenyl]-4-pyridinyl]-1H-tetrazole;
5-[3-[4-[[1-propyl-3-(1,1-dimethoxybutyl)-1H-1,2,4-triazol-5-yl]methyl]phenyl]-4-pyridinyl]-1H-tetrazole;
5-[3-[4-[[1-propyl-3-(1,1-dimethoxypentyl)-1H-1,2,4-triazol-5-yl]methyl]phenyl]-4-pyridinyl]-1H-tetrazole;
5-[3-[4-[[1-propyl-3-(1-oxopropyl)-1H-1,2,4-triazol-5-yl]methyl]phenyl]-4-pyridinyl]-1H-tetrazole;
5-[3-[4-[[1-propyl-3-(1-oxobutyl)-1H-1,2,4-triazol-5-yl]methyl]phenyl]-4-pyridinyl]-1H-tetrazole;
5-[3-[4-[[1-propyl-3-(1-oxopentyl)-1H-1,2,4-triazol-5-yl]methyl]phenyl]-4-pyridinyl]-1H-tetrazole;
5-[3-[4-[[1-propyl-3-(1,1-difluorobutyl)-1H-1,2,4-triazol-5-yl]methyl]phenyl]-4-pyridinyl]-1H-tetrazole;
5-[3-[4-[(1-butyl-3-methyl-1H-1,2,4-triazol-5-yl)methyl]phenyl]-4-pyridinyl]-1H-tetrazole;
5-[3-[4-[(1-butyl-3-ethyl-1H-1,2,4-triazol-5-yl)methyl]phenyl]-4-pyridinyl]-1H-tetrazole;
5-[3-[4-[(1-butyl-3-propyl-1H-1,2,4-triazol-5-yl)methyl]phenyl]-4-pyridinyl]-1H-tetrazole;
5-[3-[4-[(1-butyl-3-isopropyl-1H-1,2,4-triazol-5-yl)methyl]phenyl]-4-pyridinyl]-1H-tetrazole;
5-[3-[4-[(1,3-dibutyl-1H-1,2,4-triazol-5-yl)methyl]phenyl]-4-pyridinyl]-1H-tetrazole;
5-[3-[4-[(1-butyl-3-secbutyl-1H-1,2,4-triazol-5-yl)methyl]phenyl]-4-pyridinyl]-1H-tetrazole;
5-[3-[4-[(1-butyl-3-isobutyl-1H-1,2,4-triazol-5-yl)methyl]phenyl]-4-pyridinyl]-1H-tetrazole;
5-[3-[4-[(1-butyl-3-tertbutyl-1H-1,2,4-triazol-5-yl)methyl]phenyl]-4-pyridinyl]-1H-tetrazole;
5-[3-[4-[(1-butyl-3-pentyl-1H-1,2,4-triazol-5-yl)methyl]phenyl]-4-pyridinyl]-1H-tetrazole;
5-[3-[4-[(1-butyl-3-isopentyl-1H-1,2,4-triazol-5-yl)methyl]phenyl]-4-pyridinyl]-1H-tetrazole;
5-[3-[4-[(1-butyl-3-cyclohexyl-1H-1,2,4-triazol-5-yl)methyl]phenyl]-4-pyridinyl]-1H-tetrazole;
5-[3-[4-[(1-butyl-3-cyclohexylmethyl-1H-1,2,4-triazol-5-yl)methyl]phenyl]-4-pyridinyl]-1H-tetrazole;
5-[3-[4-[[1-butyl-3-(2-cyclohexylethyl)-1H-1,2,4-triazol-5-yl]methyl]phenyl]-4-pyridinyl]-1H-tetrazole;
5-[3-[4-[(1-butyl-3-phenyl-1H-1,2,4-triazol-5-yl)methyl]phenyl]-4-pyridinyl]-1H-tetrazole;
5-[3-[4-[(1-butyl-3-phenylmethyl-1H-1,2,4-triazol-5-yl)methyl]phenyl]-4-pyridinyl]-1H-tetrazole;
5-[3-[4-[[1-butyl-3-(2-phenylethyl)-1H-1,2,4-triazol-5-yl]methyl]phenyl]-4-pyridinyl]-1H-tetrazole;
5-[3-[4-[(1-butyl-3-cyclohexanoyl-1H-1,2,4-triazol-5-yl)methyl]phenyl]-4-pyridinyl]-1H-tetrazole;
5-[3-[4-[[1-butyl-3-(1-oxo-2-cyclohexylethyl)-1H-1,2,4-triazol-5-yl]methyl]phenyl]-4-pyridinyl]-1H-tetrazole;
5-[3-[4-[(1-butyl-3-benzoyl-1H-1,2,4-triazol-5-yl)methyl]phenyl]-4-pyridinyl]-1H-tetrazole;
5-[3-[4-[[1-butyl-3-(1-oxo-2-phenylethyl)-1H-1,2,4-triazol-5-yl]methyl]phenyl]-4-pyridinyl]-1H-tetrazole;
5-[3-[4-[[1-butyl-3-(1,1-dimethoxypropyl)-1H-1,2,4-triazol-5-yl]methyl]phenyl]-4-pyridinyl]-1H-tetrazole;
5-[3-[4-[[1-butyl-3-(1,1-dimethoxybutyl)-1H-1,2,4-triazol-5-yl]methyl]phenyl]-4-pyridinyl]-1H-tetrazole;
5-[3-[4-[[1-butyl-3-(1,1-dimethoxypentyl)-1H-1,2,4-triazol-5-yl]methyl]phenyl]-4-pyridinyl]-1H-tetrazole;
5-[3-[4-[[1-butyl-3-(1-oxopropyl)-1H-1,2,4-triazol-5-yl]methyl]phenyl]-4-pyridinyl]-1H-tetrazole;
5-[3-[4-[[1-butyl-3-(1-oxobutyl)-1H-1,2,4-triazol-5-yl]methyl]phenyl]-4-pyridinyl]-1H-tetrazole;
5-[3-[4-[[1-butyl-3-(1-oxopentyl)-1H-1,2,4-triazol-5-yl]methyl]phenyl]-4-pyridinyl]-1H-tetrazole;
5-[3-[4-[[1-butyl-3-(1,1-difluorobutyl)-1H-1,2,4-triazol-5-yl]methyl]phenyl]-4-pyridinyl]-1H-tetrazole;
5-[3-[4-[(1-pentyl-3-methyl-1H-1,2,4-triazol-5-yl)methyl]phenyl]-4-pyridinyl]-1H-tetrazole;
5-[3-[4-[(1-pentyl-3-ethyl-1H-1,2,4-triazol-5-yl)methyl]phenyl]-4-pyridinyl]-1H-tetrazole;
5-[3-[4-[(1-pentyl-3-propyl-1H-1,2,4-triazol-5-yl)methyl]phenyl]-4-pyridinyl]-1H-tetrazole;
5-[3-[4-[(1-pentyl-3-isopropyl-1H-1,2,4-triazol-5-yl)methyl]phenyl]-4-pyridinyl]-1H-tetrazole;
5-[3-[4-[(1-pentyl-3-butyl-1H-1,2,4-triazol-5-yl)methyl]phenyl]-4-pyridinyl]-1H-tetrazole;
5-[3-[4-[(1-pentyl-3-secbutyl-1H-1,2,4-triazol-5-yl)methyl]phenyl]-4-pyridinyl]-1H-tetrazole;
5-[3-[4-[(1-pentyl-3-isobutyl-1H-1,2,4-triazol-5-yl)methyl]phenyl]-4-pyridinyl]-1H-tetrazole;
5-[3-[4-[(1-pentyl-3-tertbutyl-1H-1,2,4-triazol-5-yl)methyl]phenyl]-4-pyridinyl]-1H-tetrazole;
5-[3-[4-[(1,3-dipentyl-1H-1,2,4-triazol-5-yl)methyl]phenyl]-4-pyridinyl]-1H-tetrazole;
5-[3-[4-[(1-pentyl-3-isopentyl-1H-1,2,4-triazol-5-yl)methyl]phenyl]-4-pyridinyl]-1H-tetrazole;
5-[3-[4-[(1-pentyl-3-cyclohexyl-1H-1,2,4-triazol-5-yl)methyl]phenyl]-4-pyridinyl]-1H-tetrazole;
5-[3-[4-[(1-pentyl-3-cyclohexylmethyl-1H-1,2,4-triazol-5-yl)methyl]phenyl]-4-pyridinyl]-1H-tetrazole;
5-[3-[4-[[1-pentyl-3-(2-cyclohexylethyl)-1H-1,2,4-triazol-5-yl]methyl]phenyl]-4-pyridinyl]-1H-tetrazole;
5-[3-[4-[(1-pentyl-3-phenyl-1H-1,2,4-triazol-5-yl)methyl]phenyl]-4-pyridinyl]-1H-tetrazole;
5-[3-[4-[(1-pentyl-3-phenylmethyl-1H-1,2,4-triazol-5-yl)methyl]phenyl]-4-pyridinyl]-1H-tetrazole;
5-[3-[4-[[1-pentyl-3-(2-phenylethyl)-1H-1,2,4-triazol-5-yl]methyl]phenyl]-4-pyridinyl]-1H-tetrazole;
5-[3-[4-[(1-pentyl-3-cyclohexanoyl-1H-1,2,4-triazol-5-yl)methyl]phenyl]-4-pyridinyl]-1H-tetrazole;

5-[3-[4-[[1-pentyl-3-(1-oxo-2-cyclohexylethyl)-1H-1,2,4-triazol-5-yl]methyl]phenyl]-4-pyridinyl]-1H-tetrazole;

5-[3-[4-[(1-pentyl-3-benzoyl-1H-1,2,4-triazol-5-yl)methyl]phenyl]-4-pyridinyl]-1H-tetrazole;

5-[3-[4-[[1-pentyl-3-(1-oxo-2-phenylethyl)-1H-1,2,4-triazol-5-yl]methyl]phenyl]-4-pyridinyl]-1H-tetrazole;

5-[3-[4-[[1-pentyl-3-(1,1-dimethoxypropyl)-1H-1,2,4-triazol-5-yl]methyl]phenyl]-4-pyridinyl]-1H-tetrazole;

5-[3-[4-[[1-pentyl-3-(1,1-dimethoxybutyl)-1H-1,2,4-triazol-5-yl]methyl]phenyl]-4-pyridinyl]-1H-tetrazole;

5-[3-[4-[[1-pentyl-3-(1,1-dimethoxypentyl)-1H-1,2,4-triazol-5-yl]methyl]phenyl]-4-pyridinyl]-1H-tetrazole;

5-[3-[4-[[1-pentyl-3-(1-oxopropyl)-1H-1,2,4-triazol-5-yl]methyl]phenyl]-4-pyridinyl]-1H-tetrazole;

5-[3-[4-[[1-pentyl-3-(1-oxobutyl)-1H-1,2,4-triazol-5-yl]methyl]phenyl]-4-pyridinyl]-1H-tetrazole;

5-[3-[4-[[1-pentyl-3-(1-oxopentyl)-1H-1,2,4-triazol-5-yl]methyl]phenyl]-4-pyridinyl]-1H-tetrazole; and 5-[3-[4-[[t-pentyl-3-(1,1-difluorobutyl)-1H-1,2,4-triazol-5-yl]methyl]phenyl]-4-pyridinyl]-1H-tetrazole.

A family of specific compounds of more particular interest within Formula V consists of the following compounds:

5-[3-[4-[(1-butyl-3-methyl-1H-1,2,4-triazol-5-yl)methyl]phenyl]-4-pyridinyl]-1H-tetrazole;

5-[3-[4-[(1-butyl-3-ethyl-1H-1,2,4-triazol-5-yl)methyl]phenyl]-4-pyridinyl]-1H-tetrazole;

5-[3-[4-[(1-butyl-3-propyl-1H-1,2,4-triazol-5-yl)methyl]phenyl]-4-pyridinyl]-1H-tetrazole;

5-[3-[4-[(1-butyl-3-isopropyl-1H-1,2,4-triazol-5-yl)methyl]phenyl]-4-pyridinyl]-1H-tetrazole;

5-[3-[4-[(1,3-dibutyl-1H-1,2,4-triazol-5-yl)methyl]phenyl]-4-pyridinyl]-1H-tetrazole;

5-[3-[4-[(1-butyl-3-secbutyl-1H-1,2,4-triazol-5-yl)methyl]phenyl]-4-pyridinyl]-1H-tetrazole;

5-[3-[4-[(1-butyl-3-isobutyl-1H-1,2,4-triazol-5-yl)methyl]phenyl]-4-pyridinyl]-1H-tetrazole;

5-[3-[4-[(1-butyl-3-tertbutyl-1H-1,2,4-triazol-5-yl)methyl]phenyl]-4-pyridinyl]-1H-tetrazole;

5-[3-[4-[(1-butyl-3-pentyl-1H-1,2,4-triazol-5-yl)methyl]phenyl]-4-pyridinyl]-1H-tetrazole;

5-[3-[4-[(1-butyl-3-isopentyl-1H-1,2,4-triazol-5-yl)methyl]phenyl]-4-pyridinyl]-1H-tetrazole;

5-[3-[4-[(1-butyl-3-cyclohexyl-1H-1,2,4-triazol-5-yl)methyl]phenyl]-4-pyridinyl]-1H-tetrazole;

5-[3-[4-[(1-butyl-3-cyclohexylmethyl-1H-1,2,4-triazol-5-yl)methyl]phenyl]-4-pyridinyl]-1H-tetrazole;

5-[3-[4-[[1-butyl-3-(2-cyclohexylethyl)-1H-1,2,4-triazol-5-yl]methyl]phenyl]-4-pyridinyl]-1H-tetrazole;

5-[3-[4-[(1-butyl-3-phenyl-1H-1,2,4-triazol-5-yl)methyl]phenyl]-4-pyridinyl]-1H-tetrazole;

5-[3-[4-[(1-butyl-3-phenylmethyl-1H-1,2,4-triazol-5-yl)methyl]phenyl]-4-pyridinyl]-1H-tetrazole; and 5-[3-[4-[[1-butyl-3-(2-phenylethyl)-1H-1,2,4-triazol-5-yl]methyl]phenyl]-4-pyridinyl]-1H-tetrazole.

Another subclass of compounds of Formula I which is of even more particular interest consists of those compounds of Formula VI

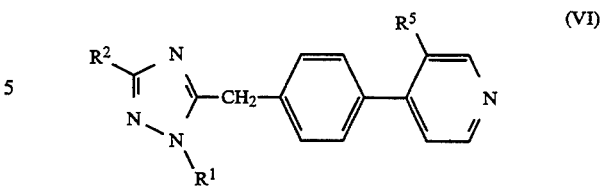

wherein m is one; wherein $R^1$ is selected from methyl, ethyl, n-propyl, isopropyl, n-butyl, sec-butyl, isobutyl, tert-butyl, 4-methylbutyl, n-pentyl, neopentyl, phenyl, benzyl, phenethyl, cyclohexyl, cyclohexylmethyl, 2-butenyl, 3-butenyl, 2-butynyl, 3-butynyl and 2-hydroxybutyl; wherein $R^2$ is selected from ethyl, n-propyl, isopropyl, n-butyl, sec-butyl, isobutyl, 4-methylbutyl, n-pentyl, 1-oxo-2-phenylethyl, 1-oxo-2-cyclohexylethyl, 1,1-difluoro-2-phenylethyl, 1,1-difluoro-2-cyclohexylethyl, 2-cyclohexylethyl, 1,1-difluoro-3-cyclohexylpropyl, 1,1-dimethoxybutyl, 1,1-difluoroethyl, 1,1-difluoropropyl, 1,1-difluorobutyl, 1,1-difluoropentyl, benzyl, 2-phenylethyl, 1,1-difluoro-3-phenylpropyl, cyclohexylmethyl, cyclohexanoyl, 1-butenyl, 2-butenyl, 3-butenyl, 1-butynyl, 2-butynyl, 3-butynyl, propylthio and butylthio; wherein $R^5$ is an acidic group selected from $CO_2H$ and

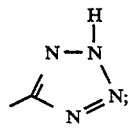

or a tautomer thereof or a pharmaceutically-acceptable salt thereof.

A family of specific compounds of particular interest within Formula VI consists of the following compounds:

4-[4-[(1-propyl-3-ethyl-1H-1,2,4-triazol-5-yl)methyl]phenyl]-3-pyridinecarboxylic acid;

4-[4-[(1,3-dipropyl-1H-1,2,4-triazol-5-yl)methyl]phenyl]-3-pyridinecarboxylic acid;

4-[4-[(1-propyl-3-isopropyl-1H-1,2,4-triazol-5-yl)methyl]phenyl]-3-pyridinecarboxylic acid;

4-[4-[(1-propyl-3-butyl-1H-1,2,4-triazol-5-yl)methyl]phenyl]-3-pyridinecarboxylic acid;

4-[4-[(1-propyl-3-secbutyl-1H-1,2,4-triazol-5-yl)methyl]phenyl]-3-pyridinecarboxylic acid;

4-[4-[(1-propyl-3-isobutyl-1H-1,2,4-triazol-5-yl)methyl]phenyl]-3-pyridinecarboxylic acid;

4-[4-[(1-propyl-3-tertbutyl-1H-1,2,4-triazol-5-yl)methyl]phenyl]-3-pyridinecarboxylic acid;

4-[4-[(1-propyl-3-pentyl-1H-1,2,4-triazol-5-yl)methyl]phenyl]-3-pyridinecarboxylic acid;

4-[4-[(1-propyl-3-isopentyl-1H-1,2,4-triazol-5-yl)methyl]phenyl]-3-pyridinecarboxylic acid;

4-[4-[(1-propyl-3-cyclohexyl-1H-1,2,4-triazol-5-yl)methyl]phenyl]-3-pyridinecarboxylic acid;

4-[4-[(1-propyl-3-cyclohexylmethyl-1H-1,2,4-triazol-5-yl)methyl]phenyl]-3-pyridinecarboxylic acid;

4-[4-[[1-propyl-3-(2-cyclohexylethyl)-1H-1,2,4-triazol-5-yl]methyl]phenyl]-3-pyridinecarboxylic acid;

4-[4-[(1-propyl-3-phenyl-1H-1,2,4-triazol-5-yl)methyl]phenyl]-3-pyridinecarboxylic acid;

4-[4-[(1-propyl-3-phenylmethyl-1H-1,2,4-triazol-5-yl)methyl]phenyl]-3-pyridinecarboxylic acid;

4-[4-[[1-propyl-3-(2-phenylethyl)-1H-1,2,4-triazol-5-yl]methyl]phenyl]-3-pyridinecarboxylic acid;

4-[4-[(1-propyl-3-cyclohexanoyl-1H-1,2,4-triazol-5-yl)methyl]phenyl]-3-pyridinecarboxylic acid;

4-[4-[[1-propyl-3-(1-oxo-2-cyclohexylethyl)-1H-1,2,4-triazol-5-yl]methylphenyl]-3-pyridinecarboxylic acid;

4-[4-[(1-propyl-3-benzoyl-1H-1,2,4-triazol-5-yl)methyl]phenyl]-3-pyridinecarboxylic acid;

4-[4-[[1-propyl-3-(1-oxo-2-phenylethyl)-1H-1,2,4-triazol-5-yl]methylphenyl]-3-pyridinecarboxylic acid;

4-[4-[[1-propyl-3-(1,1-dimethoxypropyl)-1H-1,2,4-triazol-5-yl]methyl]phenyl]-3-pyridinecarboxylic acid;

4-[4-[[1-propyl-3-(1,1-dimethoxybutyl)-1H-1,2,4-triazol-5-yl]methyl]phenyl]-3-pyridinecarboxylic acid;

4-[4-[[1-propyl-3-(1,1-dimethoxypentyl)-1H-1,2,4-triazol-5-yl]methyl]phenyl]-3-pyridinecarboxylic acid;

4-[4-[[1-propyl-3-(1-oxopropyl)-1H-1,2,4-triazol-5-yl]methyl]phenyl]-3-pyridinecarboxylic acid;

4-[4-[[1-propyl-3-(1-oxobutyl)-1H-1,2,4-triazol-5-yl]methyl]phenyl]-3-pyridinecarboxylic acid;

4-[4-[[1-propyl-3-(1-oxopentyl)-1H-1,2,4-triazol-5-yl]methyl]phenyl]-3-pyridinecarboxylic acid;

4-[4-[[1-propyl-3-(1,1-difluorobutyl)-1H-1,2,4-triazol-5-yl]methyl]phenyl]-3-pyridinecarboxylic acid;

4-[4-[(1-butyl-3-methyl-1H-1,2,4-triazol-5-yl)methyl]phenyl]-3-pyridinecarboxylic acid;

4-[4-[(1-butyl-3-ethyl-1H-1,2,4-triazol-5-yl)methyl]phenyl]-3-pyridinecarboxylic acid;

4-[4-[(1-butyl-3-propyl-1H-1,2,4-triazol-5-yl)methyl]phenyl]-3-pyridinecarboxylic acid;

4-[4-[(1-butyl-3-isopropyl-1H-1,2,4-triazol-5-yl)methyl]phenyl]-3-pyridinecarboxylic acid;

4-[4-[(1,3-dibutyl-1H-1,2,4-triazol-5-yl)methyl]phenyl]-3-pyridinecarboxylic acid;

4-[4-[(1-butyl-3-secbutyl-1H-1,2,4-triazol-5-yl)methyl]phenyl]-3-pyridinecarboxylic acid 4-[4-[(1-butyl-3-isobutyl-1H-1,2,4-triazol-5-yl)methyl]phenyl]-3-pyridinecarboxylic acid;

4-[4-[(1-butyl-3-tertbutyl-1H-1,2,4-triazol-5-yl)methyl]phenyl]-3-pyridinecarboxylic acid;

4-[4-[(1-butyl-3-pentyl-1H-1,2,4-triazol-5-yl)methyl]phenyl]-3-pyridinecarboxylic acid;

4-[4-[(1-butyl-3-isopentyl-1H-1,2,4-triazol-5-yl)methyl]phenyl]-3-pyridinecarboxylic acid;

4-[4-[(1-butyl-3-cyclohexyl-1H-1,2,4-triazol-5-yl)methyl]phenyl]-3-pyridinecarboxylic acid;

4-[4-[(1-butyl-3-cyclohexylmethyl-1H-1,2,4-triazol-5-yl)methyl]phenyl]-3-pyridinecarboxylic acid;

4-[4-[[1-butyl-3-(2-cyclohexylethyl)-1H-1,2,4-triazol-5-yl]methyl]phenyl]-3-pyridinecarboxylic acid;

4-[4-[(1-butyl-3-phenyl-1H-1,2,4-triazol-5-yl)methyl]phenyl]-3-pyridinecarboxylic acid;

4-[4-[(1-butyl-3-phenylmethyl-1H-1,2,4-triazol-5-yl)methyl]phenyl]-3-pyridinecarboxylic acid;

4-[4-[[1-butyl-3-(2-phenylethyl)-1H-1,2,4-triazol-5-yl]methyl]phenyl]-3-pyridinecarboxylic acid;

4-[4-[(1-butyl-3-cyclohexanoyl-1H-1,2,4-triazol-5-yl)methyl]phenyl]-3-pyridinecarboxylic acid;

4-[4-[[1-butyl-3-(1-oxo-2-cyclohexylethyl)-1H-1,2,4-triazol-5-yl]methyl]phenyl]-3-pyridinecarboxylic acid;

4-[4-[(1-butyl-3-benzoyl-1H-1,2,4-triazol-5-yl)methyl]phenyl]-3-pyridinecarboxylic acid;

4-[4-[[1-butyl-3-(1-oxo-2-phenylethyl)-1H-1,2,4-triazol-5-yl]methyl]phenyl]-3-pyridinecarboxylic acid;

4-[4-[[1-butyl-3-(1,1-dimethoxypropyl)-1H-1,2,4-triazol-5-yl]methyl]phenyl]-3-pyridinecarboxylic acid;

4-[4-[[1-butyl-3-(1,1-dimethoxybutyl)-1H-1,2,4-triazol-5-yl]methyl]phenyl]-3-pyridinecarboxylic acid;

4-[4-[[1-butyl-3-(1,1-dimethoxypentyl)-1H-1,2,4-triazol-5-yl]methyl]phenyl]-3-pyridinecarboxylic acid;

4-[4-[[1-butyl-3-(1-oxopropyl)-1H-1,2,4-triazol-5-yl]methyl]phenyl]-3-pyridinecarboxylic acid;

4-[4-[[1-butyl-3-(1-oxobutyl)-1H-1,2,4-triazol-5-yl]methyl]phenyl]-3-pyridinecarboxylic acid;

4-[4-[[1-butyl-3-(1-oxopentyl)-1H-1,2,4-triazol-5-yl]methyl]phenyl]-3-pyridinecarboxylic acid;

4-[4-[[1-butyl-3-(1,1-difluorobutyl)-1H-1,2,4-triazol-5-yl]methyl]phenyl]-3-pyridinecarboxylic acid;

4-[4-[(1-pentyl-3-methyl-1H-1,2,4-triazol-5-yl)methyl]phenyl]-3-pyridinecarboxylic acid;

4-[4-[(1-pentyl-3-ethyl-1H-1,2,4-triazol-5-yl)methyl]phenyl]-3-pyridinecarboxylic acid;

4-[4-[(1-pentyl-3-propyl-1H-1,2,4-triazol-5-yl)methyl]phenyl]-3-pyridinecarboxylic acid;

4-[4-[(1-pentyl-3-isopropyl-1H-1,2,4-triazol-5-yl)methyl]phenyl]-3-pyridinecarboxylic acid;

4-[4-[(1-pentyl-3-butyl-1H-1,2,4-triazol-5-yl)methyl]phenyl]-3-pyridinecarboxylic acid;

4-[4-[(1-pentyl-3-secbutyl-1H-1,2,4-triazol-5-yl)methyl]phenyl]-3-pyridinecarboxylic acid;

4-[4-[(1-pentyl-3-isobutyl-1H-1,2,4-triazol-5-yl)methyl]phenyl]-3-pyridinecarboxylic acid;

4-[4-[(1-pentyl-3-tertbutyl-1H-1,2,4-triazol-5-yl)methyl]phenyl]-3-pyridinecarboxylic acid;

4-[4-[(1,3-dipentyl-1H-1,2,4-triazol-5-yl)methyl]phenyl]-3-pyridinecarboxylic acid;

4-[4-[(1-pentyl-3-isopentyl-1H-1,2,4-triazol-5-yl)methyl]phenyl]-3-pyridinecarboxylic acid;

4-[4-[(1-pentyl-3-cyclohexyl-1H-1,2,4-triazol-5-yl)methyl]phenyl]-3-pyridinecarboxylic acid;

4-[4-[(1-pentyl-3-cyclohexylmethyl-1H-1,2,4-triazol-5-yl)methyl]phenyl]-3-pyridinecarboxylic acid;

4-[4-[[1-pentyl-3-(2-cyclohexylethyl)-1H-1,2,4-triazol-5-yl]methyl]phenyl]-3-pyridinecarboxylic acid;

4-[4-[(1-pentyl-3-phenyl-1H-1,2,4-triazol-5-yl)methyl]phenyl]-3-pyridinecarboxylic acid;

4-[4-[(1-pentyl-3-phenylmethyl-1H-1,2,4-triazol-5-yl)methyl]phenyl]-3-pyridinecarboxylic acid;

4-[4-[[1-pentyl-3-(2-phenylethyl)-1H-1,2,4-triazol-5-yl]methyl]phenyl]-3-pyridinecarboxylic acid;

4-[4-[(1-pentyl-3-cyclohexanoyl-1H-1,2,4-triazol-5-yl)methyl]phenyl]-3-pyridinecarboxylic acid;

4-[4-[[1-pentyl-3-(1-oxo-2-cyclohexylethyl)-1H-1,2,4-triazol-5-yl]methyl]phenyl]-3-pyridinecarboxylic acid;

4-[4-[(1-pentyl-3-benzoyl-1H-1,2,4-triazol-5-yl)methyl]phenyl]-3-pyridinecarboxylic acid;

4-[4-[[1-pentyl-3-(1-oxo-2-phenylethyl)-1H-1,2,4-triazol-5-yl]methyl]phenyl]-3-pyridinecarboxylic acid;

4-[4-[[1-pentyl-3-(1,1-dimethoxypropyl)-1H-1,2,4-triazol-5-yl]methyl]phenyl]-3-pyridinecarboxylic acid;

4-[4-[[1-pentyl-3-(1,1-dimethoxybutyl)-1H-1,2,4-triazol-5-yl]methyl]phenyl]-3-pyridinecarboxylic acid;

4-[4-[[1-pentyl-3-(1,1-dimethoxypentyl)-1H-1,2,4-triazol-5-yl]methyl]phenyl]-3-pyridinecarboxylic acid;

4-[4-[[1-pentyl-3-(1-oxopropyl)-1H-1,2,4-triazol-5-yl]methyl]phenyl]-3-pyridinecarboxylic acid;

4-[4-[[1-pentyl-3-(1-oxobutyl)-1H-1,2,4-triazol-5-yl]methyl]phenyl]-3-pyridinecarboxylic acid;
4-[4-[[1-pentyl-3-(1-oxopentyl)-1H-1,2,4-triazol-5-yl]methyl]phenyl]-3-pyridinecarboxylic acid;
4-[4-[[1-pentyl-3-(1,1-difluorobutyl)-1H-1,2,4-triazol-5-yl]methyl]phenyl]-3-pyridinecarboxylic acid;
5-[4-[4-[(1-butyl-3-methyl-1H-1,2,4-triazol-5-yl)methyl]phenyl]-3-pyridinyl]-1H-tetrazole;
5-[4-[4-[(1-butyl-3-ethyl-1H-1,2,4-triazol-5-yl)methyl]phenyl]-3-pyridinyl]-1H-tetrazole;
5-[4-[4-[(1-butyl-3-propyl-1H-1,2,4-triazol-5-yl)methyl]phenyl]-3-pyridinyl]-1H-tetrazole;
5-[4-[4-[(1-butyl-3-isopropyl-1H-1,2,4-triazol-5-yl)methyl]phenyl]-3-pyridinyl]-1H-tetrazole;
5-[4-[4-[(1,3-dibutyl-1H-1,2,4-triazol-5-yl)methyl]phenyl]-3-pyridinyl]-1H-tetrazole;
5-[4-[4-[(1-butyl-3-secbutyl-1H-1,2,4-triazol-5-yl)methyl]phenyl]-3-pyridinyl]-1H-tetrazole;
5-[4-[4-[(1-butyl-3-isobutyl-1H-1,2,4-triazol-5-yl)methyl]phenyl]-3-pyridinyl]-1H-tetrazole;
5-[4-[4-[(1-butyl-3-tertbutyl-1H-1,2,4-triazol-5-yl)methyl]phenyl]-3-pyridinyl]-1H-tetrazole;
5-[4-[4-[(1-butyl-3-pentyl-1H-1,2,4-triazol-5-yl)methyl]phenyl]-3-pyridinyl]-1H-tetrazole;
5-[4-[4-[(1-butyl-3-isopentyl-1H-1,2,4-triazol-5-yl)methyl]phenyl]-3-pyridinyl]-1H-tetrazole;
5-[4-[4-[(1-butyl-3-cyclohexyl-1H-1,2,4-triazol-5-yl)methyl]phenyl]-3-pyridinyl]-1H-tetrazole;
5-[4-[4-[(1-butyl-3-cyclohexylmethyl-1H-1,2,4-triazol-5-yl)methyl]phenyl]-3-pyridinyl]-1H-tetrazole;
5-[4-[4-[[1-butyl-3-(2-cyclohexylethyl)-1H-1,2,4-triazol-5-yl]methyl]phenyl]-3-pyridinyl]-1H-tetrazole;
5-[4-[4-[(1-butyl-3-phenyl-1H-1,2,4-triazol-5-yl)methyl]phenyl]-3-pyridinyl]-1H-tetrazole;
5-[4-[4-[(1-butyl-3-phenylmethyl-1H-1,2,4-triazol-5-yl)methyl]phenyl]-3-pyridinyl]-1H-tetrazole;
5-[4-[4-[[1-butyl-3-(2-phenylethyl)-1H-1,2,4-triazol-5-yl]methyl]phenyl]-3-pyridinyl]-1H-tetrazole;
5-[4-[4-[(1-propyl-3-methyl-1H-1,2,4-triazol-5-yl)methyl]phenyl]-3-pyridinyl]-1H-tetrazole;
5-[4-[4-[(1-propyl-3-ethyl-1H-1,2,4-triazol-5-yl)methyl]phenyl]-3-pyridinyl]-1H-tetrazole;
5-[4-[4-[(1,3-dipropyl-1H-1,2,4-triazol-5-yl)methyl]phenyl]-3-pyridinyl]-1H-tetrazole;
5-[4-[4-[(1-propyl-3-isopropyl-1H-1,2,4-triazol-5-yl)methyl]phenyl]-3-pyridinyl]-1H-tetrazole;
5-[4-[4-[(1-propyl-3-butyl-1H-1,2,4-triazol-5-yl)methyl]phenyl]-3-pyridinyl]-1H-tetrazole;
5-[4-[4-[(1-propyl-3-secbutyl-1H-1,2,4-triazol-5-yl)methyl]phenyl]-3-pyridinyl]-1H-tetrazole;
5-[4-[4-[(1-propyl-3-isobutyl-1H-1,2,4-triazol-5-yl)methyl]phenyl]-3-pyridinyl]-1H-tetrazole;
5-[4-[4-[(1-propyl-3-tertbutyl-1H-1,2,4-triazol-5-yl)methyl]phenyl]-3-pyridinyl]-1H-tetrazole;
5-[4-[4-[(1-propyl-3-pentyl-1H-1,2,4-triazol-5-yl)methyl]phenyl]-3-pyridinyl]-1H-tetrazole;
5-[4-[4-[(1-propyl-3-isopentyl-1H-1,2,4-triazol-5-yl)methyl]phenyl]-3-pyridinyl]-1H-tetrazole;
5-[4-[4-[(1-propyl-3-cyclohexyl-1H-1,2,4-triazol-5-yl)methyl]phenyl]-3-pyridinyl]-1H-tetrazole;
5-[4-[4-[(1-propyl-3-cyclohexylmethyl-1H-1,2,4-triazol-5-yl)methyl]phenyl]-3-pyridinyl]-1H-tetrazole;
5-[4-[4-[[1-propyl-3-(2-cyclohexylethyl)-1H-1,2,4-triazol-5-yl]methyl]phenyl]-3-pyridinyl]-1H-tetrazole;
5-[4-[4-[(1-propyl-3-phenyl-1H-1,2,4-triazol-5-yl)methyl]phenyl]-3-pyridinyl]-1H-tetrazole;
5-[4-[4-[(1-propyl-3-phenylmethyl-1H-1,2,4-triazol-5-yl)methyl]phenyl]-3-pyridinyl]-1H-tetrazole;
5-[4-[4-[[1-propyl-3-(2-phenylethyl)-1H-1,2,4-triazol-5-yl]methyl]phenyl]-3-pyridinyl]-1H-tetrazole;
5-[4-[4-[(1-propyl-3-cyclohexanoyl-1H-1,2,4-triazol-5-yl)methyl]phenyl]-3-pyridinyl]-1H-tetrazole;
5-[4-[4-[[1-propyl-3-(1-oxo-2-cyclohexylethyl)-1H-1,2,4-triazol-5-yl]methyl]phenyl]-3-pyridinyl]-1H-tetrazole;
5-[4-[4-[(1-propyl-3-benzoyl-1H-1,2,4-triazol-5-yl)methyl]phenyl]-3-pyridinyl]-1H-tetrazole;
5-[4-[4-[[1-propyl-3-(1-oxo-2-phenylethyl)-1H-1,2,4-triazol-5-yl]methyl]phenyl]-3-pyridinyl]-1H-tetrazole;
5-[4-[4-[[1-propyl-3-(1,1-dimethoxypropyl)-1H-1,2,4-triazol-5-yl]methyl]phenyl]-3-pyridinyl]-1H-tetrazole;
5-[4-[4-[[1-propyl-3-(1,1-dimethoxybutyl)-1H-1,2,4-triazol-5-yl]methyl]phenyl]-3-pyridinyl]-1H-tetrazole;
5-[4-[4-[[1-propyl-3-(1,1-dimethoxypentyl)-1H-1,2,4-triazol-5-yl]methyl]phenyl]-3-pyridinyl]-1H-tetrazole;
5-[4-[4-[[1-propyl-3-(1-oxopropyl)-1H-1,2,4-triazol-5-yl]methyl]phenyl]-3-pyridinyl]-1H-tetrazole;
5-[4-[4-[[1-propyl-3-(1-oxobutyl)-1H-1,2,4-triazol-5-yl]methyl]phenyl]-3-pyridinyl]-1H-tetrazole;
5-[4-[4-[[1-propyl-3-(1-oxopentyl)-1H-1,2,4-triazol-5-yl]methyl]phenyl]-3-pyridinyl]-1H-tetrazole;
5-[4-[4-[[1-propyl-3-(1,1-difluorobutyl)-1H-1,2,4-triazol-5-yl]methyl]phenyl]-3-pyridinyl]-1H-tetrazole;
5-[4-[4-[(1-butyl-3-methyl-1H-1,2,4-triazol-5-yl)methyl]phenyl]-3-pyridinyl]-1H-tetrazole;
5-[4-[4-[(1-butyl-3-ethyl-1H-1,2,4-triazol-5-yl)methyl]phenyl]-3-pyridinyl]-1H-tetrazole;
5-[4-[4-[(1-butyl-3-propyl-1H-1,2,4-triazol-5-yl)methyl]phenyl]-3-pyridinyl]-1H-tetrazole;
5-[4-[4-[(1-butyl-3-isopropyl-1H-1,2,4-triazol-5-yl)methyl]phenyl]-3-pyridinyl]-1H-tetrazole;
5-[4-[4-[(1,3-dibutyl-1H-1,2,4-triazol-5-yl)methyl]phenyl]-3-pyridinyl]-1H-tetrazole;
5-[4-[4-[(1-butyl-3-secbutyl-1H-1,2,4-triazol-5-yl)methyl]phenyl]-3-pyridinyl]-1H-tetrazole;
5-[4-[4-[(1-butyl-3-isobutyl-1H-1,2,4-triazol-5-yl)methyl]phenyl]-3-pyridinyl]-1H-tetrazole;
5-[4-[4-[(1-butyl-3-tertbutyl-1H-1,2,4-triazol-5-yl)methyl]phenyl]-3-pyridinyl]-1H-tetrazole;
5-[4-[4-[(1-butyl-3-pentyl-1H-1,2,4-triazol-5-yl)methyl]phenyl]-3-pyridinyl]-1H-tetrazole;
5-[4-[4-[(1-butyl-3-isopentyl-1H-1,2,4-triazol-5-yl)methyl]phenyl]-3-pyridinyl]-1H-tetrazole;
5-[4-[4-[(1-butyl-3-cyclohexyl-1H-1,2,4-triazol-5-yl)methyl]phenyl]-3-pyridinyl]-1H-tetrazole;
5-[4-[4-[(1-butyl-3-cyclohexylmethyl-1H-1,2,4-triazol-5-yl)methyl]phenyl]-3-pyridinyl]-1H-tetrazole;
5-[4-[4-[[1-butyl-3-(2-cyclohexylethyl)-1H-1,2,4-triazol-5-yl]methyl]phenyl]-3-pyridinyl]-1H-tetrazole;
5-[4-[4-[(1-butyl-3-phenyl-1H-1,2,4-triazol-5-yl)methyl]phenyl]-3-pyridinyl]-1H-tetrazole;
5-[4-[4-[(1-butyl-3-phenylmethyl-1H-1,2,4-triazol-5-yl)methyl]phenyl]-3-pyridinyl]-1H-tetrazole;
5-[4-[4-[[1-butyl-3-(2-phenylethyl)-1H-1,2,4-triazol-5-yl]methyl]phenyl]-3-pyridinyl]-1H-tetrazole;
5-[4-[4-[(1-butyl-3-cyclohexanoyl-1H-1,2,4-triazol-5-yl)methyl]phenyl]-3-pyridinyl]-1H-tetrazole;
5-[4-[4-[[1-butyl-3-(1-oxo-2-cyclohexylethyl)-1H-1,2,4-triazol-5-yl]methyl]phenyl]-3-pyridinyl]-1H-tetrazole;

5-[4-[4-[(1-butyl-3-benzoyl-1H-1,2,4-triazol-5-yl)methyl]phenyl]-3-pyridinyl]-1H-tetrazole;
5-[4-[4-[[1-butyl-3-(1-oxo-2-phenylethyl)-1H-1,2,4-triazol-5-yl]methyl]phenyl]-3-pyridinyl]-1H-tetrazole;
5-[4-[4-[[1-butyl-3-(1,1-dimethoxypropyl)-1H-1,2,4-triazol-5-yl]methyl]phenyl]-3-pyridinyl]-1H-tetrazole;
5-[4-[4-[[1-butyl-3-(1,1-dimethoxybutyl)-1H-1,2,4-triazol-5-yl]methyl]phenyl]-3-pyridinyl]-1H-tetrazole;
5-[4-[4-[[1-butyl-3-(1,1-dimethoxypentyl)-1H-1,2,4-triazol-5-yl]methyl]phenyl]-3-pyridinyl]-1H-tetrazole;
5-[4-[4-[[1-butyl-3-(1-oxopropyl)-1H-1,2,4-triazol-5-yl]methyl]phenyl]-3-pyridinyl]-1H-tetrazole;
5-[4-[4-[[1-butyl-3-(1-oxobutyl)-1H-1,2,4-triazol-5-yl]methyl]phenyl]-3-pyridinyl]-1H-tetrazole;
5-[4-[4-[[1-butyl-3-(1-oxopentyl)-1H-1,2,4-triazol-5-yl]methyl]phenyl]-3-pyridinyl]-1H-tetrazole;
5-[4-[4-[[1-butyl-3-(1,1-difluorobutyl)-1H-1,2,4-triazol-5-yl]methyl]phenyl]-3-pyridinyl]-1H-tetrazole;
5-[4-[4-[(1-pentyl-3-methyl-1H-1,2,4-triazol-5-yl)methyl]phenyl]-3-pyridinyl]-1H-tetrazole;
5-[4-[4-[(1-pentyl-3-ethyl-1H-1,2,4-triazol-5-yl)methyl]phenyl]-3-pyridinyl]-1H-tetrazole;
5-[4-[4-[(1-pentyl-3-propyl-1H-1,2,4-triazol-5-yl)methyl]phenyl]-3-pyridinyl]-1H-tetrazole;
5-[4-[4-[(1-pentyl-3-isopropyl-1H-1,2,4-triazol-5-yl)methyl]phenyl]-3-pyridinyl]-1H-tetrazole;
5-[4-[4-[(1-pentyl-3-butyl-1H-1,2,4-triazol-5-yl)methyl]phenyl]-3-pyridinyl]-1H-tetrazole;
5-[4-[4-[(1-pentyl-3-secbutyl-1H-1,2,4-triazol-5-yl)methyl]phenyl]-3-pyridinyl]-1H-tetrazole;
5-[4-[4-[(1-pentyl-3-isobutyl-1H-1,2,4-triazol-5-yl)methyl]phenyl]-3-pyridinyl]-1H-tetrazole;
5-[4-[4-[(1-pentyl-3-tertbutyl-1H-1,2,4-triazol-5-yl)methyl]phenyl]-3-pyridinyl]-1H-tetrazole;
5-[4-[4-[(1,3-dipentyl-1H-1,2,4-triazol-5-yl)methyl]phenyl]-3-pyridinyl]-1H-tetrazole;
5-[4-[4-[(1-pentyl-3-isopentyl-1H-1,2,4-triazol-5-yl)methyl]phenyl]-3-pyridinyl]-1H-tetrazole;
5-[4-[4-[(1-pentyl-3-cyclohexyl-1H-1,2,4-triazol-5-yl)methyl]phenyl]-3-pyridinyl]-1H-tetrazole;
5-[4-[4-[(1-pentyl-3-cyclohexylmethyl-1H-1,2,4-triazol-5-yl)methyl]phenyl]-3-pyridinyl]-1H-tetrazole;
5-[4-[4-[[1-pentyl-3-(2-cyclohexylethyl)-1H-1,2,4triazol-5-yl]methyl]phenyl]-3-pyridinyl]-1H-tetrazole;
5-[4-[4-[(1-pentyl-3-phenyl-1H-1,2,4-triazol-5-yl)methyl]phenyl]-3-pyridinyl]-1H-tetrazole;
5-[4-[4-[(1-pentyl-3-phenylmethyl-1H-1,2,4-triazol-5-yl)methyl]phenyl]-3-pyridinyl]-1H-tetrazole;
5-[4-[4-[[1-pentyl-3-(2-phenylethyl)-1H-1,2,4-triazol-5-yl]methyl]phenyl]-3-pyridinyl]-1H-tetrazole;
5-[4-[4-[(1-pentyl-3-cyclohexanoyl-1H-1,2,4-triazol-5-yl)methyl]phenyl]-3-pyridinyl]-1H-tetrazole;
5-[4-[4-[[1-pentyl-3-(1-oxo-2-cyclohexylethyl)-1H-1,2,4-triazol-5-yl]methyl]phenyl]-3-pyridinyl]-1H-tetrazole;
5-[4-[4-[(1-pentyl-3-benzoyl-1H-1,2,4-triazol-5-yl)methyl]phenyl]-3-pyridinyl]-1H-tetrazole;
5-[4-[4-[[1-pentyl-3-(1-oxo-2-phenylethyl)-1H-1,2,4-triazol-5-yl]methyl]phenyl]-3-pyridinyl]-1H-tetrazole;
5-[4-[4-[[1-pentyl-3-(1,1-dimethoxypropyl)-1H-1,2,4-triazol-5-yl]methyl]phenyl]-3-pyridinyl]-1H-tetrazole;
5-[4-[4-[[1-pentyl-3-(1,1-dimethoxybutyl)-1H-1,2,4-triazol-5-yl]methyl]phenyl]-3-pyridinyl]-1H-tetrazole;
5-[4-[4-[[1-pentyl-3-(1,1-dimethoxypentyl)-1H-1,2,4-triazol-5-yl]methyl]phenyl]-3-pyridinyl]-1H-tetrazole;
5-[4-[4-[[1-pentyl-3-(1-oxopropyl)-1H-1,2,4-triazol-5-yl]methyl]phenyl]-3-pyridinyl]-1H-tetrazole;
5-[4-[4-[[1-pentyl-3-(1-oxobutyl)-1H-1,2,4-triazol-5-yl]methyl]phenyl]-3-pyridinyl]-1H-tetrazole;
5-[4-[4-[[1-pentyl-3-(1-oxopentyl)-1H-1,2,4-triazol-5-yl]methyl]phenyl]-3-pyridinyl]-1H-tetrazole;
5-[4-[4-[[1-pentyl-3-(1,1-difluorobutyl)-1H-1,2,4-triazol-5-yl]methyl]phenyl]-3-pyridinyl]-1H-tetrazole;

A family of specific compounds of more particular interest within Formula VI consists of the following compounds:
5-[4-[4-[(1-butyl-3-methyl-1H-1,2,4-triazol-5-yl)methyl]phenyl]-3-pyridinyl]-1H-tetrazole;
5-[4-[4-[(1-butyl-3-ethyl-1H-1,2,4-triazol-5-yl)methyl]phenyl]-3-pyridinyl]-1H-tetrazole;
5-[4-[4-[(1-butyl-3-propyl-1H-1,2,4-triazol-5-yl)methyl]phenyl]-3-pyridinyl]-1H-tetrazole;
5-[4-[4-[(1-butyl-3-isopropyl-1H-1,2,4-triazol-5-yl)methyl]phenyl]-3-pyridinyl]-1H-tetrazole;
5-[4-[4-[(1,3-dibutyl-1H-1,2,4-triazol-5-yl)methyl]phenyl]-3-pyridinyl]-1H-tetrazole;
5-[4-[4-[(1-butyl-3-secbutyl-1H-1,2,4-triazol-5-yl)methyl]phenyl]-3-pyridinyl]-1H-tetrazole;
5-[4-[4-[(1-butyl-3-isobutyl-1H-1,2,4-triazol-5-yl)methyl]phenyl]-3-pyridinyl]-1H-tetrazole;
5-[4-[4-[(1-butyl-3-tertbutyl-1H-1,2,4-triazol-5-yl)methyl]phenyl]-3-pyridinyl]-1H-tetrazole;
5-[4-[4-[(1-butyl-3-pentyl-1H-1,2,4-triazol-5-yl)methyl]phenyl]-3-pyridinyl]-1H-tetrazole;
5-[4-[4-[(1-butyl-3-isopentyl-1H-1,2,4-triazol-5-yl)methyl]phenyl]-3-pyridinyl]-1H-tetrazole;
5-[4-[4-[(1-butyl-3-cyclohexyl-1H-1,2,4-triazol-5-yl)methyl]phenyl]-3-pyridinyl]-1H-tetrazole;
5-[4-[4-[(1-butyl-3-cyclohexylmethyl-1H-1,2,4-triazol-5-yl)methyl]phenyl]-3-pyridinyl]-1H-tetrazole;
5-[4-[4-[[1-butyl-3-(2-cyclohexylethyl)-1H-1,2,4-triazol-5-yl]methyl]phenyl]-3-pyridinyl]-1H-tetrazole;
5-[4-[4-[(1-butyl-3-phenyl-1H-1,2,4-triazol-5-yl)methyl]phenyl]-3-pyridinyl]-1H-tetrazole;
5-[4-[4-[(1-butyl-3-phenylmethyl-1H-1,2,4-triazol-5-yl)methyl]phenyl]-3-pyridinyl]-1H-tetrazole; and
5-[4-[4-[[1-butyl-3-(2-phenylethyl)-1H-1,2,4-triazol-5-yl]methyl]phenyl]-3-pyridinyl]-1H-tetrazole.

Another subclass of compounds of Formula I which is of even more particular interest consists of those compounds of Formula VII

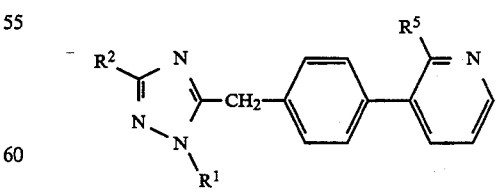

wherein m is one; wherein $R^1$ is selected from methyl, ethyl, n-propyl, isopropyl, n-butyl, sec-butyl, isobutyl, tert-butyl, 4-methylbutyl, n-pentyl, neopentyl, phenyl, benzyl, phenethyl, cyclohexyl, cyclohexylmethyl, 2-butenyl, 3-butenyl, 2-butynyl, 3-butynyl and 2-hydroxybutyl; wherein $R^2$ is selected from ethyl, n-propyl, isopropyl, n-butyl, sec-butyl, isobutyl, 4-methylbutyl, n-pentyl, 1-oxo-2-phenylethyl, 1-oxo-2-cyclohexylethyl, 1,1-difluoro-2-phenylethyl, 1,1-difluoro-2-cyclohexylethyl, 2-cyclohexylethyl, 1,1-difluoro-3-cyclohexylpropyl, 1,1-dimethoxybutyl, 1,1-difluoroethyl, 1,1-difluoropropyl, 1,1-difluorobutyl, 1,1-difluoropentyl, benzyl, 2-phenylethyl, 1,1-difluoro-3-phenylpropyl, cyclohexylmethyl, cyclohexanoyl, 1-butenyl, 2-butenyl, 3-butenyl, 1-butynyl, 2-butynyl, 3-butynyl, propylthio and butylthio; wherein $R^5$ is an acidic group selected from $CO_2H$ and

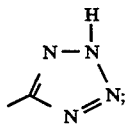

or a tautomer thereof or a pharmaceutically-acceptable salt thereof.

A family of specific compounds of particular interest within Formula VII consists of the following compounds:

3-[4-[(1-propyl-3-methyl-1H-1,2,4-triazol-5-yl)methyl]phenyl]-2-pyridinecarboxylic acid;
3-[4-[(1-propyl-3-ethyl-1H-1,2,4-triazol-5-yl)methyl]phenyl]-2-pyridinecarboxylic acid;
3-[4-[(1,3-di-propyl-1H-1,2,4-triazol-5-yl)methyl]phenyl]-2-pyridinecarboxylic acid;
3-[4-[(1-propyl-3-isopropyl-1H-1,2,4-triazol-5-yl)methyl]phenyl]-2-pyridinecarboxylic acid;
3-[4-[(1-propyl-3-butyl-1H-1,2,4-triazol-5-yl)methyl]phenyl]-2-pyridinecarboxylic acid;
3-[4-[(1-propyl-3-secbutyl-1H-1,2,4-triazol-5-yl)methyl]phenyl]-2-pyridinecarboxylic acid;
3-[4-[(1-propyl-3-isobutyl-1H-1,2,4-triazol-5-yl)methyl]phenyl]-2-pyridinecarboxylic acid;
3-[4-[(1-propyl-3-butyl-1H-1,2,4-triazol-5-yl)methyl]phenyl]-2-pyridinecarboxylic acid;
3-[4-[(1-propyl-3-tertbutyl-1H-1,2,4-triazol-5-yl)methyl]phenyl]-2-pyridinecarboxylic acid;
3-[4-[(1-propyl-3-pentyl-1H-1,2,4-triazol-5-yl)methyl]phenyl]-2-pyridinecarboxylic acid;
3-[4-[(1-propyl-3-isopentyl-1H-1,2,4-triazol-5-yl)methyl]phenyl]-2-pyridinecarboxylic acid;
3-[4-[(1-propyl-3-cyclohexyl-1H-1,2,4-triazol-5-yl)methyl]phenyl]-2-pyridinecarboxylic acid;
3-[4-[(1-propyl-3-cyclohexylmethyl-1H-1,2,4-triazol-5-yl)methyl]phenyl]-2-pyridinecarboxylic acid;
3-[4-[[1-propyl-3-(2-cyclohexylethyl)-1H-1,2,4-triazol-5-yl]methyl]phenyl]-2-pyridinecarboxylic acid;
3-[4-[(1-propyl-3-phenyl-1H-1,2,4-triazol-5-yl)methyl]phenyl]-2-pyridinecarboxylic acid;
3-[4-[(1-propyl-3-phenylmethyl-1H-1,2,4-triazol-5-yl)methyl]phenyl]-2-pyridinecarboxylic acid;
3-[4-[[1-propyl-3-(2-phenylethyl)-1H-1,2,4-triazol-5-yl]methyl]phenyl]-2-pyridinecarboxylic acid;
3-[4-[(1-propyl-3-cyclohexanoyl-1H-1,2,4-triazol-5-yl)methyl]phenyl]-2-pyridinecarboxylic acid;
3-[4-[[1-propyl-3-(1-oxo-2-cyclohexylethyl)-1H-1,2,4-triazol-5-yl]methyl]phenyl]-2-pyridinecarboxylic acid;
3-[4-[[1-propyl-3-benzoyl-1H-1,2,4-triazol-5-yl]methyl]phenyl]-2-pyridinecarboxylic acid;
3-[4-[[1-propyl-3-(1-oxo-2-phenylethyl)-1H-1,2,4-triazol-5-yl]methyl]phenyl]-2-pyridinecarboxylic acid;
3-[4-[[1-propyl-3-(1,1-dimethoxypropyl)-1H-1,2,4-triazol-5-yl]methyl]phenyl]-2-pyridinecarboxylic acid;
3-[4-[[1-propyl-3-(1,1-dimethoxybutyl)-1H-1,2,4-triazol-5-yl]methyl]phenyl]-2-pyridinecarboxylic acid;
3-[4-[[1-propyl-3-(1,1-dimethoxypentyl)-1H-1,2,4-triazol-5-yl]methyl]phenyl]-2-pyridinecarboxylic acid;
3-[4-[[1-propyl-3-(1-oxopropyl)-1H-1,2,4-triazol-5-yl]methyl]phenyl]-2-pyridinecarboxylic acid;
3-[4-[[1-propyl-3-(1-oxobutyl)-1H-1,2,4-triazol-5-yl]methyl]phenyl]-2-pyridinecarboxylic acid;
3-[4-[[1-propyl-3-(1-oxopentyl)-1H-1,2,4-triazol-5-yl]methyl]phenyl]-2-pyridinecarboxylic acid;
3-[4-[[1-propyl-3-(1,1-difluorobutyl)-1H-1,2,4-triazol-5-yl]methyl]phenyl]-2-pyridinecarboxylic acid;
3-[4-[(1-butyl-3-methyl-1H-1,2,4-triazol-5-yl)methyl]phenyl]-2-pyridinecarboxylic acid;
3-[4-[(1-butyl-3-ethyl-1H-1,2,4-triazol-5-yl)methyl]phenyl]-2-pyridinecarboxylic acid;
3-[4-[(1-butyl-3-propyl-1H-1,2,4-triazol-5-yl)methyl]phenyl]-2-pyridinecarboxylic acid;
3-[4-[(1-butyl-3-isopropyl-1H-1,2,4-triazol-5-yl)methyl]phenyl]-2-pyridinecarboxylic acid;
3-[4-[(1,3-dibutyl-1H-1,2,4-triazol-5-yl)methyl]phenyl]-2-pyridinecarboxylic acid;
3-[4-[(1-butyl-3-secbutyl-1H-1,2,4-triazol-5-yl)methyl]phenyl]-2-pyridinecarboxylic acid;
3-[4-[(1-butyl-3-isobutyl-1H-1,2,4-triazol-5-yl)methyl]phenyl]-2-pyridinecarboxylic acid;
3-[4-[(1-butyl-3-butyl-1H-1,2,4-triazol-5-yl)methyl]phenyl]-2-pyridinecarboxylic acid;
3-[4-[(1-butyl-3-tertbutyl-1H-1,2,4-triazol-5-yl)methyl]phenyl]-2-pyridinecarboxylic acid;
3-[4-[(1-butyl-3-pentyl-1H-1,2,4-triazol-5-yl)methyl]phenyl]-2-pyridinecarboxylic acid;
3-[4-[(1-butyl-3-isopentyl-1H-1,2,4-triazol-5-yl)methyl]phenyl]-2-pyridinecarboxylic acid;
3-[4-[(1-butyl-3-cyclohexyl-1H-1,2,4-triazol-5-yl)methyl]phenyl]-2-pyridinecarboxylic acid;
3-[4-[(1-butyl-3-cyclohexylmethyl-1H-1,2,4-triazol-5-yl)methyl]phenyl]-2-pyridinecarboxylic acid;
3-[4-[[1-butyl-3-(2-cyclohexylethyl)-1H-1,2,4-triazol-5-yl]methyl]phenyl]-2-pyridinecarboxylic acid;
3-[4-[(1-butyl-3-phenyl-1H-1,2,4-triazol-5-yl)methyl]phenyl]-2-pyridinecarboxylic acid;
3-[4-[(1-butyl-3-phenylmethyl-1H-1,2,4-triazol-5-yl)methyl]phenyl]-2-pyridinecarboxylic acid;
3-[4-[[1-butyl-3-(2-phenylethyl)-1H-1,2,4-triazol-5-yl]methyl]phenyl]-2-pyridinecarboxylic acid;
3-[4-[(1-butyl-3-cyclohexanoyl-1H-1,2,4-triazol-5-yl)methyl]phenyl]-2-pyridinecarboxylic acid;
3-[4-[[1-butyl-3-(1-oxo-2-cyclohexylethyl)-1H-1,2,4-triazol-5-yl]methyl]phenyl]-2-pyridinecarboxylic acid;
3-[4-[[1-butyl-3-benzoyl-1H-1,2,4-triazol-5-yl]methyl]phenyl]-2-pyridinecarboxylic acid;
3-[4-[[1-butyl-3-(1-oxo-2-phenylethyl)-1H-1,2,4-triazol-5-yl]methyl]phenyl]-2-pyridinecarboxylic acid;
3-[4-[[1-butyl-3-(1,1-dimethoxypropyl)-1H-1,2,4-triazol-5-yl]methyl]phenyl]-2-pyridinecarboxylic acid;
3-[4-[[1-butyl-3-(1,1-dimethoxybutyl)-1H-1,2,4-triazol-5-yl]methyl]phenyl]-2-pyridinecarboxylic acid;
3-[4-[[1-butyl-3-(1,1-dimethoxypentyl)-1H-1,2,4-triazol-5-yl]methyl]phenyl]-2-pyridinecarboxylic acid;
3-[4-[[1-butyl-3-(1-oxopropyl)-1H-1,2,4-triazol-5-yl]methyl]phenyl]-2-pyridinecarboxylic acid;

3-[4-[[1-butyl-3-(1-oxobutyl)-1H-1,2,4-triazol-5-yl]methyl]phenyl]-2-pyridinecarboxylic acid;

3-[4-[[1-butyl-3-(1-oxopentyl)-1H-1,2,4-triazol-5-yl]methyl]phenyl]-2-pyridinecarboxylic acid;

3-[4-[[1-butyl-3-(1,1-difluorobutyl)-1H-1,2,4-triazol-5-yl]methyl]phenyl]-2-pyridinecarboxylic acid;

3-[4-[(1-pentyl-3-methyl-1H-1,2,4-triazol-5-yl)methyl]phenyl]-2-pyridinecarboxylic acid;

3-[4-[(1-pentyl-3-ethyl-1H-1,2,4-triazol-5-yl)methyl]phenyl]-2-pyridinecarboxylic acid;

3-[4-[(1-pentyl-3-propyl-1H-1,2,4-triazol-5-yl)methyl]phenyl]-2-pyridinecarboxylic acid;

3-[4-[(1-pentyl-3-isopropyl-1H-1,2,4-triazol-5yl)methyl]phenyl]-2-pyridinecarboxylic acid;

3-[4-[(1-pentyl-3-butyl-1H-1,2,4-triazol-5yl)methyl]phenyl]-2 -pyridinecarboxylic acid;

3-[4-[(1-pentyl-3-secbutyl-1H-1,2,4-triazol-5yl)methyl]phenyl]-2 -pyridinecarboxylic acid;

3-[4-[(1-pentyl-3-isobutyl-1H-1,2,4-triazol-5yl)methyl]phenyl]-2 -pyridinecarboxylic acid;

3-[4-[(1-pentyl-3-butyl-1H-1,2,4-triazol-5yl)methyl]phenyl]-2 -pyridinecarboxylic acid;

3-[4-[(1-pentyl-3-tertbutyl-1H-1,2,4-triazol-5yl)methyl]phenyl]-2 -pyridinecarboxylic acid;

3-[4-[(1,3-dipentyl-1H-1,2,4-triazol-5yl)methyl]phenyl]-2-pyridinecarboxylic acid;

3-[4-[(1-pentyl-3-isopentyl-1H-1,2,4-triazol-5yl)methyl]phenyl]-2-pyridinecarboxylic acid;

3-[4-[(1-pentyl-3-cyclohexyl-1H-1,2,4-triazol-5yl)methyl]phenyl]-2 -pyridinecarboxylic acid;

3-[4-[(1-pentyl-3-cyclohexylmethyl-1H-1,2,4-triazol-5yl)methyl]phenyl]-2 -pyridinecarboxylic acid;

3-[4-[[1-pentyl-3-(2-cyclohexylethyl)-1H-1,2,4-triazol-5-yl]methyl]phenyl]-2-pyridinecarboxyl is acid;

3-[4-[(1-pentyl-3-phenyl-1H-1,2,4-triazol-5yl)methyl]phenyl]-2-pyridinecarboxylic acid;

3-[4- [(1-pentyl-3-phenylmethyl-1H-1,2,4-triazol-5yl)methyl]phenyl]-2-pyridinecarboxylic acid;

3-[4-[[1-pentyl-3-(2-phenylethyl) -1H-1, 2, 4-triazol-5yl]methyl]phenyl]-2 -pyridinecarboxylic acid;

3-[4-[(1-pentyl-3-cyclohexanoyl-1H-1,2,4-triazol-5yl)methyl]phenyl]-2 -pyridinecarboxylic acid;

3-[4-[[1-pentyl-3-(1-oxo-2-cyclohexylethyl )-1H-1,2,4-triazol-5-yl]methyl]phenyl]-2-pyridinecarboxylic acid;

3-[4-[[1-pentyl-3-benzoyl-1H-1,2,4-triazol-5yl]methyl]phenyl]-2 -pyridinecarboxylic acid;

3-[4-[[1-pentyl-3-(1-oxo-2-phenylethyl)-1H-1,2,4-triazol-5-yl]methyl]phenyl]-2 -pyridinecarboxylic acid;

3-[4-[[1-pentyl-3-(1, 1-dimethoxypropyl) -1H-1,2,4-triazol-5-yl]methyl]phenyl]-2-pyridinecarboxylic acid;

3-[4-[[1-pentyl-3-(1,1-dimethoxybutyl) -1H-1,2,4-triazol-5-yl]methyl]phenyl]-2 -pyridinecarboxylic acid;

3-[4-[[1-pentyl-3-(1,1-dimethoxypentyl) -1H-1,2,4-triazol-5-yl]methyl]phenyl]-2 -pyridinecarboxylic acid;

3-[4-[[1-pentyl-3-(1-oxopropyl)-1H-1,2,4-triazol-5yl]methyl]phenyl]-2 -pyridinecarboxylic acid;

3-[4-[[1-pentyl-3-(1-oxobutyl) -1H-1,2,4-triazol-5yl]methyl]phenyl ]-2-pyridinecarboxylic acid;

3-[4-[[1-pentyl-3-(1-oxopentyl)-1H-1,2,4-triazol-5yl]methyl]phenyl]-2-pyridinecarboxylic acid;

3-[4-[[1-pentyl-3-(1, 1-difluorobutyl)-1H-1,2,4-triazol-5-yl]methyl]phenyl]-2-pyridinecarboxylic acid;

5-[3-[4-[(1-propyl-3-methyl-1H-1,2,4-triazol-5yl)methyl]phenyl]-2-pyridinyl]-1H-tetrazole;

5-[3-[4-[(1 -propyl-3-ethyl-1H-1,2,4-triazol-5yl)methyl]phenyl]-2-pyridinyl]-1H-tetrazole;

5-[3-[4-[(1, 3-dipropyl-1H-1,2,4-triazol-5yl)methyl]phenyl]-2-pyridinyl]-1H-tetrazole;

5-[3-[4-[(1-propyl-3-isopropyl-1H-1,2,4-triazol-5yl)methyl]phenyl]-2 -pyridinyl]-1H-tetrazole;

5-[3-[4-[(1-propyl-3-butyl-1H-1,2,4-triazol-5yl)methyl]phenyl]-2-pyridinyl]-1H-tetrazole;

5-[3-[4-[(1-propyl-3-secbutyl-1H-1,2,4-triazol-5yl)methyl]phenyl]-2-pyridinyl]-1H-tetrazole;

5-[3-[4-[(1-propyl-3-isobutyl-1H-1,2,4-triazol-5yl)methyl]phenyl]-2-pyridinyl]-1H-tetrazole;

5-[3-[4-[(1-propyl-3-tertbutyl-1H-1,2,4-triazol-5yl)methyl]phenyl]-2-pyridinyl]-1H-tetrazole;

5-[3-[4-[(1-propyl-3-pentyl-1H-1,2,4-triazol-5yl)methyl]phenyl]-2-pyridinyl]-1H-tetrazole;

5-[3-[4-[(1-propyl-3-isopentyl-1H-1,2,4-triazol-5yl)methyl]phenyl]-2-pyridinyl]-1H-tetrazole;

5-[3-[4-[(1-propyl-3-cyclohexyl-1H-1,2,4-triazol-5yl)methyl]phenyl]-2-pyridinyl]-1H-tetrazole;

5-[3-[4-[(1-propyl-3-cyclohexylmethyl-1H-1,2,4-triazol-5-yl) methyl]phenyl]-2-pyridinyl]-1H-tetrazole;

5-[3-[4-[[1-propyl-3-(2-cyclohexylethyl) -1H-1,2,4-triazol-5-yl]methyl]phenyl]-2-pyridinyl]-1H-tetrazole;

5-[3-[4-[(1 -propyl-3-phenyl-1H-1, 2, 4-triazol-5yl)methyl]phenyl]-2-pyridinyl]-1H-tetrazole;

5-[3-[4-[(1-propyl-3-phenylmethyl-1H-1,2,4-triazol-5yl)methyl]phenyl]-2-pyridinyl]-1H-tetrazole;

5-[3-[4-[[1-propyl-3-(2-phenylethyl)-1H-1,2,4-triazol-5yl]methyl]phenyl]-2 -pyridinyl]-1H-tetrazole;

5-[3-[4-[(1-propyl-3-cyclohexanoyl-1H-1,2,4-triazol-5yl)methyl]phenyl]-2-pyridinyl]-1H-tetrazole;

5- [3- [4-[[1 -propyl-3-(1-oxo-2-cyclohexylethyl ) -1H-1,2,4-triazol-5-yl]methyl]phenyl]-2-pyridinyl]-1H-tetrazole;

5-[3-[4-[(1-propyl-3-benzoyl-1H-1,2,4-triazol-5yl)methyl]phenyl]-2 -pyridinyl]-1H-tetrazole;

5-[3-[4-[[1 -propyl-3-(1-oxo-2-phenylethyl ) -1H-1,2,4-triazol-5-yl]methyl]phenyl]-2 -pyridinyl]-1H-tetrazole;

5-[3-[4-[[1 -propyl-3-(1, 1 -dimethoxypropyl)-1H-1,2,4-triazol-5-yl]methyl]phenyl]-2-pyridinyl]-1H-tetrazole;

5-[3-[4-[[1 -propyl-3-(1,1 -dimethoxybutyl ) -1H-1,2,4-triazol-5-yl]methyl]phenyl]-2-pyridinyl]-1H-tetrazole;

5-[3-[4-[[1-propyl-3-(1,1-dimethoxypentyl ) -1H-1,2,4-triazol-5-yl]methyl]phenyl]-2-pyridinyl]-1H-tetrazole;

5-[3-[4-[[1-propyl-3-(1-oxopropyl)-1H-1,2,4-triazol-5yl]methyl]phenyl]-2-pyridinyl]-1H-tetrazole;

5-[3-[4-[[1-propyl-3-(1-oxobutyl)-1H-1,2,4-triazol-5yl]methyl]phenyl]-2-pyridinyl]-1H-tetrazole;

5-[3-[4-[[1-propyl-3-(1-oxopentyl)-1H-1,2,4-triazol-5yl]methyl]phenyl]-2-pyridinyl]-1H-tetrazole;

5-[3-[4-[[1 -propyl-3-(1 -difluorobutyl )-1H-1,2,4-triazol5-yl]methyl]phenyl]-2-pyridinyl]-1H-tetrazole;

5-[3-[4-[(1-butyl-3-methyl-1H-1,2,4-triazol-5yl)methyl]phenyl]-2-pyridinyl]-1H-tetrazole;

5-[3-[4-[(1-butyl-3-ethyl-1H-1,2,4-triazol-5yl)methyl]phenyl]-2 -pyridinyl]-1H-tetrazole;

5- [3-[4-[(1-butyl-3-propyl-1H-1,2,4-triazol-5yl)methyl]phenyl]-2-pyridinyl]-1H-tetrazole;

5-[3-[4-[(1-butyl-3-isopropyl-1H-1,2,4-triazol-5yl)methyl]phenyl]-2-pyridinyl]-1H-tetrazole;

5-[3-[4-[(1, 3-dibutyl-1H-1,2,4-triazol-5yl) methyl]phenyl]-2-pyridinyl]-1H-tetrazole;
5-[3-[4-[(1-butyl-3-secbutyl-1H-1,2,4-triazol-5-yl)methyl]phenyl]-2-pyridinyl]-1H-tetrazole;
5-[3-[4-[(1-butyl-3-isobutyl-1H-1,2,4-triazol-5yl) methyl]phenyl]-2-pyridinyl]-1H-tetrazole;
5-[3-[4-[(1-butyl-3-tertbutyl-1H-1,2,4-triazol-5yl) methyl]phenyl]-2-pyridinyl]-1H-tetrazole;
5-[3-[4-[(1-butyl-3-pentyl-1H-1,2,4-triazol-5yl)methyl]phenyl]-2-pyridinyl]-1H-tetrazole;
5-[3-[4-[( 1-butyl-3-isopentyl-1H-1,2,4-triazol-5yl) methyl]phenyl]-2-pyridinyl]-1H-tetrazole;
5-[3-[4-[(1-butyl-3-cyclohexyl-1H-1,2,4-triazol-5yl)methyl]phenyl]-2-pyridinyl]-1H-tetrazole;
5-[3-[4-[(1-butyl-3-cyclohexylmethyl-1H-1,2,4-triazol-5yl)methyl]phenyl]-2-pyridinyl]-1H-tetrazole;
5-[3-[4-[[1-butyl-3-(2-cyclohexylethyl)-1H-1,2,4-triazol-5-yl]methyl]phenyl]-2-pyridinyl]-1H-tetrazole;
5-[3-[4-[(1-butyl-3-phenyl-1H-1,2,4-triazol-5yl) methyl]phenyl]-2-pyridinyl]-1H-tetrazole;
5-[3-[4-[(1-butyl-3-phenylmethyl-1H-1,2,4-triazol-5yl)methyl]phenyl]-2-pyridinyl]-1H-tetrazole;
5-[3-[4-[[1-butyl-3-(2-phenylethyl)-1H-1, 2, 4-triazol-5-yl]methyl]phenyl]-2-pyridinyl]-1H-tetrazole;
5-[3-[4-[(1-butyl-3-cyclohexanoyl-1H-1,2,4-triazol-5-yl)methyl]phenyl]-2-pyridinyl]-1H-tetrazole;
5-[3-[4-[[1-butyl-3-(1-oxo-2-cyclohexylethyl)-1H-1,2,4-triazol-5-yl]methyl]phenyl]-2-pyridinyl]-1H-tetrazole;
5-[3-[4-[(1-butyl-3-benzoyl-1H-1,2,4-triazol-5yl)methyl]phenyl]-2-pyridinyl]-1H-tetrazole;
5-[3-[4-[[1-butyl-3-(1-oxo-2-phenylethyl)-1H-1,2,4-triazol-5-yl]methyl]phenyl]-2-pyridinyl]-1H-tetrazole;
5-[3-[4-[[1-butyl-3-(1, 1-dimethoxypropyl)-1H-1,2,4-triazol-5-yl]methyl]phenyl]-2-pyridinyl]-1H-tetrazole;
5-[3-[4-[[1-butyl-3-(1,1-dimethoxybutyl)-1H-1,2,4-triazol-5-yl]methyl]phenyl]-2-pyridinyl]-1H-tetrazole;
5-[3-[4-[[1-butyl-3-(1,1-dimethoxyentyl)-1H-1,2,4-triazol-5-yl]methyl]phenyl]-2-pyridinyl]-1H-tetrazole;
5-[3-[4-[[1-butyl-3-(1-oxopropyl)-1H-1,2,4-triazol-5-yl]methyl]phenyl]-2-pyridinyl]-1H-tetrazole;
5-[3-[4-[[1-butyl-3-(1-oxobutyl )-1H-1,2,4-triazol-5-yl]methyl]phenyl]-2-pyridinyl]-1H-tetrazole;
5-[3-[4-[[1-butyl-3-(1-oxopentyl)-1H-1,2,4-triazol-5yl)methyl]phenyl]-2-pyridinyl]-1H-tetrazole;
5-[3-[4-[[1-butyl-3-(1-difluorobutyl)-1H-1,2,4-triazol-5-yl]methyl]phenyl]-2-pyridinyl]-1H-tetrazole;
5-[3-[4-[(1-pentyl-3-methyl-1H-1,2,4-triazol-5yl)methyl]phenyl]-2-pyridinyl]-1H-tetrazole;
5-[3-[4-[(1-pentyl-3-ethyl-1H-1,2,4-triazol-5-yl)methyl]phenyl]-2-pyridinyl]-1H-tetrazole;
5-[3-[4-[(1-pentyl-3-propyl-1H-1,2,4-triazol-5-yl)methyl]phenyl]-2-pyridinyl]-1H-tetrazole;
5-[3-[4-[(1-pentyl-3-isopropyl-1H-1,2,4-triazol-5-yl)methyl]phenyl]-2-pyridinyl]-1H-tetrazole;
5-[3-[4-[(1-pentyl-3-butyl-1H-1,2,4-triazol-5-yl)methyl]phenyl]-2-pyridinyl]-1H-tetrazole;
5-[3-[4-[(1-pentyl-3-secbutyl-1H-1,2,4-triazol-5-yl)methyl]phenyl]-2-pyridinyl]-1H-tetrazole;
5-[3-[4-[(1-pentyl-3-isobutyl-1H-1,2,4-triazol-5-yl)methyl]phenyl]-2-pyridinyl]-1H-tetrazole;
5-[3-[4-[(1-pentyl-3-tertbutyl-1H-1,2,4-triazol-5-yl)methyl]phenyl]-2-pyridinyl]-1H-tetrazole;

5-[3-[4-[(1,3-dipentyl-1H-1,2,4-triazol-5-yl)methyl]phenyl]-2-pyridinyl]-1H-tetrazole;
5-[3-[4-[(1-pentyl-3-isopentyl-1H-1,2,4-triazol-5-yl)methyl]phenyl]-2-pyridinyl]-1H-tetrazole;
5-[3-[4-[(1-pentyl-3-cyclohexyl-1H-1,2,4-triazol-5-yl)methyl]phenyl]-2-pyridinyl]-1H-tetrazole;
5-[3-[4-[(1-pentyl-3-cyclohexylmethyl-1H-1,2,4-triazol-5-yl) methyl]phenyl]-2-pyridinyl]-1H-tetrazole;
5-[3-[4-[[1-pentyl-3-(2-cyclohexylethyl)-1H-1,2,4-triazol-5-yl]methyl]phenyl]-2-pyridinyl]-1H-tetrazole;
5-[3-[4-[( 1-pentyl-3-phenyl-1H-1,2,4-triazol-5yl)methyl]phenyl]-2-pyridinyl]-1H-tetrazole;
5-[3-[4-[(1-pentyl-3-phenylmethyl-1H-1,2,4-triazol-5-yl)methyl]phenyl]-2-pyridinyl]-1H-tetrazole;
5-[3-[4-[[1-pentyl-3-(2-phenylethyl)-1H-1,2,4-triazol-5-yl]methyl]phenyl]-2-pyridinyl]-1H-tetrazole;
5-[3-[4-[(1-pentyl-3-cyclohexanoyl-1H-1,2,4-triazol-5yl)methyl]phenyl]-2-pyridinyl]-1H-tetrazole;
5-[3-[4-[[1-pentyl-3-(1-oxo-2-cyclohexylethyl)-1H-1,2,4-triazol-5-yl]methyl]phenyl]-2-pyridinyl]-1H-tetrazole;
5-[3-[4-[(1-pentyl-3-benzoyl-1H-1,2,4-triazol-5yl)methyl]phenyl]-2-pyridinyl]-1H-tetrazole;
5-[3-[4-[[1-pentyl-3-(1-oxo-2-phenylethyl)-1H-1,2,4-triazol-5-yl]methyl]phenyl]-2-pyridinyl]-1H-tetrazole;
5-[3-[4-[[1-pentyl-3-(1,1-dimethoxypropyl)-1H-1,2,4-triazol-5-yl]methyl]phenyl]-2-pyridinyl]-1H-tetrazole;
5-[3-[4-[[1-pentyl-3-(1,1-dimethoxybutyl)-1H-1,2,4-triazol-5-yl]methyl]phenyl]-2-pyridinyl]-1H-tetrazole;
5-[3-[4-[[1-pentyl-3-(1,1-dimethoxypentyl)-1H-1,2,4-triazol-5-yl]methyl]phenyl]-2-pyridinyl]-1H-tetrazole;
5-[3-[4-[[1-pentyl-3-(1-oxopropyl)-1H-1,2,4-triazol-5-yl]methyl]phenyl]-2-pyridinyl]-1H-tetrazole;
5-[3-[4-[[1-pentyl-3-(1-oxobutyl)-1H-1,2,4-triazol-5-yl]methyl]phenyl]-2-pyridinyl]-1H-tetrazole;
5-[3-[4-[[1-pentyl-3-(1-oxopentyl)-1H-1,2,4-triazol-5-yl]methyl]phenyl]-2-pyridinyl]-1H-tetrazole; and
5-[3-[4-[[1-pentyl-3-(1-difluorobutyl)-1H-1,2,4-triazol-5-yl]methyl]phenyl]-2-pyridinyl]-1Hetrazole.

A family of specific compounds of more particular interest within Formula VII consists of the following compounds:

5-[3-[4-[(1-butyl-3-methyl-1H-1,2,4-triazol-5-yl)methyl]phenyl]-2-pyridinyl]-1H-tetrazole;
5-[3-[4-[(1-butyl-3-ethyl-1H-1,2,4-triazol-5-yl)methyl]phenyl]-2-pyridinyl]-1H-tetrazole;
5-[3-[4-[(1-butyl-3-propyl-1H-1,2,4-triazol-5-yl)methyl]phenyl]-2-pyridinyl]-1H-tetrazole;
5-[3-[4-[(1-butyl-3-isopropyl-1H-1,2,4-triazol-5-yl)methyl]phenyl]-2-pyridinyl]-1H-tetrazole;
5-[3-[4-[(1,3-dibutyl-1H-1,2,4-triazol-5-yl)methyl]phenyl]-2-pyridinyl]-1H-tetrazole;
5-[3-[4-[(1-butyl-3-secbutyl-1H-1,2,4-triazol-5-yl)methyl]phenyl]-2-pyridinyl]-1H-tetrazole;
5-[3-[4-[(1-butyl-3-isobutyl-1H-1,2,4-triazol-5-yl)methyl]phenyl]-2-pyridinyl]-1H-tetrazole;
5-[3-[4-[(1-butyl-3-tertbutyl-1H-1,2,4-triazol-5-yl)methyl]phenyl]-2-pyridinyl]-1H-tetrazole;
5-[3-[4-[(1-butyl-3-pentyl-1H-1,2,4-triazol-5-yl)methyl]phenyl]-2-pyridinyl]-1H-tetrazole;
5-[3- [4-[(1-butyl-3-isopentyl-1H-1,2,4-triazol-5-yl)methyl]phenyl]-2-pyridinyl]-1H-tetrazole;

5-[3-[4-[(1-butyl-3-cyclohexyl-1H-1,2,4-triazol-5-yl)methyl]phenyl]-2-pyridinyl]-1H-tetrazole;

5-[3-[4-[(1-butyl-3-cyclohexylmethyl-1H-1,2,4-triazol-5-yl)methyl]phenyl]-2-pyridinyl]-1H-tetrazole;

5-[3-[4-[[1-butyl-3-(2-cyclohexylethyl)-1H-1,2,4-triazol-5-yl]methyl]phenyl]-2-pyridinyl]-1H-tetrazole;

5-[3-[4-[(1-butyl-3-phenyl-1H-1,2,4-triazol-5-yl)methyl]phenyl]-2-pyridinyl]-1H-tetrazole;

5-[3-[4-[(1-butyl-3-phenylmethyl-1H-1,2,4-triazol-5-yl)methyl]phenyl]-2-pyridinyl]-1H-tetrazole; and 5-[3-[4-[[1-butyl-3-(2-phenylethyl)-1H-1,2,4-triazol-5-yl]methyl]phenyl]-2-pyridinyl]-1H-tetrazole.

The term "hydrido" denotes a single hydrogen atom (H). This hydrido group may be attached, for example, to an oxygen atom to form a hydroxyl group; or, as another example, one hydrido group may be attached to a carbon atom to form a

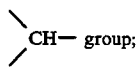

or, as another example, two hydrido groups may be attached to a carbon atom to form a —CH$_2$— group. Where the term "alkyl" is used, either alone or within other terms such as "haloalkyl" and "hydroxyalkyl", the term "alkyl" embraces linear or branched radicals having one to about twenty carbon atoms or, preferably, one to about twelve carbon atoms. More preferred alkyl radicals are "lower alkyl" radicals having one to about ten carbon atoms. Most preferred are lower alkyl radicals having one to about five carbon atoms. The term "cycloalkyl" embraces cyclic radicals having three to about ten ring carbon atoms, preferably three to about six carbon atoms, such as cyclopropyl, cyclobutyl, cyclopentyl and cyclohexyl. The term "haloalkyl" embraces radicals wherein any one or more of the alkyl carbon atoms is substituted with one or more halo groups, preferably selected from bromo, chloro and fluoro. Specifically embraced by the term "haloalkyl" are monohaloalkyl, dihaloalkyl and polyhaloalkyl groups. A monohaloalkyl group, for example, may have either a bromo, a chloro, or a fluoro atom within the group. Dihaloalkyl and polyhaloalkyl groups may be substituted with two or more of the same halo groups, or may have a combination of different halo groups. A dihaloalkyl group, for example, may have two fluoro atoms, such as difluoromethyl and difluorobutyl groups, or two chloro atoms, such as a dichloromethyl group, or one fluoro atom and one chloro atom, such as a fluoro-chloromethyl group. Examples of a polyhaloalkyl are trifluoromethyl, 1,1-difluoroethyl, 2,2,2-trifluoroethyl, perfluoroethyl and 2,2,3,3-tetrafluoropropyl groups. The term "difluoroalkyl" embraces alkyl groups having two fluoro atoms substituted on any one or two of the alkyl group carbon atoms. The terms "alkylol" and "hydroxyalkyl" embrace linear or branched alkyl groups having one to about ten carbon atoms any one of which may be substituted with one or more hydroxyl groups. The term "alkenyl" embraces linear or branched radicals having two to about twenty carbon atoms, preferably three to about ten carbon atoms, and containing at least one carbon-carbon double bond, which carbon-carbon double bond may have either cis or trans geometry within the alkenyl moiety. The term "alkynyl" embraces linear or branched radicals having two to about twenty carbon atoms, preferably two to about ten carbon atoms, and containing at least one carbon-carbon triple bond. The term "cycloalkenyl" embraces cyclic radicals having three to about ten ring carbon atoms including one or more double bonds involving adjacent ring carbons. The terms "alkoxy" and "alkoxyalkyl" embrace linear or branched oxy-containing radicals each having alkyl portions of one to about ten carbon atoms, such as methoxy group. The term "alkoxyalkyl" also embraces alkyl radicals having two or more alkoxy groups attached to the alkyl radical, that is, to form monoalkoxyalkyl and dialkoxyalkyl groups. The "alkoxy" or "alkoxyalkyl" radicals may be further substituted with one or more halo atoms, such as fluoro, chloro or bromo, to provide haloalkoxy or haloalkoxyalkyl groups. The term "alkylthio" embraces radicals containing a linear or branched alkyl group, of one to about ten carbon atoms attached to a divalent sulfur atom, such as a methythio group. Preferred aryl groups are those consisting of one, two, or three benzene rings. The term "aryl" embraces aromatic radicals such as phenyl, naphthyl and biphenyl. The term "aralkyl" embraces aryl-substituted alkyl radicals such as benzyl, diphenylmethyl, triphenylmethyl, phenylethyl, phenylbutyl and diphenylethyl. The terms "benzyl" and "phenylmethyl" are interchangeable. The terms "aryloxy" and "arylthio" denote radical respectively, aryl groups having an oxygen or sulfur atom through which the radical is attached to a nucleus, examples of which are phenoxy and phenylthio. The terms "sulfinyl" and "sulfonyl", whether used alone or linked to other terms, denotes respectively divalent radicals SO and SO$_2$. The term "aralkoxy", alone or within another term, embraces an aryl group attached to an alkoxy group to form, for example, benzyloxy. The term "acyl" whether used alone, or within a term such as acyloxy, denotes a radical provided by the residue after removal of hydroxyl from an organic acid, examples of such radical being acetyl and benzoyl. "Lower alkanoyl" is an example of a more prefered sub-class of acyl. The term "amido" denotes a radical consisting of nitrogen atom attached to a carbonyl group, which radical may be further substituted in the manner described herein. The amido radical can be attached to the nucleus of a compound of the invention through the carbonyl moiety or through the nitrogen atom of the amido radical. The term "alkenylalkyl" denotes a radical having a double-bond unsaturation site between two carbons, and which radical may consist of only two carbons or may be further substituted with alkyl groups which may optionally contain additional double-bond unsaturation. The term "heteroaryl" embraces aromatic ring systems containing one or two hetero atoms selected from oxygen, nitrogen and sulfur in a ring system having five or six ring members, examples of which are thienyl, furanyl, pyridinyl, thiazolyl, pyrimidyl and isoxazolyl. Such heteroaryl may be attached as a substituent through a carbon atom of the heteroaryl ring system, or may be attached through a carbon atom of a moiety substituted on a heteroaryl ring-member carbon atom, for example, through the methylene substituent of imidazolemethyl moiety. Also, such heteroaryl may be attached through a ring nitrogen atom as long as aromaticity of the heteroaryl moiety is preserved after attachment. For any of the foregoing defined radicals, preferred radicals are those containing from one to about ten carbon atoms.

Specific examples of alkyl groups are methyl, ethyl, n-propyl, isopropyl, n-butyl, sec-butyl, isobutyl, tert-butyl, n-pentyl, isopentyl, methylbutyl, dimethylbutyl and neopentyl. Typical alkenyl and alkynyl groups may have one unsaturated bond, such as an allyl group, or may have a plurality of unsaturated bonds, with such plurality of bonds either adjacent, such as allene-type structures, or in conjugation, or separated by several saturated carbons.

Compounds of Formula I have been found to inhibit the action of angiotensin II in mammals. Angiotensin Ii is a potent vasoconstrictor and participates in the formation of aldosterone which regulates sodium and water balance in meals. Thus, compounds of Formula I are therapeutically useful in methods for treating hypertension by administering to a hypertensive patient a therapeutically-effective amount of a compound of Formula I. The phrase "hypertensive patient" means, in this context, a mammalian subject suffering from or afflicted by the effects of hypertension or susceptible to a hypertensive condition if not treated to prevent or control such hypertension.

Also included in the family of compounds of Formula I are isomeric forms including diastereoisomers, regioisomers and the pharmaceutically-acceptable salts thereof. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formula I may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, p-hydroxybenzoic, sailcylic, phenylacetic, mandelic, embonic (pamoic), methansulfonic, ethanesulfonic, 2-hydroxyethanesulfonic, pantothenic, benzenesulfonic, toluenesulfonic, sulfanilic, mesylic, cyclohexylaminosulfonic, stearic, algenic, D-hydroxybutyric, malonic, galactaric and galacturonic acid. Suitable pharmaceutically-acceptable base addition salts of compounds of Formula I include metallic salts made from aluminium, calcium, lithium, magnesium, potassium, sodium and zinc or organic salts made from N,N'-dibenzylethylenediamine, chloroprocaine, choline, diethanolamine, ethylenediamine, meglumine (N-methylglucamine) and procaine. All of these salts may be prepared by conventional means from the corresponding compound of Formula I by reacting, for example, the appropriate acid or base with the compound of Formula I.

General Synthetic Procedures

The compounds of the invention can be synthesized according to the following procedures of Schemes I-XI, wherein the R substituents are as defined for Formula I, above, except where further noted.

Scheme I

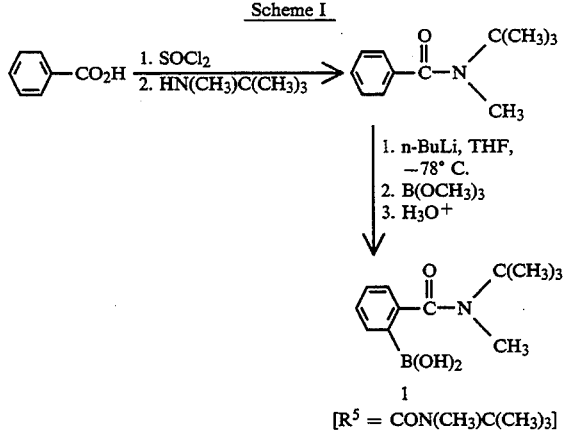

Synthetic Scheme I shows the preparation of the boronic acid 1 where $R^5$ equals N-tertbutyl-N-methylcarboxamide. In step 1, benzoic acid is treated with thionyl chloride to give the corresponding acid chloride which is subsequently reacted with N-tertbutyl-Nmethylamine to give N-tertbutyl-N-methylbenzamide. In step 2, the amide is ortho-metalated and subsequently reacted with trimethyl borate. The free boronic acid I is produced on hydroylsis.

Scheme II

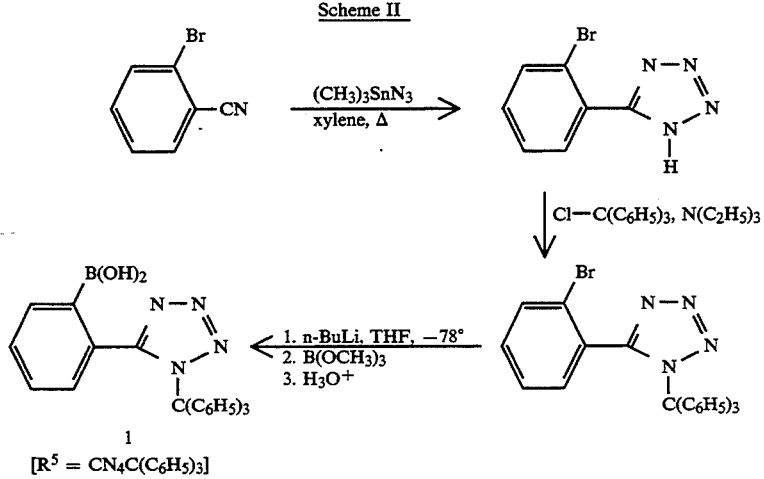

Synthetic Scheme II shows the preparation of the boronic acid 1 where $R^5$ equals N-triphenylmethyl-1H-tetrazole. In step 1, 2-bromobenzonitrile (Aldrich) is reacted with trimethyltin azide to give the corresponding tetrazole. In step 2, the tetrazole is reacted with triphenylmethyl chloride in the presence of triethylamine to give the protected bromophenyltetrazole. In step 3, halogen-metal interchange with n-butyllithium generates the corresponding ortho-lithiated species which is reacted with trimethyl borate. The free boronic acid 1 is produced on hydrolysis.

Scheme III

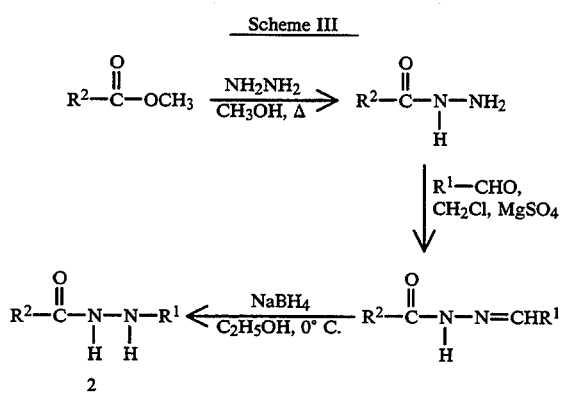

Synthetic Scheme III shows the regiospecific preparation of N²-monoalkylsubstituted hydrazides 2. In step 1, hydrazine is reacted with a methyl ester to give the corresponding unsubstituted hydrazide. In step 2, the hydrazide is reacted with the appropriate aldehyde to give the corresponding imine. In step 3, the imine is reduced with sodium borohydride to give the desired N2-substituted hydrazide 2.

Scheme IV

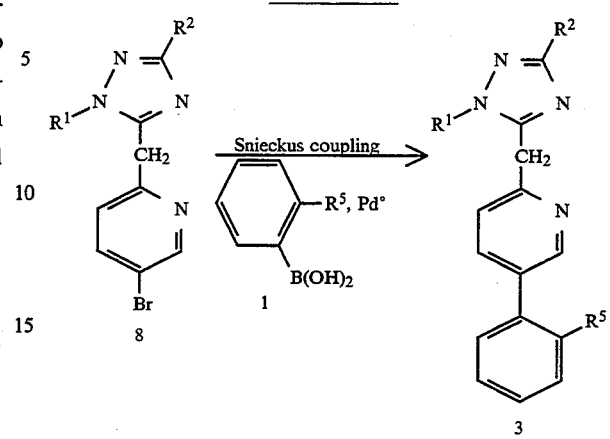

Synthetic Scheme IV shows the preparation of 5-(2-pyridinyl)methyl-1H-1,2,4-triazoles a from 2-picoline (Aldrich). In step 1, 2-picoline is reacted with bromine in the presence of a large excess of aluminum chloride at elevated temperatures to give 5-bromo-2-picoline (4). In step 2, 4 a is reacted with NBS to give the 2-pyridinylmethyl bromide 5. In step 3, 5 is reacted with potassium cyanide to give the 2-pyridinylacetonitrile 6. In step 4, 6 is reacted with hydrogen chloride and ethanol to give the imidate ester hydrochloride which is subsequently converted to the free imidate ester 7 on treatment with ammonia at low temperatures. In step 5, the imidate 7 is reacted with hydrazide 2 (Scheme III) to give the bromotriazole 8. In step 6, the bromotriazole 8 is reacted with the boronic acid 1 (Scheme II) in the presence of a palladium zero catalyst via a Snieckus coupling [see M. J. Sharp and V. Snieckus, *Tetrahedron Lett.*, 5997 (1985)] to give the angiotensin II antagonists 3 of the invention.

Scheme IV

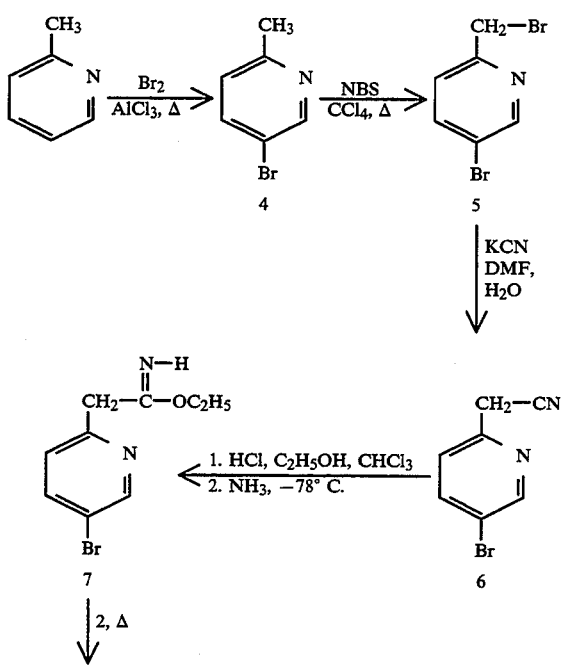

Scheme V

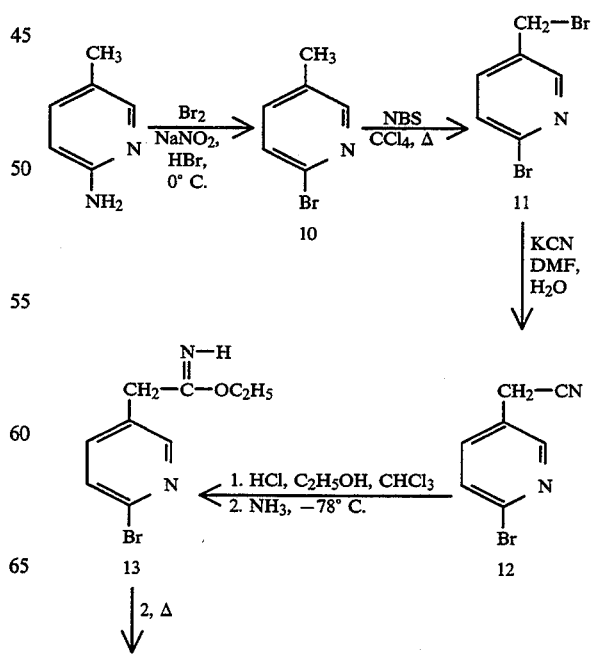

-continued
Scheme V

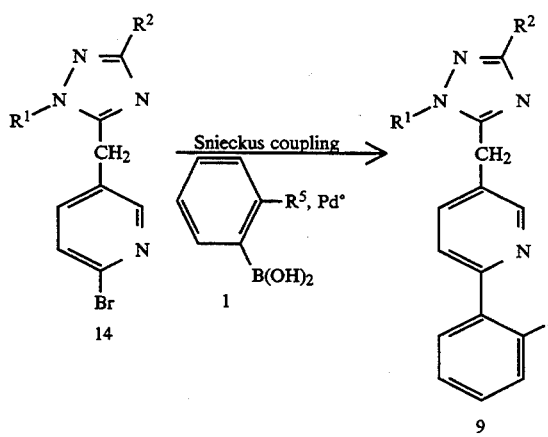

Synthetic Scheme V shows the preparation of 5-(3-pyridinyl)methyl-1H-1,2,4-triazoles a from 2-amino-5-picoline (Aldrich). In step 1, 2-amino-5-picoline is reacted with bromine in the presence of hydrobromic acid and sodium nitrite at 0° C. to give 2-bromo-5-picoline (10). In step 2, 10 is reacted with NBS to give the 3-pyridinylmethyl bromide 11. In step 3, 11 is reacted with potassium cyanide to give the 3-pyridinylacetonitrile 12. In step 4, 12 is reacted with hydrogen chloride and ethanol to give the imidate ester hydrochloride which is subsequently converted to the free imidate ester 13 on treatment with ammonia at low temperatures. In step 5, the imidate 13 is reacted with the hydrazide 2 (Scheme III) to give the bromotriazole 14. In step 6, the bromotriazole 14 is reacted with the boronic acid 1 (Scheme II) in the presence of a palladium zero catalyst via a Snieckus coupling [see M. J. Sharp and V. Snieckus, Tetrahedron Lett., 5997 (1985)] to give the angiotensin II antagonists 9 of this invention.

Scheme VI
CO₂H

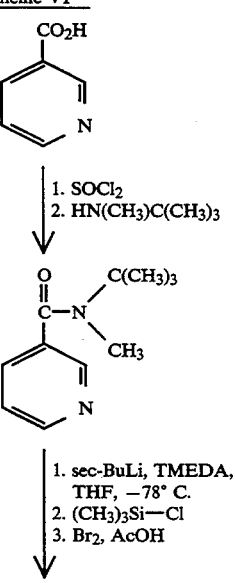

1. sec-BuLi, TMEDA,
   THF, -78° C.
2. (CH₃)₃Si—Cl
3. Br₂, AcOH

-continued
Scheme VI

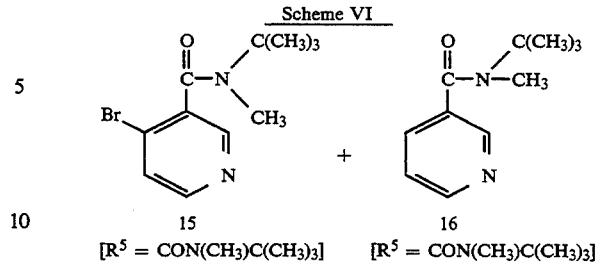

Synthetic Scheme VI shows the preparation of the 4-bromopyridine coupling reagent 15 [R⁵=CON(CH₃)C(CH₃)₃] and the 2-bromopyridine coupling reagent 16 [R⁵=CON(CH₃)C(CH₃)₃] from nicotinic acid. In step 1, N-tertbuty-N-methylnicotinamide is prepared from nicotinoyl chloride and N-tertbutyl-N-methylamine. In step 2, ortho-metalalion with sec-butyllithium gives a mixture of regioanions which are reacted with trimethylsilyl chloride; subsequent conversion to the corresponding bromides on treatment with bromine in acetic acid and separation of the regioisomers by chromatography provides 15 and 16.

Scheme VII

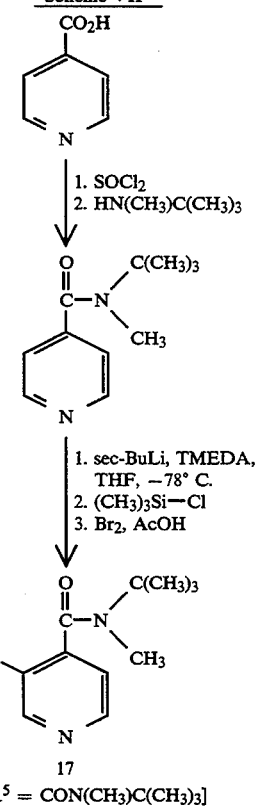

17
[R⁵ = CON(CH₃)C(CH₃)₃]

Synthetic Scheme VII shows the preparation of the 3-bromopyridine coupling reagent 17 [R⁵=CON(CH₃)C(CH₃)₃] from isonicotinic acid. In step 1, N-tertbutyl-N-methylisonicotinamide is prepared from isonicotinoyl chloride and N-tertbutyl-N-methylamine. In step 2, reaction with sec-butyllithium gives the ortho-lithiated species which is reacted with trimethylsilyl chloride; subsequent conversion to the corresponding bromide on treatment with bromine in acetic acid provides 17.

Scheme VIII

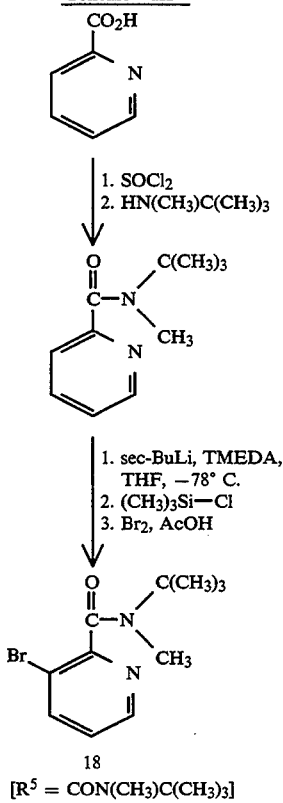

18
[R[5] = CON(CH$_3$)C(CH$_3$)$_3$]

118 C-2653

Synthetic Scheme VIII shows the preparation of the 3-bromopyridine coupling reagent 18 [R[5]=CON(CH$_3$)C(CH$_3$)$_3$] from picolinic acid. In step 1, N-tertbutyl-N-methylpicolinamide is prepared from picolinoyl chloride and N-tertbutyl-N-methylamine. In step 2, reaction with sec-butyllithium gives the ortho-lithiated species which is reacted with trimethylsilyl chloride; subsequent conversion to the corresponding bromide on treatment with bromine in acetic acid provides 18.

Scheme IX

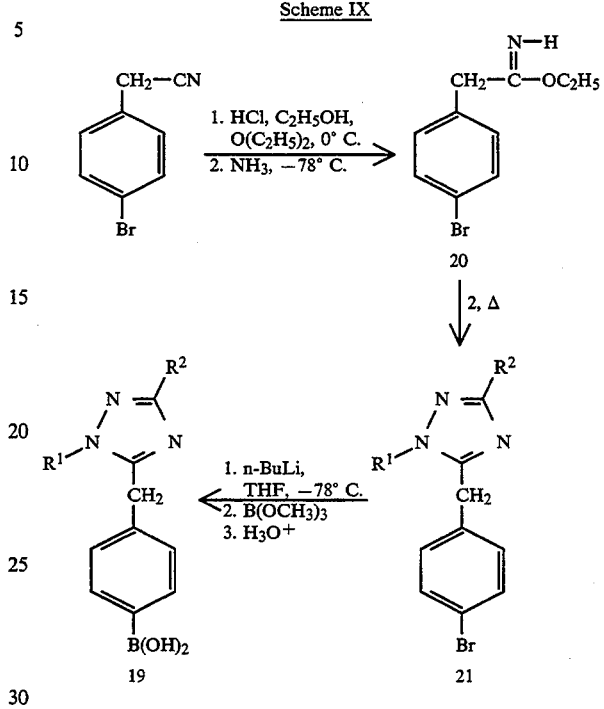

Synthetic Scheme IX shows the preparation of the triazole boronic acid coupling reagent 19 from 4-bromophenylacetonitrile (Aldrich). In step 1, reaction with hydrogen chloride and ethanol in ether at 0° C. produces the imidate ester hydrochloride which is subsequently converted to the free imidate ester 20 on treatment with ammonia at low temperatures. In step 2, the imidate ester 20 is reacted with the hydrazide 2 (Scheme III) to give the bromotriazole 21. In step 3, halogen-metal interchange with n-butyllithium generates the corresponding lithiated species which is reacted with trimethyl borate. The free triazole boronic acid coupling reagent 19 is produced on hydrolysis.

Scheme X

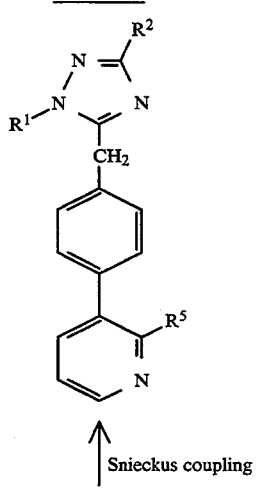

↑ Snieckus coupling

Scheme X

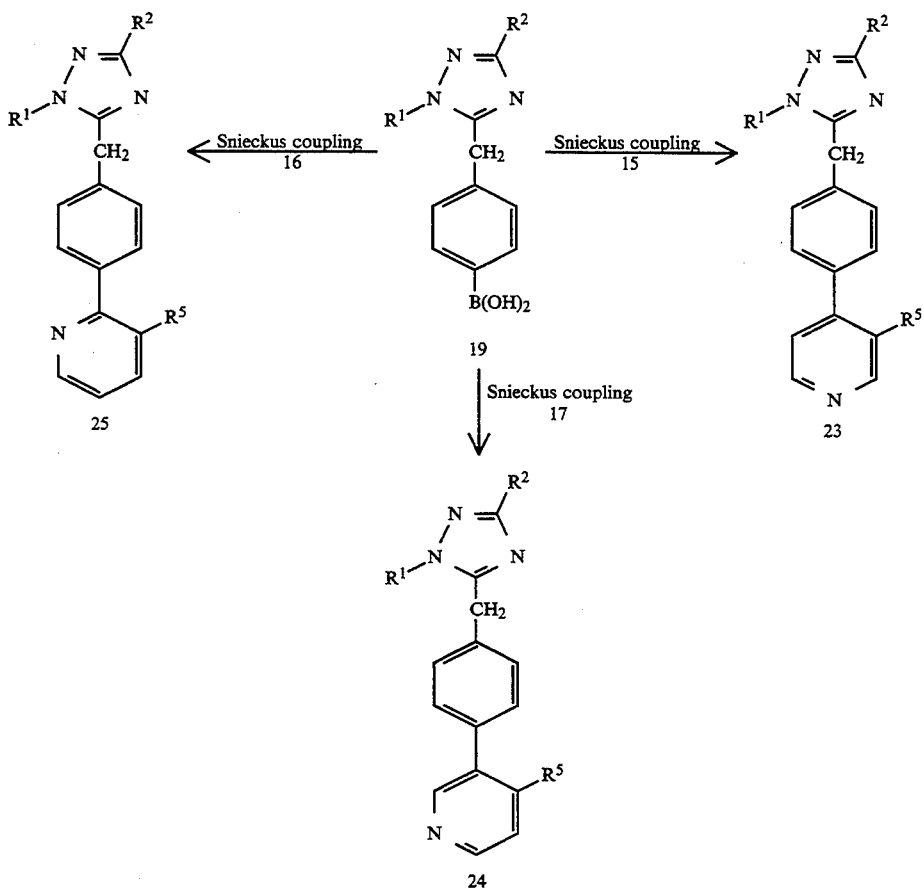

Synthetic Scheme X shows the preparation of 5-(pyridinylphenyl)methyl-1H-1,2,4-triazoles 22, 23, 24 and 25 from the common triazole boronic acid 19 (Scheme IX) and the corresponding bromo coupling reagents 18 (Scheme VIII), 15 (Scheme VI), 17 (Scheme VII), and 16 (Scheme VI), respectively. The boronic acid 19 is reacted with the bromo coupling reagents 18, 15, 17 and 18 in the presence of a palladium zero catalyst via a Snieckus coupling [see M. J. Sharp and V. Snieckus, *Tetrahedron Lett.*, 5997 (1985)] to give the angiotensin II antagonists 22, 23, 24, and 25, respectively, of this invention.

Scheme XI

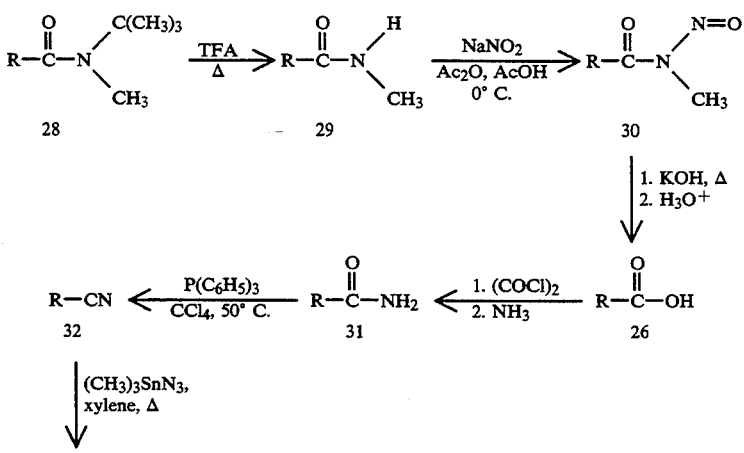

Scheme XI

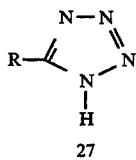

Synthetic Scheme XI shows the preparation of carboxylic acid analogs 26 and 1H-tetrazole analogs 27 from analogs which have $R^5$=CON(CH$_3$)C(CH$_3$)$_3$. In step 1, the N-tertbutyl-N-methylamide analog 28 is reacted with trifluoroacetic acid at reflux to give the N-methylamide 29. In step 2, the N-methylamide 29 is reacted with sodium nitrite in acetic anhydride/acetic acid at 0° C. to give the corresponding N-methyl-N-nitrosoamide 30. In step 3, the N-methyl-N-nitrosoamide 30 is hydrolyzed in base to give the corresponding carboxylic acid angiotensin II antagonists of this invention. In step 4, the acid analog 26 is reacted with oxalyl chloride and subsequently with anhydrous ammonia to give the primary amide 31. In step 5, the amide 31 is reacted with triphenylphosphine in carbon tetrachloride at 50° C. to give the corresponding nitrile 32. In step 6, the nitrile 32 is reacted with trimethyltin azide in xylene at reflux to provide the 1H-tetrazole angiotensin II antagonists of this invention.

The following Example is a detailed description of the methods of preparation of compounds of Formula I. This detailed preparation falls within the scope of, and serves to exemplify, the above described General Synthetic Procedures which form part of the invention. This Example is presented for illustrative purposes only and is not intended as a restriction on the scope of the invention. All parts are by weight unless otherwise indicated.

EXAMPLE 1

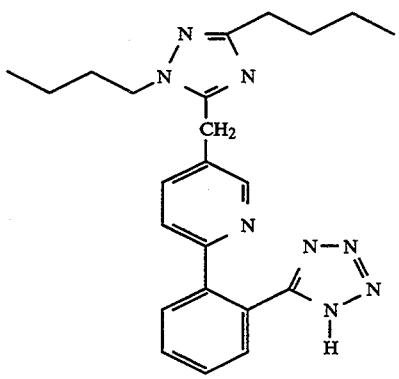

5-[2-[5-[(1,3-dibutyl-1H-1,2,4-triazol-5-yl)methyl]-2-pyridinyl]phenyl]-1H-tetrazole Step 1; Preparation of 2-(N-triphenylmethyltetrazol-5-yl)phenylboronic acid A 64 g (350 mmol) sample of 2-bromobenzonitrile (Aldrich) was dissolved in 650 mL of xylene and treated with 22.75 g (350 mmol) of sodium azide and 95 mL (350 mmol) of tributyltin chloride at reflux for 48 h. The reaction was filtered; the filtrate was treated with 50 mL of anhydrous tetrahydrofuran (THF) and 20 g (550 mmol) of hydrogen chloride. The reaction was stirred for 2 h; filtration gave 59.6 g (76%) of 5-(2-bromophenyl)-1H-tetrazole: mp 178°–180° C.; NMR (DMSO-d$_6$) δ7.50–7.64 (m, 2H), 7.67–7.74 (m, 1H), 7.83–7.91 (m, 1H). A 41.8 g (187 mmol) sample of this material was dissolved in 650 mL of methylene chloride and treated with 55.5 g (193 mmol) of triphenylmethyl chloride and 30 mL (220 mmol) of anhydrous triethylamine. The reaction was allowed to stir overnight at reflux, cooled to ambient temperature, washed with water, dried (MgSO$_4$), and concentrated in vacuo. Recrystallization from toluene/hexane gave 80.7 g (92%) of N-triphenylmethyl-5-(2-bromophenyl)-1H-tetrazole: mp 160°–162° C.; NMR (CDCl$_3$) δ 7.14–7.21 (m, 6H), 7.26–7.45 (m, 11H), 7.70 (dd, J=8 and 1.5 Hz, 1H), 7.89 (dd, J=7.5 and 2 Hz, 1H). A 34.05 g (73.0 mmol) sample of this material was dissolved in 1700 mL of THF under a nitrogen atmosphere and treated with 73 mmol of n-butyllithium in hexane. The reaction was allowed to stir for 17 min and then was treated with 24.9 mL (220 mmol) of trimethyl borate. The reaction was allowed to come to ambient temperature overnight while stirring, quenched with 10 mL of methanol, and concentrated in vacuo. The residue was dissolved in 1M NaOH and extracted with toluene to remove any unreacted starting material. The pH was adjusted to 6 with 6M HCl and the product extracted with toluene and dried (MgSO$_4$). Hexane was added and the solution kept in the freezer overnight. Filtration provided 31.3 g (99%) of 2-(N-triphenylmethyl-tetrazol-5-yl) phenylboronic acid: NMR (CDCl$_3$) δ7.13–7.21 (m, 7H), 7.33–7.42 (m, 8H), 7.49–7.55 (m, 2H), 8.15–8.19 (m, 1H), 8.21–8.26 (m, 1H).

Step 2: Preparation of N$^2$-butyl valeric acid hydrazide

To a solution of 400 g (3.44 mol) of valeric acid hydrazide (Lancaster Synthesis) in 3000 mL of dichloromethane under a nitrogen atmosphere, was added 250 g (2 mol) of anhydrous magnesium sulfate and 310 g (3.88 mol) of butyraldehyde. The reaction was stirred at ambient temperature for 17 h, filtered, and concentrated in vacuo providing 613 g of nearly colorless solid: mp 66.5°–68.0° C.; NMR (CDCl$_3$) δ 0.97 (t, J=7Hz, 3H), 0.92 (t, J=7Hz, 3H), 1.31–1.46 (m, 2H), 1.48–1.73 (m, 4H), 2.19–2.28 (m, 2H), 2.62 (t, J=7Hz, 2H), 7.14 (t, J=6Hz, 1H), 9.18 (br s, 1H). This material was dissolved in 3000 mL of ethanol and cooled to 0° C. in an ice bath prior to the addition of 130.1 g (3.44 mol) of sodium borohydride. The reaction was maintained at 0° C. for 3 h and then allowd to slowly warm to ambient temperature overnight. The volatiles were removed in vacuo and the residue dissolved in 1500 mL of water and conninuousiy extracted with ether/dichloromethane (1:1) overnight. The extracts were dried (Na$_2$SO$_4$) and concentrated in vacuo to give 549 g (93%) of colorless N$^2$-butyl valeric acid hydrazide: mp 66.0°–67.5° C.; NMR (CDCl$_3$) δ0.92 (t, J=7Hz, 6H), 1.17–1.52 (m, 6H), 1.56–1.69 (m, 2H), 2.14 (t, J=7Hz, 2H), 2.82 (t, J=7Hz, 2H).

Step 3; Preparation of 2-bromo-5-picoline

A solution of 1500 mL (14 mol) of 48% hydrobromic acid was cooled to 10° C. and 300 g (2.8 mol) of 2-amino-5-picoline (Aldrich) was added slowly. The solution was maintained at or below 0° C. while 450 mL (8.8 mol) of bromine was added dropwise. After the bromine addition was complete, a solution of 500 g (7.3 mol) of sodium nitrite in 1000 mL of water was added slowly over 6 h. The reaction pH was adjusted by the careful addition of 1500 mL (56 mol) of 50% sodium hydroxide at such a rate that the temperature was maintained below 30° C. The product precipitated from the nearly colorless reaction mixture; filtration gave 450 g (94%) of 2-bromo-5-picoline as a yellow powder: mp 38°-40° C.; NMR 7.27 (s, 1H), 7.28 (s, 1H), 7.12 (br s, 1H).

Step 4; Preparation of 2-bromo-5-romomethylpyridine

A solution of 296.3 g (1.72 mol) of 2-bromo-5picoline from step 3 in 6 L of carbon tetrachloride was treated with 306.5 g (1.72 tool) of N-bromosuccinimide (NBS) and 28.3 g 173 mmol) of azobisisobutyronitrile (AIBN). The reaction was stirred at reflux under nitrogen for 3 h, filtered, and concentrated in vacuo providing 476 g of crude 2-bromo-5-bromomethylpyridine as a brownish yellow solid (NMR indicates that this material is only 60% monobromomethyl product): NMR (CDCl$_3$) δ 4.42 (s, 2H), 7.48 (d, J=9Hz, 1H), 7.60 (dd, 2=9 and 3Hz, 1H), 8.37 (d, J=3Hz, 1H).

Step 5: Preparation of 2-bromo-5-cyanomethyl-pyridine.

The 476 g of crude 2-bromo-5-bromomethylpyridine from step 4 was dissolved in 4000 mL of dimethylformamide (DMF)/water (7:1) and treated with 168 g (2.58 mol) of potassium cyanide. The reaction was allowed to stir at ambient temperature for 72 h, concentrated in vacuo, and partitioned between ethyl acetate and water; the organic layer was washed with water, washed with brine, dried (MgSO$_4$), and reconcentrated in vacuo to provide the crude nitrile. Purification by silica gel chromatography (Waters Prep-500A) using ethyl acetate/hexane (25:75) gave 109 g (32% from 2-bromo-5-picoline) of 2-bromo-5-cyanomethylpyridine as a yellowish orange solid: mp 55.5°-57.5° C; NMR (CDCl$_3$) δ 3.74 (s, 2H), 7.54 (d, J=8Hz, 1H), 7.59 (dd, J=8 and 2 HZ, 1H), 8.35 (d, J=2Hz, 1H); MS (FAB) m/e (rel intensity) 199 (85), 197 (100).

Step 6: Preparation of ethyl imino(2-bromopyridin-5-yl)acetate

Under nitrogen, 299 mL (4.20 mol) of acetyl chloride was added dropwise to a solution of 299 mL (5.11 tool) of absolute ethanol and 400 mL of chloroform at 0° C. A solution of 72.0 g (370 mmol) of 2-bromo-5cyanomethylpyridine from step 5 in 1100 mL of chloroform was added dropwise with stirring. Stirring was continued at 0° C. for 4 h and the reaction was allowed to come to ambient temperature overnight. The reaction was diluted with 2500 mL of anhydrous ether and stirring was continued for an additional 2 h. The precipitated imidate hydrochloride salt was collected by filtration in a glove bag under nitrogen and washed with anhydrous ether. Under nitrogen, a mechanically stirred suspension of this material in 3500 mL of anhydrous ether at −78° C. was treated with 36 g (2.1 mol) of anhydrous ammonia. The reaction was allowed to slowly warm to ambient temperature overnight and the ammonium chloride removed by filtration. The filtrate was concentrated in vacuo giving 8.7 g (89%) of crude ethyl imino(2-bromopyridin-5-yl) acetate as a brown oil: NMR (CDCl$_3$) δ 1.29 (t, J=7Hz, H), 3.51 (s, 2H), 4.13 (q, J=7Hz, 2H), 7.43 (dd, J=8 and Hz, 1H), 7.48 (d, J=8Hz, 1H), 8.26 (d, J=2Hz, 1H); MS (FAB) m/e (rel intensity) 245 (100), 243 (90), 217 (35), 215 (38), 200 (5), 198 (5).

Step 7: preparation of 2-bromo-5-[(1,3-dibutyl-1H-1,2,4-triazol-5-yl) methyl]pyridine Under nitrogen, a solution of 1.2 g (5 mmol) of imidate ester from step 6 and 850 mg (5 mmol) of N$^2$-butyl valeric acid hydrazide from step 2 in 25 mL of absolute methanol was stirred for 24 h at ambient temperature. The methanol was removed in vacuo and replaced with 25 mL of anhydrous toluene. The reaction vessel was equipped with a Dean-Stark trap and the reaction stirred at reflux for 48 h. Concentration in vacuo produced the crude product residue. Purification by silica gel chromatography (Waters Prep-500A) using ethyl acetate/hexane (60:40) gave 700 mg (40%) of 2-bromo-5-[(1, 3-dibutyl-1H-1,2,4-triazol-5-yl)methyl]pyridine as an oil: NMR (CDCl$_3$) δ 0.88 (t, J=7Hz, 3H), 0.92 (t, J=7Hz, 3H), 1.25-1.75 (m, 8H), 2.67 (t, J=8Hz, 2H), 3.93 (t, J=7Hz, 2H), 4.05 (s, 2H), 7.43 (s, 1H), 7.44 (s, 1H), 8.27 (s, 1H); MS (FAB)m/e (rel intensity) 353 (50), 351 (50), 297 (100), 295 (100), 215 (40), 160 (90), 158 (90), 138 (70).

Step 8: Preparation of 5-[2-[5-[(1,3-dibutyl-1H-1,2,4-triazol-5-yl) methyl]-2-pyridinyl]phenyl-1H-tetrazole Under nitrogen, a solution of 700 mg (2.0 mmol) of 2-bromo-5-[(1,3-dibutyl-1H-1,2,4-triazol-5yl)methyl]-pyridine from seep 7 and 180 mg (0.16 mmol) of tetrahis (tri-phenylphosphine)palladium in 12 mL of toluene and 3 mL of 2M sodium carbonate was treated with a solution of 1.12 g (2.6 mmol) of 2-(N-triphenylmethyltetrazol-5-yl)phenylboronic acid from step 1 in 3 mL of ethanol. The reaction was vigorously stirred at reflux for 17 h. The reaction was cooled to ambient temperature and three immiscible phase separated; the middle phase contained the deprotected tetrazole product. Purification by reverse phase chromatography (Waters Deltaprep-3000) using isocratic acetonitrile/water (27: 73) (0.05% TFA) gave 300 mg (28%) of colorless 5-[2-[5-[(1,3-dibutyl-1H-1,2,4-triazol-5-yl ) methyl]-2-pyridinyl]phenyl-1H-tetrazole as the trifluoroacetic acid (TFA) salt after lyophilization: NMR (CDCl$_3$) δ 0.93 (t, J=7Hz, 6H), 1.26-1.46 (m, 4H), 1.67-1.89 (m, 4H), 2.74 (t, J=8Hz, 2H), 4.10 (t, J=7Hz, 2H), 4.30 (s, 2H), 7.43 (d, J=8Hz, 1H), 7.53-7.62 (m, 3H), 7.74 (dd, J=8 and 2 Hz, 1H), 8.02-8.05 (m, 1H), 8.52 (d, J=2Hz, 1H); MS (FAB) m/e (rel intensity) 417 (100), 389 (75), 361 (20); HRMS. Calc'd for M+H: 417.2515. Found: 417.2516.

BIOLOGICAL EVALUATION

Assay A: Angiotensin II Binding Activity

Compounds of the invention were tested for ability to bind to the smooth muscle angiotensin II receptor using a rat uterine membrane preparation. Angiotensin II (AII) was purchased from Peninsula Labs. $^{125}$I-angiotensin II (specific activity of 2200 Ci/mmol) was purchased from Du Pont-New England Nuclear. Other chemicals were obtained from Sigma Chemical Co.

This assay was carried out according to the method of Douglas et al [*Endocrinology*, 106, 120-124 (1980)]. Rat uterine membranes were prepared from fresh tissue. All procedures were carried out at 4° C. Uteri were stripped of fat and homogenized in phosphate-buffered saline at pH 7.4 containing 5 mM EDTA. The homogenate was centrifuged at 1500 × g for 20 min., and the supernatant was recentrifuged at 100,000 × g for 60 min. The pellet was resuspended in buffer consisting of 2 mM EDTA and 50 mM Tris-HCl (pH 7.5) to a final protein concentration of 4 mg/ml. Assay tubes were charged with 0.25 ml of a solution containing 5 mM $MgCl_2$, 2 mM EDTA, 0.5% bovine serum albumin, 50 mM Tris-HCl, pH 7.5 and $^{125}I$-AII (approximately $10^5$ cpm) in the absence or in the presence of unlabelled ligand. The reaction was initiated by the addition of membrane protein and the mixture was incubated at 25° C. for 60 min. The incubation was terminated with ice-cold 50 mM Tris-HCl (pH 7.5) and the mixture was filtered to separate membrane-bound labelled peptide from the free ligand. The incubation tube and filter were washed with ice-cold buffer. Filters were assayed for radioactivity in a Micromedic gamma counter. Nonspecific binding was defined as binding in the presence of 10 μM of unlabelled AII. Specific binding was calculated as total binding minus nonspecific binding. The receptor binding affinity of an AII antagonist compound was indicated by the concentration ($IC_{50}$) of the tested AII antagonist which gives 50% displacement of the total specifically bound $^{125}I$-AII from the high affinity AII receptor. Binding data were analyzed by a nonlinear least-squares curve fitting program. Results are reported in Table I.

Assay B: In Vitro Vascular Smooth Muscle-Response for AII

The compounds of the invention were tested for antagonist activity in rabbit aortic rings. Male New Zealand white rabbits (2-2.5 kg) were sacrificed using an overdose of pentobarbital and exsanguinated via the carotid arteries. The thoracic aorta was removed, cleaned of adherent fat and connective tissue and then cut into 3-mm ring segments. The endothelium was removed from the rings by gently sliding a rolled-up piece of filter paper into the vessel lumen. The rings were then mounted in a water-jacketed tissue bath, maintained at 37° C. between moveable and fixed ends of a stainless steel wire with the moveable end attached to an FT03 Grass transducer coupled to a Model 7D Grass Polygraph for recording isometric force responses. The bath was filled with 20 ml of oxygenated (95% oxygen/5% carbon dioxide) Krebs solution of the following composition (mM): 130 NaCl, 15 $NaHCO_3$, 15 KCl, 1.2 $NaH_2PO_4$, 1.2 $MgSO_4$, 2.5 $CaCl_2$, and 11.4 glucose. The preparations were equilibrated for one hour before approximately one gram of passive tension was placed on the rings. Angiotensin II concentration-response curves were then recorded ($3\times10^{-10}$ to $1\times10^{-5}M$). Each concentration of AII was allowed to elicit its maximal contraction, and then AII was washed out repeatedly for 30 minutes before rechallenging with a higher concentration of AII. Aorta rings were exposed to the test antagonist at $10^{-5}M$ for 5 minutes before challenging with AII. Adjacent segments of the same aorta ring were used for all concentration-response curves in the presence or absence of the test antagonist. The effectiveness of the test compound was expressed in terms of $pA_2$ values and were calculated according to H. O. Schild [*Br. J. Pharmacol. Chemother.*, 2,189-206 (1947)]. The $pA_2$ value is the concentration of the antagonist which increases the EC50 value for AII by a factor of two. Each test antagonist was evaluated in aorta rings from two rabbits. Results are reported in Table I.

TABLE I

| | In Vitro Angiotensin II Activity of Compounds of the Invention | |
|---|---|---|
| Test Compound Example # | [1]Assay A $IC_{50}$ (nM) | [2]Assay B $pA_2$ |
| 1 | 31 | 7.80/7.91 |

[1]Assay A: Angiotensin II Binding Activity
[2]Assay B: In Vitro Vascular Smooth Muscle Response Also embraced within this invention is a class of pharmaceutical compositions comprising one or more compounds of Formula I in association with one or more nontoxic, pharmaceutically acceptable carriers and/or diluents and/or adjuvants (collectively referred to herein as "carrier" materials) and, if desired, other active ingredients. The compounds of the present invention may be administered by any suitable route, preferably in the form of a pharmaceutical composition adapted to such a route, and in a dose effective for the treatment intended. Therapeutically effective doses of the compounds of the present invention required to prevent or arrest the progress of the medical condition are readily ascertained by one of ordinary skill in the art. The compounds and composition may, for example, be administered intravascularly, intraperitoneally, subcutaneously, intramuscularly or topically.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. These may with advantage contain an amount of active ingredient from about 1 to 250 mg, preferably from about 25 to 150 mg. A suitable daily dose for a mammal may vary widely depending on the condition of the patient and other factors. However, a dose of from about 0.1 to 3000 mg/kg body weight, particularly from about 1 to 100 mg/kg body weight, may be appropriate.

The active ingredient may also be administered by injection as a composition wherein, for example, saline, dextrose or water may be used as a suitable carrier. A suitable daily dose is from about 0.1 to 100 mg/kg body weight injected per day in multiple doses depending on the disease being treated. A preferred daily dose would be from about 1 to 30 mg/kg body weight. Compounds indicated for prophylactic therapy will preferably be administered in a daily dose generally in a range from about 0.1 mg to about 100 mg per kilogram of body weight per day. A more preferred dosage will be a range from about 1 mg to about 100 mg per kilogram of body weight. Most preferred is a dosage in a range from about 1 to about 50 mg per kilogram of body weight per day. A suitable dose can be administered, in multiple sub-doses per day. These subdoses may be administered in unit dosage forms. Typically, a dose or sub-dose may contain from about 1 mg to about 100 mg of active compound per unit dosage form. A more preferred dosage will contain from about 2 mg to about 50 mg of active compound per unit dosage form. Most preferred is a dosage form containing from about 3 mg to about 25 mg of active compound per unit dose.

The dosage regimen for treating a disease condition with the compounds and/or compositions of this invention is selected in accordance with a variety of factors, including the type, age, weight, sex and medical condition of the patient, the severity of the disease, the route of administration, and the particular compound employed, and thus may vary widely.

For therapeutic purposes, the compounds of this invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethy cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Although this invention has been described with respect to specific embodiments, the details of these embodiments are not to be construed as limitations.

What is claimed is:

1. A therapeutic method for treating a circulatory disorder, said method comprising administering to a subject susceptible to or afflicted with such disorder a therapeutically-effective amount of a compound of Formula I

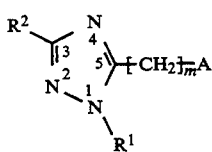

(I)

wherein A is selected from

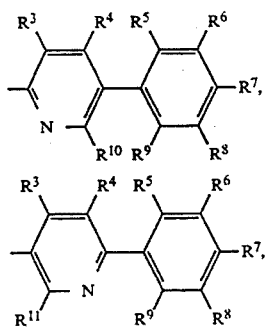

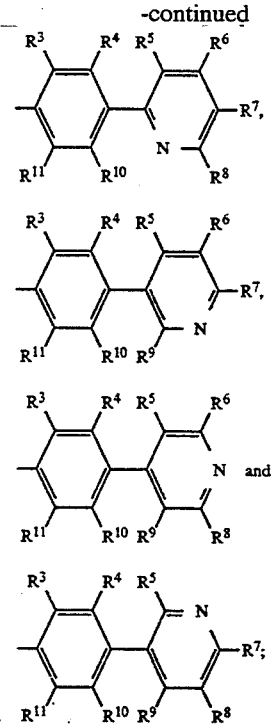

wherein m is a number selected from one to four, inclusive;

wherein $R^1$ is selected from hydrido, alkyl, hydroxyalkyl, haloalkyl, cycloalkyl, cycloalkylalkyl, formyl, aralkyl, aryl, aroyt, alkoxyalkyl, alkylcarbonyl, alkylcarbonylalkyl, alkoxycarbonyl, alkenyl, cycloalkenyl, aralkoxycarbonyl, alkynyl, alkylthiocarbonyl, alkylthiothiocarbonyl, arylthiocarbonyl, arylthiothiocarbonyl, aralkylthiocarbonyl, alkylthiocarbonyl, alkylsulfinyl, alkylsulfonyl, aralkylsulfinyl, aralkylsulfonyl, arylsulfinyl, arylsulfonyl, and amido radicals of the formula

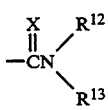

wherein X is oxygen atom or sulfur atom; wherein each of $R^{12}$ and $R^{13}$ is independently selected from hydrido, alkyl, cycloalkyl, cyano, amino, monoalkylamino, dialkylamino, hydroxyalkyl, cycloalkylalkyl, alkoxyalkyl, aralkyl and aryl or tetrazole; wherein each of $R^2$ through $R^{11}$ is independently selected from hydrido, alkyl, hydroxyalkyl, halo, haloalkyl, cycloalkyl, cycloalkylalkyl, cycloalkylhaloaklyl, cycloalkylcarbonyl, formyl, alkoxy, aralkyl, aralkylhaloalkyl, aryl, aroyl, aryloxy, aryloxyalkyl, aralkoxy, alkoxyalkyl, alkylcarbonyl, alkylcarbonylalkyl, alkoxycarbonyl, alkenyl, cycloalkenyl, alkynyl, cyano, nitro, carboxyl carboxyalkyl, alkylcarbonyloxy, alkylcarbonyloxyalkyl, alkoxycarbonylalkyl, aralkoxycarbonylalkyl, aralkylcarbonyloxyalkyl, mercaptocarbonyl, mercaptothiocarbonyl, mercaptoalkyl, alkoxycarbonyloxy, alkylthio, cycloalkylthio, cycloalkylalkylthio, alkylthiocarbonyl, alkylcarbonylthio, alkylthiocarbonyloxy, alkylthiocarbonylthio, alkylthiothiocarbonyl, alkylthiothiocarbonylthio, arylthio, arylthiocarbonyl, arylcarbonylthio, arylthiocarbonyloxy, arylthiocarbonylthio, arylthiothiocarbonyl, arylthiothiocarbonylthio, aralkylthio, aralkylthiocarbonyl, aralkylthiocarbonyl, aralkylthiocarbonyloxy, aralkylthiocarbonylthio, alkylthiocarbonyl, aralkylthiocarbonylthio, mercapto, alkylsulfinyl, alkylsulfonyl, aralkylsulfinyl, aralkylsulfonyl, arylsulfinyl, arylsulfonyl, phthalimido, phthalimidoalkyl, and wherein each of $R^2$ through $R^{11}$ may be further independently selected from amino and amido radicals of the formula

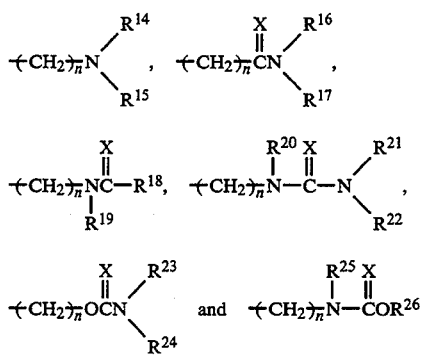

wherein X is oxygen atom or sulfur atom;
wherein each n is a number independently selected from zero to six, inclusive;
wherein each of $R^{14}$ through $R^{26}$ is independently selected from hydrido, alkyl, cycloalkyl, cyano, amino, monoalkylamino, dialkylamino, hydroxyalkyl, cycloalkylalkyl, alkoxyalkyl, aralkyl and aryl,
and wherein each of $R^3$ through $R^{11}$ may be further independently selected from hydroxy and acidic moieties of the formula $$-Y_nA$$

wherein n is a number selected from zero through three, inclusive, and wherein A is an acidic group selected to contain at least one acidic hydrogen atom, and the amide, ester and salt derivatives of said acidic moieties; wherein Y is a spacer group independently selected from one or more of alkyl, cycloalkyl, cycloalkylalkyl, alkenyl, alkynyl, aryl, aralkyl and heteroaryl having one or more ring atoms selected from oxygen, sulfur and nitrogen atoms;
and wherein any of the foregoing $R^1$ through $R^{26}$, Y and A groups having a substitutable position may be substituted by one or more groups independently selected from hydroxy, alkyl, alkenyl, alkynyl, aralkyl, hydroxyalkyl, haloalkyl, halo, oxo, alkoxy, aryloxy, aralkoxy, aralkylthio, alkoxyalkyl, cycloalkyl, cycloalkylalkyl, aryl, aroyl, cycloalkenyl, cyano, cyanoamino, nitro, alkylcarbonyloxy, alkoxycarbonyloxy, alkylcarbonyl, alkoxycarbonyl, aralkoxycarbonyl, carboxyl, mercapto, mercaptocarbonyl, alkylthio, arylthio, alkylthiocarbonyl, alkylsulfinyl, alkylsulfonyl, haloalkylsulfonyl, aralkylsulfinyl, aralkylsulfonyl, arylsulfinyl, arylsulfonyl, amino and amido radicals of the formula

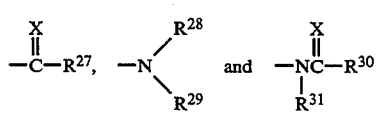

wherein X is oxygen atom or sulfur atom; wherein each of $R^{27}$ through $R^{3i}$ is independently selected from hydrido, alkyl, cycloalkyl, cycloalkylalkyl, aralkyl, aryl, $DR^{32}$ and

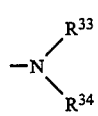

wherein D is selected from oxygen atom and sulfur atom and $R^{32}$ is selected from hydrido, alkyl, cycloalkyl, cycloalkylalkyl, aralkyl and aryl; wherein each of $R^{27}$, $R^{28}$, $R^{29}$, $R^{30}$, $R^{31}$, $R^{33}$ and $R^{34}$ is independently selected from hydrido, alkyl, cycloalkyl, cyano, hydroxyalkyl, haloalkyl, cycloalkylalkyl, alkoxyalkyl, alkylcarbonyl, alkoxycarbonyl, carboxyl, alkylsulfinyl, alkylsulfonyl, arylsulfinyl, arylsulfonyl, haloalkylsulfinyl, haloalkylsulfonyl, aralkyl and aryl, and wherein each of $R^{27}$, $R^{28}$, $R^{29}$, $R^{30}$, $R^{31}$, $R^{33}$ and $R^{34}$ is further independently selected from amino and amido radicals of the formula

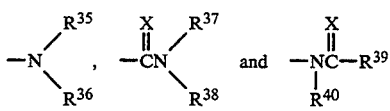

wherein X is oxygen atom or sulfur atom; wherein each of $R^{35}$, $R^{36}$, $R^{37}$, $R^{38}$, $R^{39}$ and $R^{40}$ is independently selected from hydrido, alkyl, cycloalkyl, cyano, hydroxyalkyl, cycloalkylalkyl, alkoxyalkyl, haloalkylsulfinyl, haloalkylsulfonyl, aralkyl and aryl.

2. The method of claim 1 wherein m is one; wherein $R^1$ is selected from hydrido, alkyl, hydroxyalkyl, haloalkyl, cycloalkyl, cycloalkylalkyl, aralkyl, aryl, aroyl, alkoxyalkyl, alkylcarbonyl, alkoxycarbonyl, alkenyl, cycloalkenyl, alkynyl, cycloalkynyl, carboxyl, alkylthiocarbonyl, arylthiocarbonyl, arylthiothiocarbonyl, aralkylthiocarbonyl, alkylsulfonyl, aralkylsulfonyl, arylsulfonyl, and amido radicals of the formula

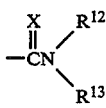

wherein X is oxygen atom or sulfur atom; wherein each of $R^{12}$ and $R^{13}$ is independently selected from hydrido, alkyl, cycloalkyl, cyano, amino, monoalkylamino, dialkylamino, hydroxyalkyl, cycloalkylalkyl, alkoxyalkyl, aralkyl and aryl;
wherein $R^2$ is selected from hydrido, alkyl, hydroxyalkyl, halo, haloalkyl, cycloalkyl, cycloalkylalkyl, cycloalkylhaloalkyl, cycloalkylcarbonyl, alkoxy, aralkyl, aralkylhaloalkyl, aryl, aroyl, aryloxy, aryloxyalkyl, aralkoxy, alkoxyalkyl, alkylcarbonyl, alkoxycarbonyl, alkenyl, cycloalkenyl, alkynyl, cycloalkynyl, cyano, nitro, carboxyl, carboxyalkyl, alkylcarbonyloxy, alkylcarbonyloxyalkyl, alkoxycarbonylalkyl, aralkoxycarbonylalkyl, aralkylcarbonyloxyalkyl, mercaptocarbonyl, mercaptothiocarbonyl, mercaptoalkyl, alkoxycarbonyloxy, alkylthio, cycloalkylthio, cycloalkylalkylthio, alkylthiocarbonyl, alkylcarbonylthio, alkylthiocarbonyloxy, alkylthiocarbonylthio, alkylthiothiocarbonyl, alkylthiothiocarbonylthio, arylthio, arylthiocarbonyl, arylcarbonylthio, arylthiocarbonyloxy, arylthiocarbonylthio, arylthiothiocarbonyl, arylthiothiocarbonylthio, aralkylthio, aralkylthiocarbonyl, aralkylcarbonylthio, aralkylthiocarbonyloxy, aralkylthiocarbonylthio, aralkylthiocarbonyl, aralkylthiocarbonylthio, mercapto, alkylsulfinyl, alkylsulfonyl, aralkylsulfinyl, aralkylsulfonyl, arylsulfinyl, arylsulfonyl, phthalimido, phthalimidoalkyl, and nitrogen atoms, and wherein each of $R^2$ through $R^{11}$ may be further independently selected from amino and amido radicals of the formula

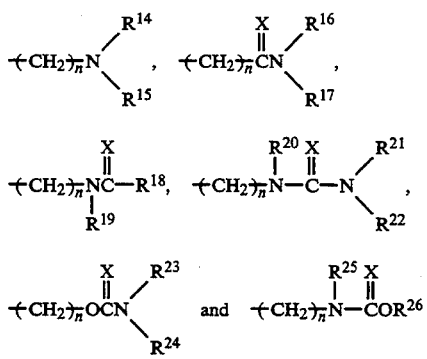

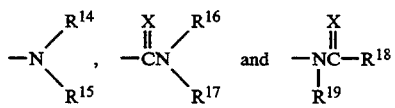

wherein X is selected from oxygen atom or sulfur atom; wherein each n is a number independently selected from zero to six, inclusive;

wherein each of $R^{14}$ through $R^{26}$ is independently selected from hydrido, alkyl, cycloalkyl, cyano, amino, monoalkylamino, dialkylamino, hydroxyalkyl, cycloalkylalkyl, alkoxyalkyl, aralkyl and aryl;

wherein each of $R^3$ through $R^{11}$ is independently selected from hydrido, hydroxy, alkyl, hydroxyalkyl, halo, haloalkyl, cycloalkyl, cycloalkylalkyl, alkoxy, aralkyl, aryl, aroyl, aryloxy, aralkoxy, alkoxyalkyl, alkylcarbonyl, alkoxycarbonyl, alkenyl, cycloalkenyl, alkynyl, cycloalkynyl, cyano, nitro, carboxyl, alkylcarbonyloxy, mercaptocarbonyl, mercaptothiocarbonyl, alkoxycarbonyloxy, alkylthio, alkylthiocarbonyl, alkylcarbonylthio, alkylthiocarbonyloxy, alkylthiocarbonylthio, alkylthiothiocarbonyl, arylthio, arylthiocarbonyl, arylcarbonylthio, arylthiocarbonyloxy, arylthiothiocarbonyl, aralkylthio, aralkylthiocarbonyl, aralkylcarbonylthio, aralkylthiocarbonyloxy, aralkylthiocarbonylthio, aralkylthiocarbonyl, aralkylthiocarbonylthio, mercapto, alkylsulfonyl, aralkylsulfonyl and arylsulfonyl, and amino and amido radicals of the formula

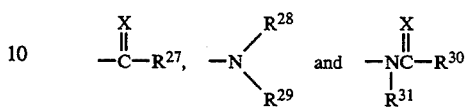

wherein X is oxygen atom or sulfur atom; wherein each of $R^{14}$, $R^{15}$, $R^{16}$, $R^{17}$, $R^{18}$ and $R^{19}$ is independently selected from hydrido, alkyl, cycloalkyl, cyano, hydroxyalkyl, cycloalkylalkyl, alkoxyalkyl, aralkyl and aryl;

and wherein each of $R^3$ through $R^{11}$ may be further independently selected from acidic moieties of the formula $$-Y_nA$$

wherein n is a number selected from zero through three, inclusive; wherein A is an acidic group selected from acids containing one or more atoms selected from oxygen, sulfur, phosphorus and nitrogen atoms, and wherein said acidic group is selected to contain at least one acidic hydrogen atom, and the amide, ester and salt derivatives of said acidic moieties; wherein Y is a spacer group independently selected from one or more of alkyl, cycloalkyl, cycloalkylalkyl, alkenyl, alkynyl, aryl, aralkyl and tetrazole;

and wherein any of the foregoing $R^1$ through $R^{26}$, Y and A groups having a substitutable position may be substituted by one or more groups independently selected from hydroxy, alkyl, alkenyl, aralkyl, hydroxyalkyl, halo, haloalkyl, oxo, alkoxy, aryloxy, aralkoxy, alkoxyalkyl, alkylcarbonyl, alkoxycarbonyl, carboxyl, cyano, nitro, alkylsulfonyl, haloalkylsulfonyl, aryl, aralkyl, mercaptocarbonyl, alkylthio and alkylthiocarbonyl, and amino and amido radicals of the formula

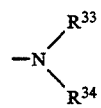

wherein X is oxygen atom or sulfur atom; wherein each of $R^{27}$ through $R^{31}$ is independently selected from hydrido, alkyl, cycloalkyl, cycloalkylalkyl, aralkyl, aryl, and $DR^{32}$ and $$-N\begin{matrix}R^{33}\\R^{34}\end{matrix}$$

wherein D is selected from oxygen atom and sulfur atom, and $R^{32}$ is selected from hydrido, alkyl, cycloalkyl, cycloalkylalkyl, aralkyl and aryl; wherein each of $R^{27}$, $R^{28}$, $R^{29}$, $R^{30}$, $R^{31}$, $R^{33}$ and $R^{34}$ is independently selected from hydrido, alkyl, cycloalkyl, cyano, hydroxyalkyl, haloalkyl, cycloalkylalkyl, alkoxyalkyl, alkanoyl, alkoxycarbonyl, carboxyl, haloalkylsulfinyl, haloalkylsulfonyl, aralkyl and aryl;

or a tautomer thereof or a pharmaceutically-acceptable salt thereof.

3. The method of claim 2 wherein m is one; wherein $R^1$ is selected from alkyl, hydroxyalkyl, haloalkyl, cycloalkyl, cycloalkylalkyl, aralkyl, aryl, aroyl, alkoxyalkyl, alkylcarbonyl, alkoxycarbonyl, alkenyl, cycloalkenyl, alkynyl, cycloalkynyl, carboxyl, alkylsulfonyl, aralkylsulfonyl and arylsulfonyl, and amido radicals of the formula

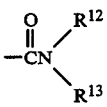

wherein each of $R^{12}$ and $R^{13}$ is independently selected from hydrido, alkyl, cycloalkyl, cyano, amino, monoalkylamino, dialkylamino, hydroxyalkyl, cycloalkylalkyl, alkoxyalkyl, aralkyl and aryl;

wherein $R^2$ is selected from hydrido, alkyl, hydroxyalkyl, halo, haloalkyl, cycloalkyl, cycloalkylalkyl, cycloalkylhaloalkyl, cycloalkylcarbonyl, alkoxy, aralkyl, aralkylhaloalkyl, aryl, aroyl, aryloxy, aryloxyalkyl, aralkoxy, alkoxyalkyl, alkylcarbonyl, alkoxycarbonyl, alkenyl, cycloalkenyl, alkynyl, cycloalkynyl, cyano, nitro, carboxyl, carboxyalkyl, alkylcarbonyloxy, mercaptocarbonyl, alkoxycarbonyloxy, alkylcarbonyloxyalkyl, alkoxycarbonylalkyl, aralkoxycarbonylalkyl, aralkylcarbonyloxyalkyl, alkylthio, cycloalkylthio, cycloalkylalkylthio, arylthio, aralkylthio, aralkylthiocarbonylthio, mercapto, alkylsulfinyl, alkylsulfonyl, aralkylsulfinyl, aralkylsulfonyl, arylsulfinyl, arylsulfonyl, phthalimido, phthalimidoalkyl, and wherein $R^2$ may be further selected from amino and amido radicals of the formula

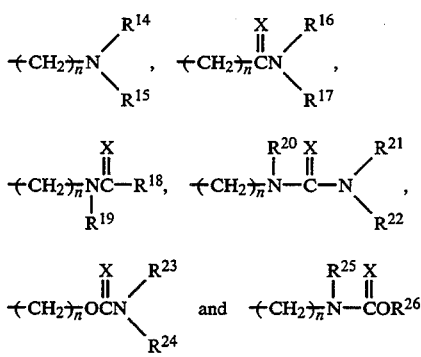

wherein X is selected from oxygen atom or sulfur atom; wherein each n is a number independently selected from zero to six, inclusive;
wherein each of $R^{14}$ through $R^{26}$ is independently selected from hydride, alkyl, cycloalkyl, cyano, amine, monoalkylamino, dialkylamino, hydroxyalkyl, cycloalkylalkyl, alkoxyalkyl, aralkyl and aryl;
wherein each of $R^3$ through $R^{11}$ is independently selected from hydride, hydroxy, alkyl, hydroxyalkyl, halo, haloalkyl, cycloalkyl, alkoxy, aralkyl, aryl, aroyl, aryloxy, aralkoxy, alkoxyalkyl, alkylcarbonyl, alkoxycarbonyl, alkenyl, cycloalkenyl, alkynyl, cyano, nitro, carboxyl, alkylcarbonyloxy, mercaptocarbonyl, alkoxycarbonyloxy, alkylthio, arylthio, aralkylthio, mercapto, alkylsulfonyl, aralkylsulfonyl and arylsulfonyl, and amine and amido radicals of the formula

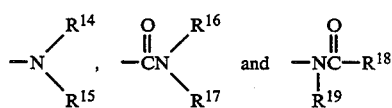

wherein each of $R^{14}$, $R^{15}$, $R^{16}$, $R^{17}$, $R^{18}$ and $R^{19}$ is independently selected from hydride, alkyl, cycloalkyl, cyano, amino, monoalkylamino, dialkylamino, hydroxyalkyl, cycloalkylalkyl, alkoxyalkyl, aralkyl and aryl;
and wherein each of $R^3$ through $R^{11}$ may be further independently selected from acidic moieties of the formula $$-Y_nA$$

wherein n is a number selected from zero through three, inclusive;
wherein the A group is selected to have an acidic proton, such that when the $-Y_nA$ moiety is incorporated within a compound of Formula I, there is provided a compound of Formula I having a $pK_a$ in a range from about two to about seven, said A group selected from carboxylic acid and bioisosteres of carboxylic acid selected from

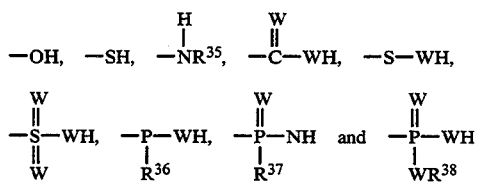

wherein each W is independently selected from oxygen atom, sulfur atom and $NR^{39}$; wherein each of $R^{35}$, $R^{36}$, $R^{37}$, $R^{38}$ and $R^{39}$ is independently selected from hydrido, alkyl, haloalkyl, haloalkylsulfonyl, haloalkylcarbonyl, cycloalkyl, cycloalkylalkyl, aryl and aralkyl; wherein each of $R^{35}$, $R^{36}$, $R^{37}$ and $R^{39}$ may be further independently selected from amino radical of the formula

wherein each of $R^{40}$ and $R^{41}$ is independently selected from hydrido, alkyl, cycloalkyl, hydroxyalkyl, haloalkyl, cycloalkylalkyl, alkoxyalkyl, aralkyl and aryl, and wherein Y is a spacer group independently selected from one or more of alkyl, cycloalkyl, cycloalkylalkyl, alkenyl, aryl and aralkyl;
and wherein any of the foregoing $R^1$ through $R^{26}$ and $R^{35}$ through $R^{41}$, Y and A groups having a substitutable position may be substituted by one or more groups independently selected from hydroxy, alkyl, alkenyl, aralkyl, hydroxyalkyl, halo, oxo, haloalkyl, alkoxy, aryloxy, aralkoxy, alkoxyalkyl, alkylcarbonyl, alkoxycarbonyl, carboxyl, cyano, nitro, alkylsulfonyl, haloalkylsulfonyl, aryl, aralkyl, mercaptocarbonyl, alkylthio and alkylthiocarbonyl, and amino and amido radicals of the formula

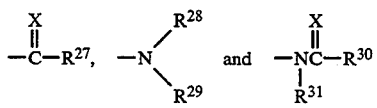

wherein X is selected from oxygen atom and sulfur atom; wherein $R^{27}$ is selected from hydrido, alkyl, cycloalkyl, cycloalkylalkyl, aralkyl, aryl and $DR^{32}$ and

wherein D is selected from oxygen atom and sulfur atom; wherein $R^{32}$ is selected from hydrido, alkyl, cycloalkyl, cycloalkylalkyl, aralkyl and aryl;
wherein each of $R^{27}$, $R^{28}$, $R^{29}$, $R^{30}$, $R^{31}$, $R^{33}$ and $R^{34}$ is independently selected from hydrido, alkyl, cycloalkyl, cyano, hydroxyalkyl, haloalkyl, cycloalkylalkyl, alkoxyalkyl, alkanoyl, alkoxycarbonyl, carboxyl, haloalkylsulfinyl, haloalkylsulfonyl, aralkyl and aryl;
or a tautomer thereof or a pharmaceutically-acceptable salt thereof.

4. The method of claim 3 wherein m is one; wherein $R^1$ is selected from hydrido, alkyl, hydroxyalkyl, haloalkyl, cycloalkyl, cycloalkylalkyl, aralkyl, aryl, aroyl, alkoxyalkyl, alkylcarbonyl, alkenyl, cycloalkenyl, alkynyl, mercaptocarbonyl, alkylsulfonyl, aralkylsulfonyl, arylsulfonyl and amido radicals of the formula

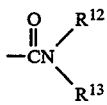

wherein each of $R^{12}$ and $R^{13}$ is independently selected from hydrido, alkyl, cycloalkyl, cyano, amino, monoalkylamino, dialkylamino, hydroxyalkyl, cycloalkylalkyl, alkoxyalkyl, aralkyl and aryl tetrazole;

wherein $R^2$ is selected from hydrido, alkyl, hydroxyalkyl, halo, haloalkyl, cycloalkyl, cycloalkylalkyl, cycloalkylhaloalkyl, cycloatkylcarbonyl, alkoxy, aralkyl, aralkylhaloalkyl, aryl, aroyl, aryloxy, aryloxyalkyl, aralkoxy, alkoxyalkyl, alkylcarbonyl, alkoxycarbonyl, alkenyl, cycloalkenyl, alkynyl, cycloalkynyl, cyano, nitro, carboxyl, carboxyalkyl, alkylcarbonyloxy, alkylcarbonyloxyalkyl, alkoxycarbonylalkyl, aralkoxycarbonylalkyl, aralkylcarbonyloxyalkyl, mercaptocarbonyl, mercaptoalkyl, alkoxycarbonyioxy, alkylthio, cycloalkylthio, cycloalkylalkylthio, arylthio, aralkylthio, mercapto, alkylsulfinyl, alkylsulfonyl, aralkylsulfinyl, aralkylsulfonyl, arylsulfinyl, arylsulfonyl, phthalimido, phthalimidoalkyl, and wherein each of $R^2$ through $R^{11}$ may be further independently selected from amino and amido radicals of the formula

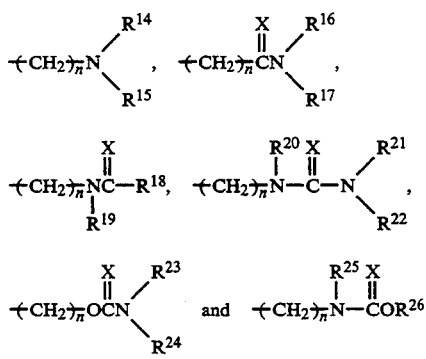

wherein X is selected from oxygen atom and sulfur atom;

wherein each n is a number independently selected from zero to six, inclusive;

wherein each of $R^{14}$ through $R^{26}$ is independently selected from hydrido, alkyl, cycloalkyl, cyano, amino, monoalkylamino, dialkylamino, hydroxyalkyl, cycloalkylalkyl, alkoxyalkyl, aralkyl and aryl;

wherein each of $R^3$ through $R^{11}$ is independently selected from hydrido, hydroxy, alkyl, hydroxyalkyl, halo, haloalkyl, cycloalkyl, alkoxy, aralkyl, aryl, aroyl, aryloxy, aralkoxy, alkoxyalkyl, alkylcarbonyl, alkoxycarbonyl, alkenyl, cycloalkenyl, alkynyl, cyano, nitro, carboxyl, alkylthio, aralkylthio and mercapto;

and wherein each of $R^3$ through $R^{11}$ may be further independently selected from acidic moieties of the formula

wherein n is a number selected from zero through three, inclusive; wherein A is selected from carboxylic acid and bioisosteres of carboxylic acid selected from

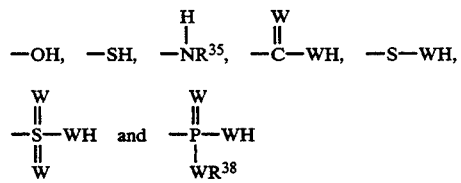

wherein each W is independently selected from oxygen atom, sulfur atom and $NR^{39}$; wherein each of $R^{35}$, $R^{38}$ and $R^{39}$ is independently selected from hydrido, alkyl, haloalkyl, haloalkylsulfonyl, haloalkylcarbonyl, cycloalkyl, cycloalkylalkyl, aryl and aralkyl; wherein each of $R^{35}$ and $R^{39}$ may be further independently selected from amino radical of the formula

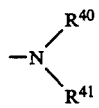

wherein each of $R^{40}$ and $R^{41}$ is independently selected from hydrido, alkyl, cycloalkyl, hydroxyalkyl, haloalkyl, cycloalkylalkyl, alkoxyalkyl, aralkyl and aryl, and wherein Y is a spacer group independently selected from one or aralkyl;

wherein each of $R^1$ through $R^{26}$, $R^{35}$ and $R^{38}$ through $R^{41}$, Y and A independently may be substituted at any substitutable position with one or more groups selected from alkyl, hydroxy, halo, oxo, haloalkyl, alkoxycarbonyl, cyano, nitro, alkylsulfonyl, haloalkylsulfonyl, aryl, aralkyl, alkoxy, aryloxy and aralkoxy;

or a tautomer thereof or a pharmaceutically-acceptable salt thereof.

5. The method of claim 4 wherein m is one; wherein $R^1$ is selected from hydrido, alkyl, hydroxyalkyl, haloalkyl, cycloalkyl, cycloalkylalkyl, aralkyl, aryl, aroyl, alkoxyalkyl, alkylcarbonyl, alkenyl, alkynyl, alkylsulfonyl, aralkylsulfonyl, arylsulfonyl and amido radicals of the formula

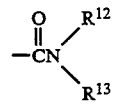

wherein each of $R^{12}$ and $R^{13}$ is independently selected from hydrido, alkyl, cycloalkyl, cyano, amino, hydroxyalkyl, alkoxyalkyl, phenalkyl and phenyl;

wherein $R^2$ is selected from hydrido, alkyl, hydroxyalkyl, halo, haloalkyl, cycloalkyl, cycloalkylalkyl, cycloalkylhaloalkyl, cycloalkylcarbonyl, alkoxy, aralkyl, aralkylhaloalkyl, aryl, benzoyl, phenoxy, phenoxyalkyl, phenalkyloxy, phenylthio, phenalkylthio, aralkoxy, alkoxyalkyl, alkylcarbonyl, alkoxycarbonyl, alkenyl, cycloalkenyl, alkynyl, cyano, nitro, carboxyl, carboxyalkyl, alkylcarbonyloxy, alkylcarbonyloxyalkyl, alkoxycarbonylalkyl, aralkoxycarbonylalkyl, aralkylcarbonyloxyalkyl, mercaptocarbonyl, mercaptoalkyl, alkoxycarbonyloxy, alkylthio, cycloalkylthio, cycloalkylalkylthio, phthalimido, phthalimidoalkyl, and wherein each of $R^2$ through $R^{11}$ may be further independently selected from amino and amido radicals of the formula

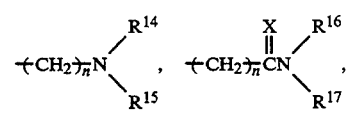
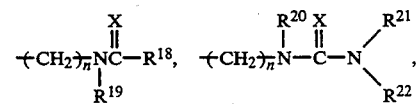

-continued

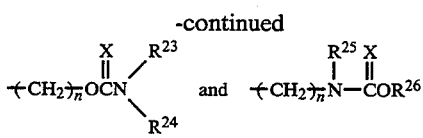

wherein X is selected from oxygen atom and sulfur atom;

wherein each n is a number independently selected from zero to six, inclusive;

wherein each of $R^{14}$ through $R^{26}$ is independently selected from hydrido, alkyl, cycloalkyl, cyano, amino, hydroxyalkyl, alkoxyalkyl, phenalkyl and phenyl;

wherein each of $R^3$ through $R^{11}$ is independently selected from hydrido, hydroxy, alkyl, hydroxyalkyl, halo, haloalkyl, cycloalkyl, alkoxy, phenalkyl, phenyl, benzoyl, phenoxy, phenalkyloxy, alkoxyalkyl, alkylcarbonyl, alkoxycarbonyl, alkenyl, cyano, nitro, carboxyl, alkylthio and mercapto;

and wherein each of $R^3$ through $R^{11}$ may be further independently selected from acidic moieties of the formula $$-Y_nA$$

wherein n is a number selected from zero through two, inclusive; wherein A is selected from carboxylic acid and bioisosteres of carboxylic acid selected from

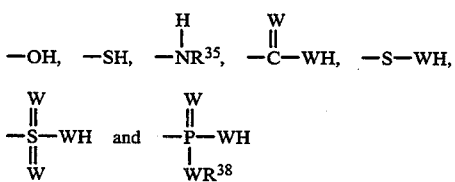

wherein each W is independently selected from oxygen atom, sulfur atom and $NR^{39}$; wherein each of $R^{35}$, $R^{38}$ and $R^{39}$ is independently selected from hydrido, alkyl, haloalkyl, haloalkylsulfonyl, haloalkylcarbonyl, cycloalkyl, phenyl and benzyl; wherein each of $R^{35}$ and $R^{39}$ may be further independently selected from amino radical of the formula

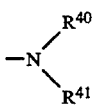

wherein each of $R^{40}$ and $R^{41}$ is independently selected from hydrido, alkyl, cycloalkyl, hydroxyalkyl, haloalkyl, alkoxyalkyl, benzyl and phenyl; and the amide, ester and salt derivatives of said acidic groups;

wherein Y is a spacer group independently selected from one or more of alkyl, cycloalkyl, cycloalkylalkyl, alkenyl, phenyl, phenalkyl and aralkyl;

wherein each of $R^1$ through $R^{26}$, $R^{35}$ and $R^{38}$ through $R^{41}$, Y and A and independently may be substituted at any substitutable position with one or more groups selected from alkyl, cycloalkyl, cycloalkylalkyl, hydroxy, halo, oxo, haloalkyl, alkoxycarbonyl, cyano, nitro, alkylsulfonyl, haloalkylsulfonyl, aryl, aralkyl, alkoxy, aryloxy and aralkoxy;

or a tautomer thereof or a pharmaceutically-acceptable salt thereof.

6. The method of claim 5 wherein m is one; wherein $R^1$ is selected from hydrido, alkyl, hydroxyalkyl, haloalkyl, cycloalkyl, cycloalkylalkyl, aralkyl, aryl, benzoyl, alkoxyalkyl, alkylcarbonyl, alkoxycarbonyl, alkenyl and alkynyl; where $R^2$ is selected from alkyl, aminoalkyl, hydroxyalkyl, halo, haloalkyl, cycloalkyl, cycloalkylalkyl, alkylcarbonyl, cycloalkylhaloalkyl, cycloalkylcarbonyl, alkoxy, aralkyl, aralkylhaloalkyl, aryl, benzoyl, phenoxy, phenoxyalkyl, phenalkyloxy, phenylthio, phenalkylthio, aralkoxy, alkoxyalkyl, acetyl, alkoxycarbonyl, alkenyl, cycloalkenyl, alkynyl, cyano, nitro, carboxyl, carboxyalkyl, alkylcarbonyloxy, mercaptoalkyl, mercaptocarbonyl, alkoxycarbonyloxy, alkylcarbonyloxyalkyl, alkoxycarbonylalkyl, aralkoxycarbonylalkyl, aralkylcarbonyloxyalkyl, phthalimido, phthalimidoalkyl, imidazoalkyl, tetrazole, tetrazolealkyl, alkylthio, cycloalkylthio, cycloalkylalkylthio, and amino and amido radicals of the formula

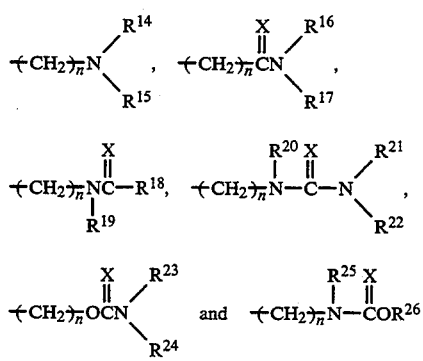

wherein X is selected from oxygen atom and sulfur atom;

wherein each n is a number independently selected from zero to six, inclusive;

wherein each of $R^{14}$ through $R^{26}$ is independently selected from hydrido, alkyl, cycloalkyl, cyano, amino, hydroxyalkyl, alkoxyalkyl, phenalkyl and phenyl;

wherein each of $R^3$ through $R^{11}$ is independently selected from hydrido, hydroxy, alkyl, hydroxyalkyl, halo, haloalkyl, alkoxy, phenyl, benzoyl, phenoxy, alkoxyalkyl, acetyl, alkoxycarbonyl, alkenyl, cyano, nitro, carboxyl, alkylthio and mercapto;

and wherein each of $R^3$ through $R^{11}$ may be further independently selected from acidic moieties consisting of $CO_2H$, $CO_2CH_3$, SH, $CH_2SH$, $C_2H_4SH$, $PO_3H_2$, $NHSO_2CF_3$, $NHSO_2C_6F_5$, $SO_3H$, $CONHNH_2$, $CONHNHSO_2CF_3$, $CONHOCH_3$, $CONHOC_2H_5$, $CONHCF_3$, OH, $CH_2OH$, $C_2H_4OH$, $OPO_3H_2$, $OSO_3H$, tetrazole and the esters, amides and salts of said acidic moieties; or a tautomer thereof or a pharmaceutically-acceptable salt thereof.

7. The method of claim 6 wherein m is one; wherein $R^1$ is selected from methyl, ethyl, n-propyl, isopropyl, n-butyl, sec-butyl, isobutyl, tert-butyl, n-pentyl, isopentyl, neopentyl, phenyl, benzyl, phenethyl, cyclohexyl, cyclohexylmethyl, 2-butenyl, 3-butenyl, 2-butynyl, 3-butynyl and 2-hydroxybutyl; wherein $R^2$ is selected from $C_4H_9(n)$, $CH_3CH_2CH=CH$, $C_3H_7(n)$, $SC_3H_7$,

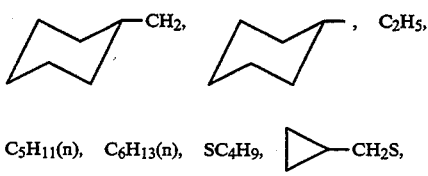

-continued

amino, aminomethyl, aminoethyl, aminopropyl, acetyl, CH₂OH CH₂OCOCH₃, CH₂Cl, Cl, CH₂OCH₃, CH₂OCH(CH₃)₂I, CHO, CH₂CO₂H, CH(CH₃)CO₂H, NO₂, Cl,

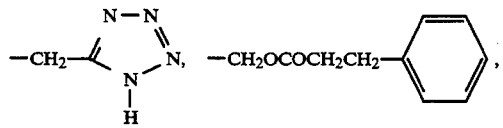

—CO₂CH₃, —CONH₂, —CONHCH₃, CON(CH₃)₂,

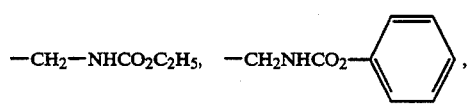

—CH₂NHCO₂CH₃, —CH₂NHCO₂C₃H₇,

—CH₂NHCO₂CH₂(CH₃)₂,    —CH₂NHCO₂C₄H₉, CH₂NHCO₂-adamantyl, —CH₂NHCO₂—(1-napthyl), —CH₂NHCONHCH₃,    —CH₂NHCONHC₂H₅, —CH₂NHCONHC₃H₇,    —CH₂NHCONHC₄H₉, —CH₂NHCONHCH(CH₃)₂, —CH₂NHCONH(1-napthyl), —CH₂NHCONH(1-adamantyl), CO₂H,

—CH₂CH₂CH₂F, —CH₂ONO₂,

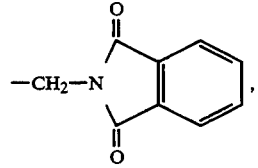

—CH₂SH, —CH₂O—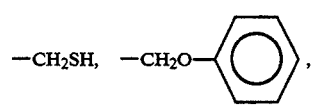,

H, Cl, NO₂, CF₃, CH₂OH, Br, F, I, methyl, ethyl, n-propyl, isopropyl, n-butyl, sec-butyl, isobutyl, tert-butyl, n-pentyl, isopentyl, neopentyl, phenyl, cyclohexyl, cyclohexylmethyl, 1-oxoethyl, 1-oxopropyl, 1-oxobutyl, 1-oxopentyl, 1, 1-dimethoxypropyl, 1, 1-dimethoxypentyl, hydroxyalkyl, halo, 1-oxo-2-phenylethyl, 1-oxo-2-cyclohexylethyl, 1,1-difluoro-2-phenylethyl, 1, 1-difluoro-2 -cyclohexylethyl, 2-cyclohexylethyl, 1,1-difluoro-3-cyclohexylpropyl, 1,1-dimethoxybutyl, 1,1-difluoroethyl, 1,1-difluoropropyl, 1,1-difluorobutyl, 1,1-difluoropentyl, benzyl, 2-phenylethyl, 1, 1-difluoro-3-phenylpropyl, cyclohexylmethyl, cyclohexanoyi, 1-butenyl, 2-butenyl, 3-butenyl, 1-butynyl, 2-butynyl, 3-butynyl and difluoromethyl; wherein each of R³ through R¹¹ is hydrido with the proviso that at least one of $R^5$, $R^6$, $R^8$ and $R^9$ is an acidic group selected from CO₂H, SH, PO₃H₂, SO₃H, CONHNH₂, CONHNHSO₂CF₃, OH,
or a tautomer thereof or a pharmaceutically-acceptable salt thereof.

8. The method of claim 7 wherein m is one; wherein $R^1$ is selected from methyl, ethyl, n-propyl, isopropyl, n-butyl, sec-butyl, isobutyl, tert-butyl, 4-methylbutyl, n-pentyl, neopentyl, phenyl, benzyl, phenethyl, cyclohexyl, cyclohexylmethyl, 2-butenyl, 3-butenyl, 2-butynyl, 3-butynyl and 2-hydroxybutyl; wherein $R^2$ is selected from ethyl, n-propyl, isopropyl, n-butyl, sec-butyl, isobutyl, 4-methylbutyl, tert-butyl, n-pentyl, neopentyl, 1-oxoethyl, 1-oxopropyl, 1-oxobutyl, 1-oxopentyl 1-oxo-2-phenylethyl, 1-oxo-2-cyclohexylethyl, 1,1-difluoro-2phenylethyl, 1,1-difluoro-2-cyclohexylethyl, 2-cyclohexylethyl, 1,1-difluoro-3-cyclohexylpropyl, 1,1-dimethoxybutyl, 1,1-difluoroethyl, 1, 1-difluoropropyl, 1,1-difluorobutyl, 1,1-difluoropentyl, benzyl, 2-phenylethyl, 1,1-difluoro-3-phenylpropyl, cyclohexylmethyl, cyclohexanoyl, acetyl, 1-butenyl, 2-butenyl, 3-butenyl, 1-butynyl, 2-butynyl, 3-butynyl, propylthio and butylthio; wherein each of $R^3$ through $R^{11}$ is hydrido with the proviso that at least one of $R^5$, $R^6$, $R^8$ and $R^9$ is an acidic group selected from CO₂H, SH, PO₃H₂, SO₃H, CONHNH₂, CONHNHSO₂CF₃, OH,
or a tautomer thereof or a pharmaceutically-acceptable salt thereof.

9. The method of claim 8 wherein said therapeutically-effective compound is selected from compounds of Formula II

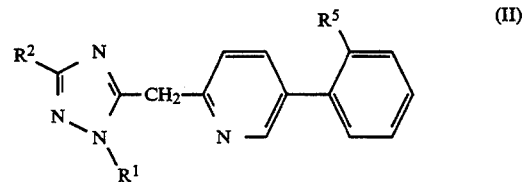

wherein m is one; wherein $R^1$ is selected from methyl, ethyl, n-propyl, isopropyl, n-butyl, sec-butyl, isobutyl, tert-butyl, 4-methylbutyl, n-pentyl, neopentyl, phenyl, benzyl, phenethyl, cyclohexyl, cyclohexyimethyl, 2-butenyl, 3-butenyl, 2-butynyl, 3-butynyl and 2-hydroxybutyl; wherein $R^2$ is selected from ethyl, n-propyl, isopropyl, n-butyl, sec-butyl, isobutyl, 4-methylbutyl, n-pentyl, 1-oxo-2-phenylethyl, 1-oxo-2-cyclohexylethyl, 1,1-difluoro-2-phenylethyl, 1,1-difluoro-2-cyclohexylethyl, 2-cyclohexylethyl, 1,1-difluoro-3-cyclohexylpropyl, 1,1-dimethoxybutyl, 1,1-difluoroethyl, 1,1-difluoropropyl, 1,1-difluorobutyl, 1,1-difluoropentyl, benzyl, 2-phenylethyl, 1,1-difluoro-3-phenylpropyl, cyclohexylmethyl, cyclohexanoyl, 1-butenyl, 2-butenyl, 3-butenyl, 1-butynyl, 2-butynyl, 3-butynyl, propylthio and butylthio; wherein $R^5$ is an acidic group selected from CO₂H and

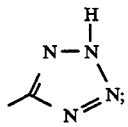

or a tautomer thereof or a pharmaceutically-acceptable salt thereof.

10. The method of claim 9 wherein said therapeutically-effective compound is selected from compounds, and their pharmaceutically-acceptable salts, of the group consisting of 5-[2-[6-[(1-butyl-3-methyl-1H-1,2,4-triazol-5-yl)methyl]-3-pyridinyl]phenyl]-1H-tetrazole;

5-[2-[6-[(1-butyl-3-ethyl-1H-1,2,4-triazol-5-yl)methyl]-3-pyridinyl]phenyl]-1H-tetrazole;

5-[2-[6-[(1-butyl-3-propyl-1H-1,2,4-triazol-5-yl)methyl]-3-pyridinyl]phenyl]-1H-tetrazole;
5-[2-[6-[(1-butyl-3-isopropyl-1H-1,2,4-triazol-5-yl)methyl ]-3-pyridinyl]phenyl]-1H-tetrazole;
5-[2-[6-[(1,3-dibutyl-1H-1,2,4-triazol-5-yl)methyl]-3pyridinyl]phenyl]- 1H-tetrazole;
5-[2-[6-[(1-butyl-3-secbutyl-1H-1,2,4-triazol-5-yl)methyl]-3pyridinyl]phenyl]-1H-tetrazole;
5-[2-[6-[(1-butyl-3-isobutyl-1H-1,2,4-triazol-5-yl)methyl]-3pyridinyl]phenyl]-1H-tetrazole;
5-[2-[6-[(1-butyl-3-tertbutyl-1H-1,2,4-triazol-5-yl)methyl]-3pyridinyl]pheny1]-1H-tetrazole;
5-[2-[6-[(1-butyl-3-pentyl-1H-1,2,4-triazol-5-yl)methyl]-3-pyridinyl]phenyl]-1H-tetrazole;
5-[2-[6-[(1-butyl-3-isopentyl-1H-1,2,4-triazol-5-yl)methyl]-3pyridinyl]phenyl]-1H-tetrazole;
5-[2-[6-[(1-butyl-3-cyclohexyl-1H-1,2,4-triazol-5-yl)methyl]-3-pyridinyl]phenyl]-1H-tetrazole;
5-[2-[6-[(1-butyl-3-cyclohexylmethyl-1H-1,2,4-triazol-5yl)methyl]-3-pyridinyl]phenyl]- 1H-tetrazole;
5-[2-[6-[[1-butyl-3-(2-cyclohexylethyl)-1H-1,2,4-triazol-5yl)methyl]-3-pyridinyl]phenyl]-1H-tetrazole;
5-[2-[6-[(1-butyl-3-phenyl-1H-1,2,4-triazol-5-yl)methyl]-3-pyridinyl]phenyl]- 1H-tetrazole;
5-[2-[6-[(1-butyl-3-phenylmethyl-1H-1,2,4 -triazol-5yl)-methyl]- 3-pyridinyl]phenyl]-1H-tetrazole; and
5-[2-[6-[(1 -butyl-3-(2 -phenylethyl)-1H- 1,2,4-triazol-5yl)methyl]-3-pyridinyl]phenyl]-1H-tetrazole.

11. The method of claim 8 wherein said therapeutically-effective compound is selected from compounds of Formula III

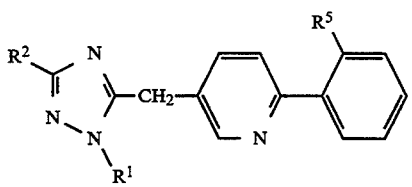

(III)

wherein m is one; wherein $R^1$ is selected from methyl, ethyl, n-propyl, isopropyl, n-butyl, sec-butyl, isobutyl, tert-butyl, 4-methylbutyl, n-pentyl, neopentyl, phenyl, benzyl, phenethyl, cyclohexyl, cyclohexylmethyl, 2-butenyl, 3-butenyl, 2-butynyl, 3-butynyl and 2-hydroxybutyl; wherein $R^2$ is selected from ethyl, n-propyl, isopropyl, n-butyl, sec-butyl, isobutyl, 4-methylbutyl, n-pentyl, 1-oxo-2-phenylethyl, 1-oxo-2-cyclohexylethyl, 1,1-difluoro-2-phenylethyl, 1,1-difluoro-2-cyclohexylethyl, 2-cyclohexylethyl, 1, 1-difluoro-3-cyclohexylpropyl, 1,1-dimethoxybutyl, 1,1 -difluoroethyl, 1,1-difluoropropyl, 1,1-difluorobutyl, 1,1-difluoropentyl, benzyl, 2-phenylethyl, 1,1-difluoro-3-phenylpropyl, cyclohexylmethyl, cyclohexanoyl, 1-butenyl, 2-butenyl, 3-butenyl, 1-butynyl, 2-butynyl, 3-butynyl, propylthio and butylthio; wherein $R^5$ is an acidic group selected from $CO_2H$ and

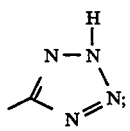

or a tautomer thereof or a pharmaceutically-acceptable salt thereof.

12. The method of claim 11 wherein said therapeutically-effective compound is selected from compounds, and their pharmaceutically-acceptable salts, of the group consisting of
5-[2-[5-[(1-butyl-3-methyl-1H-1,2,4-triazol-5-yl)methyl]-2-pyridinyl]phenyl]-1H-tetrazole;
5-[2-[5-[(1-butyl-3-ethyl-1H-1,2,4-triazol-5-yl)methyl]-2-pyridinyl]phenyl]-1H-tetrazole;
5-[2-[5-[(1-butyl-3-propyl-1H-1,2,4-triazol-5-yl)methyl]-2-pyridinyl]phenyl]-1H-tetrazole;
5-[2-[5-[(1-butyl-3-isopropyl-1H-1,2,4-triazol-5-yl)methyl]-2pyridinyl]phenyl]-1H-tetrazole;
5-[2-[5-[(1,3-dibutyl-1H-1,2,4-triazol-5-yl )methyl]-2-pyridinyl]phenyl]-1H-tetrazole;
5-[2-[5-[(1-butyl-3-secbutyl-1H-1,2,4-triazol-5-yl)methyl]-2-pyridinyl]phenyl]-1H-tetrazole;
5-[2-[5-[(1 -butyl-3-isobutyl-1H-1,2,4-triazol-5-yl)methyl]-2-pyridinyl]phenyl]-1H-tetrazole;
5-[2-[5-[(1-butyl-3-tertbutyl-1H-1,2,4-triazol-5-yl)methyl]-2pyridinyl]phenyl]-1H-tetrazole;
5-[2-[5-[(1-butyl-3-pentyl-1H-1,2,4-triazol-5-yl)methyl]-2-pyridinyl]phenyl]-1H-tetrazole; 5-[2-[5-[(1-butyl-3-isopentyl-1H-1,2,4-triazol-5-yl)methyl]-2-pyridinyl]phenyl]- 1H-tetrazole;
5-[2-[5-[(1-butyl-3-cyclohexyl-1H-1,2,4-triazol-5-yl)methyl]-2-pyridinyl]phenyl]- 1H-tetrazole;
5-[2-[5-[(1-butyl-3-cyclohexylmethyl-1H-1,2,4-triazol-5yl)methyl]-2-pyridinyl]phenyl]-1H-tetrazole;
5-[2-[5-[[1-butyl-3-(2-cyclohexylethyl)-1H-1,2,4-triazol-5yl]methyl]-2-pyridinyl]phenyl]- 1H-tetrazole;
5-[2-[5-[(1-butyl-3-phenyl-1H-1,2,4-triazol-5-yl)methyl]-2 pyridinyl]phenyl ]-1H-tetrazole;
5-[2-[5-[(1-butyl-3-phenylmethyl-1H- 1,2,4-triazol-5yl)-methyl]-2-pyridinyl]phenyl]-1H-tetrazole; and
5-[2-[5-[[1-butyl-3-(2-phenylethyl) -1H-1,2,4-triazol-5-yl]methyl]-2-pyridinyl]phenyl]-1H-tetrazole.

13. The method of claim 8 wherein said therapeutically-effective compound is selected from compounds of Formula IV

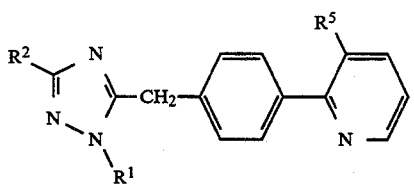

(IV)

wherein m is one; wherein $R^1$ is selected from methyl, ethyl, n-propyl, isopropyl, n-butyl, sec-butyl, isobutyl, tert-butyl, 4-methylbutyl, n-pentyl, neopentyl, phenyl, benzyl, phenethyl, cyclohexyl, cyclohexylmethyl, 2-butenyl, 3-butenyl, 2-butynyl, 3-butynyl and 2-hydroxybutyl; wherein $R^2$ is selected from ethyl, n-propyl, isopropyl, n-butyl, sec-butyl, isobutyl, 4-methylbutyl, n-pentyl, 1-oxo-2-phenylethyl, 1-oxo-2-cyclohexylethyl, 1,1-difluoro-2-phenylethyl, 1,1-difluoro-2-cyclohexylethyl, 2-cyclohexylethyl, 1,1-difluoro-3-cyclohexylpropyl, 1,1-dimethoxybutyl, 1,1-difluoroethyl, 1,1-difluoropropyl, 1,1-difluorobutyl, 1,1-difluoropentyl, benzyl, 2-phenylethyl, 1,1-difluoro-3-phenylpropyl, cyclohexylmethyl, cyclohexanoyl, 1-butenyl, 2-butenyl, 3-butenyl, 1-butynyl, 2-butynyl, 3-butynyl, propylthio and butylthio; wherein $R^5$ is an acidic group selected from $CO_2H$ and

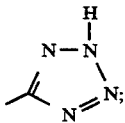

or a tautomer thereof or a pharmaceutically-acceptable salt thereof.

14. The method of claim 13 wherein said therapeutically-effective compound is selected from compounds, and their pharmaceutically-acceptable salts, of the group consisting of 5-[2-[4-[(1-butyl-3-methyl-1H-1,2,4-triazol-5-yl)methyl]phenyl]-3-pyridinyl]-1H-tetrazole;
5-[2-[4-[(1-butyl-3-ethyl-1H-1,2,4-triazol-5-yl)methyl]phenyl]- 3-pyridinyl]-1H-tetrazole;
5-[2-[4-[(1-butyl-3-propyl-1H-1,2,4-triazol-5-yl)methyl]phenyl]- 3-pyridinyl]-1H-tetrazole;
5-[2-[4-[(1-butyl-3-isopropyl-1H-1,2,4-triazol-5-yl)methyl]phenyl]-3-pyridinyl]-1H-tetrazole;
5-[2-[4-[(1,3-dibutyl-1H-1,2,4-triazol-5-yl)methyl]phenyl]-3pyridinyl]-1H-tetrazole;
5-[2-[4-[(1-butyl-3-secbutyl-1H-1,2,4-triazol-5-yl)methyl]phenyl]-3-pyridinyl]-1H-tetrazole;
5-[2-[4-[(1-butyl-3-isobutyl-1H-1,2,4-triazol-5-yl)methyl]phenyl]-3-pyridinyl]-1H-tetrazole;
5-[2-[4-[(1-butyl-3-tertbutyl-1H-1,2,4-triazol-5-yl)methyl]phenyl]- 3-pyridinyl]-1H-tetrazole;
5-[2-[4-[(1-butyl-3-pentyl-1H-1,2,4-triazol-5-yl)methyl]phenyl]- 3-pyridinyl]-1H-tetrazole;
5-[2-[4-[(1-butyl-3-isopentyl-1H-1,2,4-triazol-5-yl)methyl]phenyl]- 3-pyridinyl]-1H-tetrazole;
5-[2-[4-[(1-butyl-3-cyclohexyl-1H-1,2,4-triazol-5-yl)methyl]phenyl]- 3-pyridinyl]-1H-tetrazole;
5-[2-[4-[(1-butyl-3-cyclohexylmethyl-1H-1,2,4-triazol-5-yl)methyl]phenyl]-3-pyridinyl]-1H-tetrazole;
5-[2-[4-[[1-butyl-3-(2-cyclohexylethyl)-1H-1,2,4-triazol-5-yl]methyl]phenyl]-3-pyridinyl]-1H-tetrazole;
5-[2-[4-[(1-butyl-3-phenyl-1H-1,2,4-triazol-5-yl)methyl]phenyl]-3-pyridinyl]- 1H-tetrazole;
5-[2-[4-[(1-butyl-3-phenylmethyl-1H-1,2,4-triazol-5-yl)methyl]phenyl]-3-pyridinyl]-1H-tetrazole; and
5-[2-[4-[[1-butyl-3-(2-phenylethyl) -1H-1,2,4-triazol-5-yl]methyl]phenyl]-3-pyridinyl]-1H-tetrazole.

15. The method of claim 8 wherein said therapeutically-effective compound is selected from compounds of Formula V

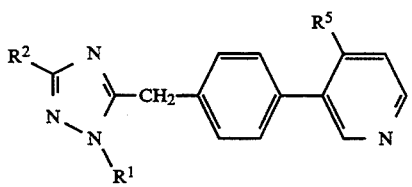

(V)

wherein m is one; wherein $R^1$ is selected from methyl, ethyl, n-propyl, isopropyl, n-butyl, sec-butyl, isobutyl, tert-butyl, 4-methylbutyl, n-pentyl, neopentyl, phenyl, benzyl, phenethyl, cyclohexyl, cyclohexylmethyl, 2-butenyl, 3-butenyl, 2-butynyl, 3-butynyl and 2-hydroxybutyl; wherein $R^2$ is selected from ethyl, n-propyl, isopropyl, n-butyl, sec-butyl, isobutyl, 4-methylbutyl, n-pentyl, 1-oxo-2-phenylethyl, 1-oxo-2-cyclohexylethyl, 1,1-difluoro-2-phenylethyl, 1,1-difluoro-2-cyclohexylethyl, 2-cyclohexylethyl, 1,1-difluoro-3-cyclohexylpropyl, 1,1-dimethoxybutyl, 1,1-difluoroethyl, 1,1-difluoropropyl, 1,1-difluorobutyl, 1,1-difluoropentyl, benzyl, 2-phenylethyl, 1,1-difluoro-3-phenylpropyl, cyclohexylmethyl, cyclohexanoyl, 1-butenyl, 2-butenyl, 3-butenyl, 1-butynyl, 2-butynyl, 3-butynyl, propylthio and butylthio; wherein $R^5$ is an acidic group selected from $CO_2H$ and

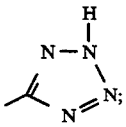

or a tautomer thereof or a pharmaceutically-acceptable salt thereof.

16. The method of claim 15 wherein said therapeutically-effective compound is selected from compounds, and their pharmaceutically-acceptable salts, of the group consisting of 5-[3-[4-[(1-butyl-3-methyl-1H-1,2,4-triazol-5-yl)methyl]phenyl]-4-pyridinyl]-1H-tetrazole;
5-[3-[4-[(1-butyl-3-ethyl-1H-1,2,4-triazol-5-yl)methyl]phenyl]-4-pyridinyl]-1H-tetrazole;
5-[3-[4-[(1-butyl-3-propyl-1H-1,2,4-triazol-5-yl)methyl]phenyl]- 4 -pyridinyl]- 1H-tetrazole;
5-[3-[4-[(1-butyl-3-isopropyl-1H-1,2,4-triazol-5-yl)methyl]phenyl]-4-pyridinyl]-1H-tetrazole;
5-[3-[4-[(1,3-dibutyl-1H-1,2,4-triazol-5-yl) methyl]phenyl]-4pyridinyl]-1H-tetrazole;
5-[3-[4-[(1-butyl-3-secbutyl-1H-1,2,4-triazol-5-yl)methyl]phenyl]-4-pyridinyl]-1H-tetrazole;
5-[3-[4-[(1-butyl-3-isobutyl-1H-1,2,4-triazol-5-yl)methyl]phenyl]- 4-pyridinyl]-1H-tetrazole;
5-[3-[4-[(1-butyl-3-tertbutyl-1H-1,2,4-triazol-5-yl)methyl]phenyl]- 4-pyridinyl]-1H-tetrazole;
5-[3-[4-[(1-butyl-3-pentyl-1H-1,2,4-triazol-5-yl)methyl]phenyl]-4-pyridinyl]-1H-tetrazole;
5-[3-[4-[(1-butyl-3-isopentyl-1H-1,2,4-triazol-5-yl)methyl]phenyl]- 4-pyridinyl]-1H-tetrazole;
5-[3-[4-[(1-butyl-3-cyclohexyl-1H-1,2,4-triazol-5-yl)methyl]phenyl]-4-pyridinyl]-1H-tetrazole;
5-[3-[4-[(1-butyl-3-cyclohexylmethyl-1H-1,2,4-triazol-5-yl)methyl]phenyl]-4-pyridinyl]-1H-tetrazole;
5-[3-[4-[[1-butyl-3-(2-cyclohexylethyl)-1H-1,2,4-triazol-5-yl]methyl]phenyl]-4-pyridinyl]-1H-tetrazole;
5-[3-[4-[(1-butyl-3-phenyl-1H-1,2,4-triazol-5-yl)methyl]phenyl]-4-pyridinyl]-1H-tetrazole;
5-[3-[4-[(1-butyl-3-phenylmethyl-1H-1,2,4-triazol-5-yl)methyl]phenyl]-4-pyridinyl]-1H-tetrazole; and
5-[3-[4-[[1-butyl-3-(2-phenylethyl)-1H-1,2,4-triazol-5-yl]methyl]phenyl]-4-pyridinyl]-1H-tetrazole.

17. The method of claim 8 wherein said therapeutically-effective compound is selected from compounds of Formula VI

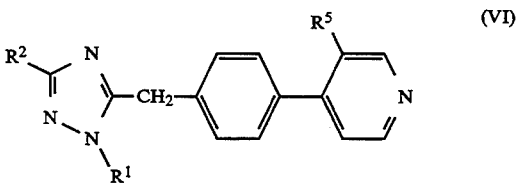

(VI)

wherein m is one; wherein $R^1$ is selected from methyl, ethyl, n-propyl, isopropyl, n-butyl, sec-butyl, isobutyl, tert-butyl, 4-methylbutyl, n-pentyl, neopentyl, phenyl, benzyl, phenethyl, cyclohexyl, cyclohexylmethyl, 2- butenyl, 3-butenyl, 2-butynyl, 3-butynyl and 2-hydroxybutyl; wherein R² is selected from ethyl, n-propyl, isopropyl, n-butyl, sec-butyl, isobutyl, 4-methylbutyl, n-pentyl, 1-oxo-2-phenylethyl, 1-oxo-2-cyclohexylethyl, 1,1-difluoro-2-phenylethyl, 1,1-difluoro-2-cyclohexylethyl, 2-cyclohexylethyl, 1,1-difluoro-3-cyclohexylpropyl, 1,1-dimethoxybutyl, 1,1-difluoroethyl, 1,1-difluoropropyl, 1,1-difluorobutyl, 1,1-difluoropentyl, benzyl, 2-phenylethyl, 1,1-difluoro-3-phenylpropyl, cyclohexylmethyl, cyclohexanoyl, 1-butenyl, 2-butenyl, 3-butenyl, 1-butynyl, 2-butynyl, 3-butynyl, propylthio and butylthio; wherein R⁵ is an acidic group selected from CO₂H and

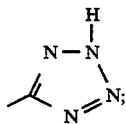

or a tautomer thereof or a pharmaceutically-acceptable salt thereof.

18. The method of claim 17 wherein said therapeutically-effective compound is selected from compounds, and their pharmaceutically-acceptable salts, of the group consisting of 5-[4-[4-[(1-butyl-3-methyl-1H-1,2,4-triazol-5-yl)methyl]phenyl]-3-pyridinyl]-1H-tetrazole;

5-[4-[4-[(1-butyl-3-ethyl-1H-1,2,4-triazol-5-yl)methyl]-phenyl]- 3-pyridinyl]-1H-tetrazole;

5-[4-[4-[(1-butyl-3-propyl-1H-1,2,4-triazol-5-yl)methyl]-phenyl]-3-pyridinyl]-1H-tetrazole;

5-[4-[4-[(1-butyl-3-isopropyl-1H-1,2, 4-triazol-5-yl)methyl]phenyl]-3-pyridinyl]-1H-tetrazole;

5-[4-[4-[(1, 3-dibutyl-1H-1,2,4-triazol-5-yl)methyl]-phenyl]-3pyridinyl]-1H-tetrazole;

5-[4-[4-[(1-butyl-3-secbutyl-1H-1,2,4-triazol-5-yl)methyl]phenyl]-3-pyridinyl]-1H-tetrazole;

5-[4-[4-[(1-butyl-3-isobutyl-1H-1,2,4-triazol-5-yl)methyl]phenyl]-3-pyridinyl]-1H-tetrazole;

5-[4-[4-[(1-butyl-3-tertbutyl-1H-1,2,4-triazol-5-yl)methyl]phenyl]-3-pyridinyl]-1H-tetrazole;

5-[4-[4-[(1-butyl-3-pentyl-1H-1,2,4-triazol-5-yl)methyl]-phenyl]-3-pyridinyl]-1H-tetrazole;

5-[4-[4-[(1-butyl-3-isopentyl-1H-1,2, 4-triazol-5-yl)methyl]phenyl]-3-pyridinyl]-1H-tetrazole;

5-[4-[4-[(1-butyl-3-cyclohexyl-1H-1,2,4-triazol-5-yl)methyl]phenyl]-3-pyridinyl]-1H-tetrazole;

5-[4-[4-[(1-butyl-3-cyclohexylmethyl-1H-1,2,4-triazol-5-yl)methyl]phenyl]-3-pyridinyl]-1H-tetrazole;

5-[4-[4-[[1-butyl-3-(2-cyclohexylethyl) -1H-1,2,4-triazol-5-yl]methyl]phenyl]-3-pyridinyl]-1H-tetrazole;

5-[4-[4-[(1-butyl-3-phenyl-1H-1,2,4-triazol-5-yl)methyl]-phenyl]-3-pyridinyl]-1H-tetrazole;

5-[4-[4-[(1-butyl-3-phenylmethyl-1H-1,2,4-triazol-5-yl)methyl]phenyl]-3-pyridinyl]-1H-tetrazole; and 5-[4-[4-[[1-butyl-3-(2-phenylethyl) -1H-1,2,4-triazol-5-yl]methyl]phenyl]-3-pyridinyl]-1H-tetrazole.

19. The method of claim 8 wherein said therapeutically-effective compound is selected from compounds of Formula VII

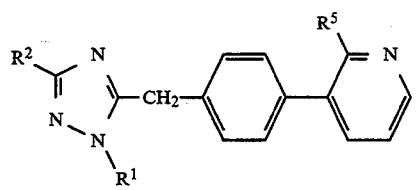

wherein m is one; wherein R¹ is selected from methyl, ethyl, n-propyl, isopropyl, n-butyl, sec-butyl, isobutyl, tert-butyl, 4-methylbutyl, n-pentyl, neopentyl, phenyl, benzyl, phenethyl, cyclohexyl, cyclohexylmethyl, 2-butenyl, 3-butenyl, 2-butynyl, 3-butynyl and 2-hydroxybutyl; wherein R² is selected from ethyl, n-propyl, isopropyl, n-butyl, sec-butyl, isobutyl, 4-methylbutyl, n-pentyl, 1-oxo-2-phenylethyl, 1-oxo-2-cyclohexylethyl, 1,1-difluoro-2-phenylethyl, 1,1 -difluoro-2-cyclohexylethyl, 2-cyclohexylethyl, 1,1-difluoro-3-cyclohexylpropyl, 1,1-dimethoxybutyl, 1,1-difluoroethyl, 1,1-difluoropropyl, 1,1-difluorobutyl, 1,1-difluoropentyl, benzyl, 2-phenylethyl, 1,1-difluoro-3-phenylpropyl, cyclohexylmethyl, cyclohexanoyl, 1-butenyl, 2-butenyl, 3-butenyl, 1-butynyl, 2-butynyl, 3-butynyl, propylthio and butylthio; wherein R⁵ is an acidic group selected from CO₂H and

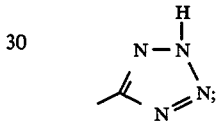

or a tautomer thereof or a pharmaceutically-acceptable salt thereof.

20. The method of claim 19 wherein said therapeutically-effective compound is selected from compounds, and their pharmaceutically-acceptable salts, of the group consisting of 5-[3-[4-[(1-butyl-3-methyl-1H-1,2,4-triazol-5-yl)methyl]phenyl]-2-pyridinyl]-1H-tetrazole;

5-[3-[4-[(1-butyl-3-ethyl-1H-1,2,4-triazol-5-yl)methyl]-phenyl]-2 -pyridinyl]-1H-tetrazole;

5-[3-[4-[(1-butyl-3-propyl-1H-1,2,4-triazol-5-yl)methyl]-phenyl]-2-pyridinyl]-1H-tetrazole;

5-[3-[4-[(1-butyl-3-isopropyl-1H-1,2,4-triazol-5-yl)methyl]phenyl]-2-pyridinyl]-1H-tetrazole;

5-[3-[4-[(1,3-dibutyl-1H- 1,2,4-triazol-5-yl)methyl]-phenyl]-2-pyridinyl]-1H-tetrazole;

5-[3-[4-[(1 -butyl- 3-secbutyl-1H-1,2,4-triazol-5-yl)methyl]phenyl]-2-pyridinyl]-1H-tetrazole;

5-[3-[4-[(1-butyl-3-isobutyl-1H-1,2,4-triazol-5-yl)methyl]phenyl]-2-pyridinyl]-1H-tetrazole;

5-[3-[4-[(1 -butyl-3-tertbutyl-1H-1,2,4 -triazol-5-yl)methyl]phenyl]-2-pyridinyl]-1H-tetrazole;

5-[3-[4-[(1-butyl-3-pentyl-1H-1,2,4-triazol-5-yl)methyl]-phenyl]-2-pyridinyl]-1H-tetrazole;

5-[3-[4-[(1-butyl-3-isopentyl-1H-1,2,4-triazol-5-yl)methyl]phenyl]-2-pyridinyl]-1H-tetrazole;

5-[3-[4-[(1-butyl-3-cyclohexyl-1H-1,2,4-triazol-5-yl)methyl]phenyl]-2-pyridinyl]-1H-tetrazole;

5-[3-[4-[(1-butyl-3-cyclohexylmethyl-1H-1,2,4-triazol-5-yl)methyl]phenyl]-2-pyridinyl]-1H-tetrazole;

5-[3-[4-[[1-butyl-3-(2-cyclohexylethyl)-1H-1,2,4-triazol-5-yl]methyl]phenyl]-2-pyridinyl]-1H-tetrazole;

5-[3-[4-[(1 -butyl-3-phenyl-1H-1,2,4-triazol-5-yl)methyl]phenyl]-2 -pyridinyl]-1H-tetrazole;

5-[3-[4-[(1-butyl-3-phenylmethyl-1H-1,2,4-triazol-5-yl)methyl]phenyl]-2-pyridinyl]-1H-tetrazole; and 5-[3-[4-[[1-butyl-3-(2-phenylethyl)-1H-1,2,4-triazol-5-yl]methyl]phenyl]-2-pyridinyl]-1H-tetrazole.

21. The method of claim 12 wherein said therapeutically-effective compound is 5-[2-[5-[(1,3-dibutyl-1H-1,2,4-triazol-5-yl)methyl]-2-pyridinyl]phenyl]-1H-tetrazole.

22. The method of claim 1 wherein said circulatory disorder is a cardiovascular disorder.

23. The method of claim 22 wherein said cardiovascular disorder is hypertension.

24. The method of claim 22 wherein said cardiovascular disorder is congestive heart failure.

* * * * *